United States Patent
Backs et al.

(10) Patent No.: US 9,914,912 B2
(45) Date of Patent: Mar. 13, 2018

(54) ABHD5 AND PARTIAL HDAC4 FRAGMENTS AND VARIANTS AS A THERAPEUTIC APPROACH FOR THE TREATMENT OF CARDIOVASCULAR DISEASES

(71) Applicant: Ruprecht-Karls-Universität Heidelberg, Heidelberg (DE)

(72) Inventors: Johannes Backs, Dossenheim (DE); Zegeye Jebessa, Heidelberg (DE); Lorenz Lehmann, Heidelberg (DE); Hugo Katus, Heidelberg (DE); Oliver Müller, Dossenheim (DE)

(73) Assignee: Ruprecht-Karls-University Heidelberg, Heidelberg (DE)

( * ) Notice: Subject to any disclaimer, the term of this patent is extended or adjusted under 35 U.S.C. 154(b) by 0 days.

(21) Appl. No.: 14/768,050

(22) PCT Filed: Feb. 17, 2014

(86) PCT No.: PCT/EP2014/053042
§ 371 (c)(1),
(2) Date: Aug. 14, 2015

(87) PCT Pub. No.: WO2014/125110
PCT Pub. Date: Aug. 21, 2014

(65) Prior Publication Data
US 2016/0108376 A1    Apr. 21, 2016

Related U.S. Application Data

(60) Provisional application No. 61/765,440, filed on Feb. 15, 2013.

(51) Int. Cl.
| | |
|---|---|
| *A61K 38/45* | (2006.01) |
| *A61K 38/48* | (2006.01) |
| *C12N 9/10* | (2006.01) |
| *C12N 9/80* | (2006.01) |
| *A61K 38/50* | (2006.01) |
| *C12Q 1/48* | (2006.01) |

(52) U.S. Cl.
CPC ............ *C12N 9/1029* (2013.01); *A61K 38/45* (2013.01); *A61K 38/48* (2013.01); *A61K 38/50* (2013.01); *C12N 9/80* (2013.01); *C12Q 1/48* (2013.01); *C12Y 203/01051* (2013.01); *C12Y 305/01098* (2013.01); *G01N 2333/91057* (2013.01); *G01N 2500/04* (2013.01); *G01N 2500/20* (2013.01)

(58) Field of Classification Search
None
See application file for complete search history.

(56) References Cited

U.S. PATENT DOCUMENTS

2009/0018066 A1* 1/2009 Zechner ................. C07K 16/40
514/4.8

FOREIGN PATENT DOCUMENTS

| WO | 2005/115461 A2 | 12/2005 |
| WO | 2007/059533 A2 | 5/2007 |

OTHER PUBLICATIONS

Backs, J., et al., Selective repression of MEF2 activity by PKA-dependent proteolysis of HDAC4. J Cell Biol. Oct. 31, 2011;195(3):403-15. doi: 10.1083/jcb.201105063.
Caviglia, J.M., et al., Adipose-selective overexpression of ABHD5/CGI-58 does not increase lipolysis or protect against diet-induced obesity. J Lipid Res. Nov. 2011;52(11):2032-42. doi: 10.1194/jlr.M019117. Epub Aug. 31, 2011.
Holh, M., et al., HDAC4 controls histone methylation in response to elevated cardiac load. J Clin Invest. Mar. 2013;123(3):1359-70. doi: 10.1172/JCI61084. Epub Feb. 22, 2013.
Invitation to Pay Additional Fees for International Application No. PCT/EP2014/053042, dated Apr. 24, 2014 (8 pages).
International Search Report for Application No. PCT/EP2014/053042, dated Jun. 30, 2014 (6 pages).
Jebessa, Z., et al., Protein kinase a prevents cardiomyocyte hypertrophy through abhydrolase domain containing 5 (ABHD5)-mediated proteolysis of histone deacetylase 4(HDAC4). Abstract 072. Circulation Research, Grune and Stratton, Baltimore, US, vol. 113, Aug. 1, 2013, 1 page.
Lass, A., et al., Adipose triglyceride lipase-mediated lipolysis of cellular fat stores is activated by CGI-58 and defective in Chanarin-Dorfman Syndrome. Cell Metab. May 2006;3(5):309-19.
Montero-Moran, G., et al., CGI-58/ABHD5 is a coenzyme A-dependent lysophosphatidic acid acyltransferase. J Lipid Res. Apr. 2010;51(4):709-19. doi: 10.1194/jlr.M001917. Epub Oct. 2, 2009.
European Office Action for Application No. 14704605.6, dated Dec. 20, 2016 (16 pages).
Short, B., PKA cuts down on HDAC4 signaling. The Journal of Cell Biology (JCB), vol. 195, issue 3, Oct. 31, 2011, p. 344, 4 pages, XP055320641. Retrieved from the Internet on Nov. 17, 2016 from <http://jcb.rupress.org/contect/195/3/344.2>.

* cited by examiner

*Primary Examiner* — Rebecca E Prouty
(74) *Attorney, Agent, or Firm* — Nutter McClennen & Fish LLP; Konstantin Linnik

(57) ABSTRACT

The present invention relates to Abhydrolase containing domain 5 (ABHD5) and N-terminal fragments of HDAC4 (HDAC4-NT) and variants of the aforementioned peptides for the treatment and prevention of heart failure. The present invention further provides vectors for the cardiomyocyte-specific expression of said peptides and a test system comprising ABHD5 for the identification of novel compounds which are useful for the treatment of heart failure.

3 Claims, 19 Drawing Sheets

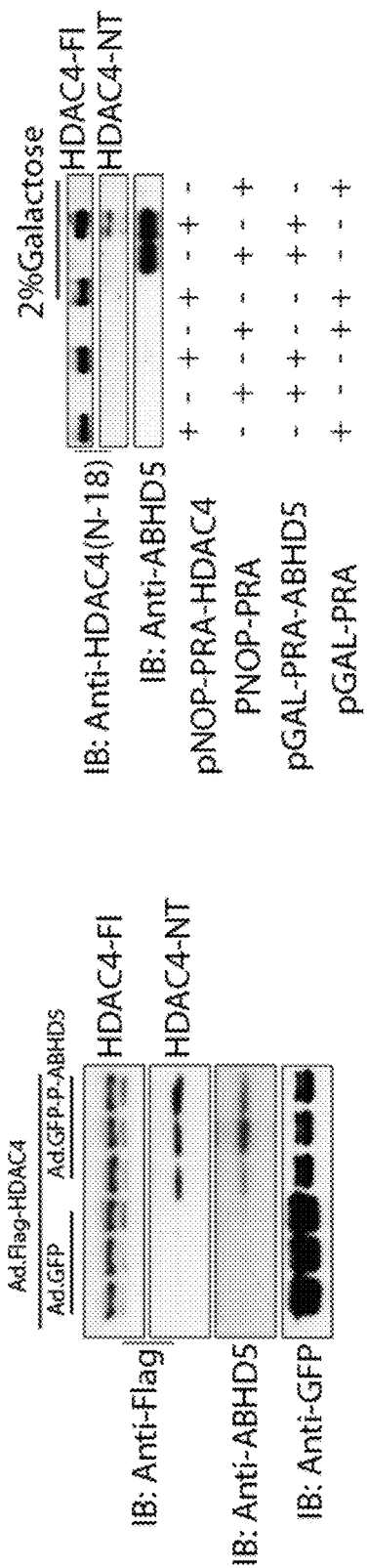
FIG. 8A
FIG. 8B
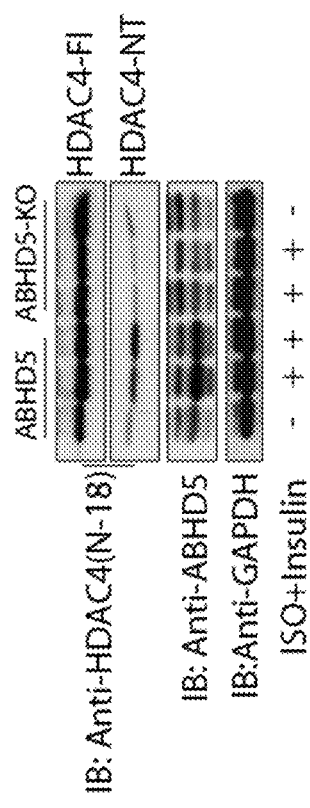
FIG. 8C

| Gene Symbol | Foldchange TAC vs sham | Foldchange TAC+NT vs sham |
|---|---|---|
| Cdkn1 | 3.50 | 0.24 |
| Gfpt2 | 2.41 | 0.34 |
| Nr4a1 | 5.92 | 0.17 |
| Egr1 | 2.90 | 0.32 |
| Fosl2 | 3.26 | 0.32 |
| Apold1 | 3.38 | 0.24 |
| Atf3 | 3.60 | 0.22 |
| Adamts1 | 3.20 | 0.34 |
| Egr2 | 4.53 | -0.31 |
| Spry4 | 2.45 | 0.46 |

Distance in groups

SEQUENCE LISTING

```
<160> NUMBER OF SEQ ID NOS: 22

<210> SEQ ID NO 1
<211> LENGTH: 349
<212> TYPE: PRT
<213> ORGANISM: Homo sapiens
<220> FEATURE:
<221> NAME/KEY: SOURCE
<222> LOCATION: 1..349
<223> OTHER INFORMATION: /mol_type="protein"
      /organism="Homo sapiens"

<400> SEQUENCE: 1

Met Ala Ala Glu Glu Glu Val Asp Ser Ala Asp Thr Gly Glu Arg
1               5                   10                  15

Ser Gly Trp Leu Thr Gly Trp Leu Pro Thr Trp Cys Pro Thr Ser Ile
                20                  25                  30

Ser His Leu Lys Glu Ala Glu Glu Lys Met Leu Lys Cys Val Pro Cys
            35                  40                  45

Thr Tyr Lys Lys Glu Pro Val Arg Ile Ser Asn Gly Asn Lys Ile Trp
        50                  55                  60

Thr Leu Lys Phe Ser His Asn Ile Ser Asn Lys Thr Pro Leu Val Leu
65                  70                  75                  80

Leu His Gly Phe Gly Gly Gly Leu Gly Leu Trp Ala Leu Asn Phe Gly
                85                  90                  95

Asp Leu Cys Thr Asn Arg Pro Val Tyr Ala Phe Asp Leu Leu Gly Phe
            100                 105                 110

Gly Arg Ser Ser Arg Pro Arg Phe Asp Ser Asp Ala Glu Glu Val Glu
        115                 120                 125

Asn Gln Phe Val Glu Ser Ile Glu Glu Trp Arg Cys Ala Leu Gly Leu
    130                 135                 140

Asp Lys Met Ile Leu Leu Gly His Asn Leu Gly Gly Phe Leu Ala Ala
```

```
            145                 150                 155                 160
Ala Tyr Ser Leu Lys Tyr Pro Ser Arg Val Asn His Leu Ile Leu Val
                    165                 170                 175

Glu Pro Trp Gly Phe Pro Glu Arg Pro Asp Leu Ala Asp Gln Asp Arg
                    180                 185                 190

Pro Ile Pro Val Trp Ile Arg Ala Leu Gly Ala Ala Leu Thr Pro Phe
                    195                 200                 205

Asn Pro Leu Ala Gly Leu Arg Ile Ala Gly Pro Phe Gly Leu Ser Leu
                    210                 215                 220

Val Gln Arg Leu Arg Pro Asp Phe Lys Arg Lys Tyr Ser Ser Met Phe
225                 230                 235                 240

Glu Asp Asp Thr Val Thr Glu Tyr Ile Tyr His Cys Asn Val Gln Thr
                    245                 250                 255

Pro Ser Gly Glu Thr Ala Phe Lys Asn Met Thr Ile Pro Tyr Gly Trp
                    260                 265                 270

Ala Lys Arg Pro Met Leu Gln Arg Ile Gly Lys Met His Pro Asp Ile
                    275                 280                 285

Pro Val Ser Val Ile Phe Gly Ala Arg Ser Cys Ile Asp Gly Asn Ser
                    290                 295                 300

Gly Thr Ser Ile Gln Ser Leu Arg Pro His Ser Tyr Val Lys Thr Ile
305                 310                 315                 320

Ala Ile Leu Gly Ala Gly His Tyr Val Tyr Ala Asp Gln Pro Glu Glu
                    325                 330                 335

Phe Asn Gln Lys Val Lys Glu Ile Cys Asp Thr Val Asp
                    340                 345

<210> SEQ ID NO 2
<211> LENGTH: 349
<212> TYPE: PRT
<213> ORGANISM: Pongo abelii
<220> FEATURE:
<221> NAME/KEY: SOURCE
<222> LOCATION: 1..349
<223> OTHER INFORMATION: /mol_type="protein"
      /organism="Pongo abelii"

<400> SEQUENCE: 2

Met Ala Ala Glu Glu Glu Val Asp Ser Ala Asp Thr Gly Glu Arg
1                   5                   10                  15

Ser Gly Trp Leu Thr Gly Trp Leu Pro Thr Trp Cys Pro Thr Ser Thr
                    20                  25                  30

Ser His Leu Lys Glu Ala Glu Glu Lys Met Leu Lys Cys Val Pro Cys
                    35                  40                  45

Thr Tyr Lys Lys Glu Pro Val His Ile Ser Asn Gly Asn Lys Ile Trp
                    50                  55                  60

Thr Leu Lys Phe Ser His Asn Ile Ser Asn Lys Thr Pro Leu Val Leu
65                  70                  75                  80

Leu His Gly Phe Gly Gly Gly Leu Gly Leu Trp Ala Leu Asn Phe Gly
                    85                  90                  95

Asp Leu Cys Thr Asn Arg Pro Val Tyr Ala Phe Asp Leu Leu Gly Phe
                    100                 105                 110

Gly Arg Ser Ser Arg Pro Arg Phe Asp Ser Asp Ala Glu Glu Val Glu
                    115                 120                 125

Asn Gln Phe Val Glu Ser Ile Glu Glu Trp Arg Cys Ala Leu Gly Leu
                    130                 135                 140

Asp Lys Met Ile Leu Leu Gly His Asn Leu Gly Gly Phe Leu Ala Ala
```

```
145                 150                 155                 160
Ala Tyr Ser Leu Lys Tyr Pro Ser Arg Val Asn His Leu Ile Leu Val
                165                 170                 175

Glu Pro Trp Gly Phe Pro Glu Arg Pro Asp Leu Ala Asp Gln Asp Arg
                180                 185                 190

Pro Ile Pro Val Trp Ile Arg Ala Leu Gly Ala Ala Leu Thr Pro Phe
                195                 200                 205

Asn Pro Leu Ala Gly Leu Arg Ile Ala Gly Pro Phe Gly Leu Ser Leu
                210                 215                 220

Val Gln Arg Leu Arg Pro Asp Phe Lys Arg Lys Tyr Ser Ser Met Phe
225                 230                 235                 240

Glu Asp Asp Thr Val Thr Glu Tyr Ile Tyr His Cys Asn Val Gln Thr
                245                 250                 255

Pro Ser Gly Glu Thr Ala Phe Lys Asn Met Thr Ile Pro Tyr Gly Trp
                260                 265                 270

Ala Lys Arg Pro Met Leu Gln Arg Ile Gly Lys Met His Pro Asp Ile
                275                 280                 285

Pro Val Ser Val Ile Phe Gly Ala Arg Ser Cys Ile Asp Gly Asn Ser
                290                 295                 300

Gly Thr Ser Ile Gln Ser Leu Arg Pro His Ser Tyr Val Lys Thr Ile
305                 310                 315                 320

Ala Ile Leu Gly Ala Gly His Tyr Val Tyr Ala Asp Gln Pro Glu Glu
                325                 330                 335

Phe Asn Gln Lys Val Lys Glu Ile Cys Asp Thr Val Asp
                340                 345

<210> SEQ ID NO 3
<211> LENGTH: 351
<212> TYPE: PRT
<213> ORGANISM: Mus musculus
<220> FEATURE:
<221> NAME/KEY: SOURCE
<222> LOCATION: 1..351
<223> OTHER INFORMATION: /mol_type="protein"
      /organism="Mus musculus"

<400> SEQUENCE: 3

Met Lys Ala Met Ala Ala Glu Glu Val Asp Ser Ala Asp Ala Gly
1               5                   10                  15

Gly Gly Ser Gly Trp Leu Thr Gly Trp Leu Pro Thr Trp Cys Pro Thr
                20                  25                  30

Ser Thr Ser His Leu Lys Glu Ala Glu Lys Met Leu Lys Cys Val
                35                  40                  45

Pro Cys Thr Tyr Lys Lys Glu Pro Val Arg Ile Ser Asn Gly Asn Arg
                50                  55                  60

Ile Trp Thr Leu Met Phe Ser His Asn Ile Ser Ser Lys Thr Pro Leu
65                  70                  75                  80

Val Leu Leu His Gly Phe Gly Gly Gly Leu Gly Leu Trp Ala Leu Asn
                85                  90                  95

Phe Glu Asp Leu Ser Thr Asp Arg Pro Val Tyr Ala Phe Asp Leu Leu
                100                 105                 110

Gly Phe Gly Arg Ser Ser Arg Pro Arg Phe Asp Ser Asp Ala Glu Glu
                115                 120                 125

Val Glu Asn Gln Phe Val Glu Ser Ile Glu Glu Trp Arg Cys Ala Leu
                130                 135                 140

Arg Leu Asp Lys Met Ile Leu Leu Gly His Asn Leu Gly Gly Phe Leu
```

```
                145                 150                 155                 160
Ala Ala Ala Tyr Ser Leu Lys Tyr Pro Ser Arg Val Ser His Leu Ile
                    165                 170                 175

Leu Val Glu Pro Trp Gly Phe Pro Glu Arg Pro Asp Leu Ala Asp Gln
            180                 185                 190

Glu Arg Pro Ile Pro Val Trp Ile Arg Ala Leu Gly Ala Leu Thr
        195                 200                 205

Pro Phe Asn Pro Leu Ala Gly Leu Arg Ile Ala Gly Pro Phe Gly Leu
    210                 215                 220

Ser Leu Val Gln Arg Leu Arg Pro Asp Phe Lys Arg Lys Tyr Ser Ser
225                 230                 235                 240

Met Phe Glu Asp Asp Thr Val Thr Glu Tyr Ile Tyr His Cys Asn Val
                245                 250                 255

Gln Thr Pro Ser Gly Glu Thr Ala Phe Lys Asn Met Thr Ile Pro Tyr
                260                 265                 270

Gly Trp Ala Lys Arg Pro Met Leu Gln Arg Ile Gly Gly Leu His Pro
            275                 280                 285

Asp Ile Pro Val Ser Val Ile Phe Gly Ala Arg Ser Cys Ile Asp Gly
        290                 295                 300

Asn Ser Gly Thr Ser Ile Gln Ser Leu Arg Pro Lys Ser Tyr Val Lys
305                 310                 315                 320

Thr Ile Ala Ile Leu Gly Ala Gly His Tyr Val Tyr Ala Asp Gln Pro
                325                 330                 335

Glu Glu Phe Asn Gln Lys Val Lys Glu Ile Cys His Thr Val Asp
                340                 345                 350
```

<210> SEQ ID NO 4
<211> LENGTH: 351
<212> TYPE: PRT
<213> ORGANISM: Rattus norvegicus
<220> FEATURE:
<221> NAME/KEY: SOURCE
<222> LOCATION: 1..351
<223> OTHER INFORMATION: /mol_type="protein"
      /organism="Rattus norvegicus"

<400> SEQUENCE: 4

```
Met Lys Ala Met Ala Ala Glu Glu Val Asp Ser Ala Asp Ala Gly
1               5                   10                  15

Gly Gly Ser Gly Trp Leu Thr Gly Trp Leu Pro Thr Trp Cys Pro Thr
                20                  25                  30

Ser Thr Ser His Leu Lys Glu Ala Glu Lys Met Leu Lys Cys Val
            35                  40                  45

Pro Cys Thr Tyr Lys Lys Glu Pro Val Arg Ile Ser Asn Gly Asn Ser
    50                  55                  60

Ile Trp Thr Leu Met Phe Ser His Asn Met Ser Ser Lys Thr Pro Leu
65                  70                  75                  80

Val Leu Leu His Gly Phe Gly Gly Gly Leu Gly Leu Trp Ala Leu Asn
                85                  90                  95

Phe Glu Asp Leu Ser Thr Asp Arg Pro Val Tyr Ala Phe Asp Leu Leu
            100                 105                 110

Gly Phe Gly Arg Ser Ser Arg Pro Arg Phe Asp Ser Asp Ala Glu Glu
        115                 120                 125

Val Glu Asn Gln Phe Val Glu Ser Ile Glu Glu Trp Arg Cys Ala Leu
    130                 135                 140

Arg Leu Asp Lys Met Ile Leu Leu Gly His Asn Leu Gly Gly Phe Leu
```

```
                145                 150                 155                 160
        Ala Ala Ala Tyr Ser Leu Lys Tyr Pro Ser Arg Val Ser His Leu Ile
                        165                 170                 175

Leu Val Glu Pro Trp Gly Phe Pro Glu Arg Pro Asp Leu Ala Asp Gln
                        180                 185                 190

Glu Arg Pro Ile Pro Val Trp Ile Arg Ala Leu Gly Ala Leu Thr
                        195                 200                 205

Pro Phe Asn Pro Leu Ala Gly Leu Arg Ile Ala Gly Pro Phe Gly Leu
                210                 215                 220

Ser Leu Val Gln Arg Leu Arg Pro Asp Phe Lys Arg Lys Tyr Ser Ser
        225                 230                 235                 240

Met Phe Glu Asp Asp Thr Val Thr Glu Tyr Ile Tyr His Cys Asn Val
                        245                 250                 255

Gln Thr Pro Ser Gly Glu Thr Ala Phe Lys Asn Met Thr Ile Pro Tyr
                        260                 265                 270

Gly Trp Ala Lys Arg Pro Met Leu Gln Arg Ile Gly Gly Leu His Pro
                        275                 280                 285

Asp Ile Pro Val Ser Val Ile Phe Gly Ala Arg Ser Cys Ile Asp Gly
                290                 295                 300

Asn Ser Gly Thr Ser Ile Gln Ser Leu Arg Pro Lys Ser Tyr Val Lys
        305                 310                 315                 320

Thr Ile Ala Ile Leu Gly Ala Gly His Tyr Val Tyr Ala Asp Gln Pro
                        325                 330                 335

Glu Glu Phe Asn Gln Lys Val Lys Glu Ile Cys His Thr Val Asp
                        340                 345                 350

<210> SEQ ID NO 5
<211> LENGTH: 349
<212> TYPE: PRT
<213> ORGANISM: Sus scrofa
<220> FEATURE:
<221> NAME/KEY: SOURCE
<222> LOCATION: 1..349
<223> OTHER INFORMATION: /mol_type="protein"
      /organism="Sus scrofa"

<400> SEQUENCE: 5

Met Ala Ala Glu Glu Glu Met Asp Ser Thr Asp Ala Cys Glu Arg
1               5                   10                  15

Ser Gly Trp Leu Thr Gly Trp Leu Pro Thr Trp Cys Pro Thr Ser Thr
                20                  25                  30

Ser His Leu Lys Glu Ala Glu Glu Lys Ile Leu Lys Cys Val Pro Cys
                35                  40                  45

Ile Tyr Lys Lys Gly Pro Val Arg Ile Ser Asn Gly Asn Lys Ile Trp
        50                  55                  60

Thr Leu Lys Leu Ser His Asn Ile Ser Asn Lys Ile Pro Leu Val Leu
65                  70                  75                  80

Leu His Gly Phe Gly Gly Gly Leu Gly Leu Trp Ala Leu Asn Phe Gly
                85                  90                  95

Asp Leu Cys Thr Asn Arg Pro Val Tyr Ala Phe Asp Leu Leu Gly Phe
                100                 105                 110

Gly Arg Ser Ser Arg Pro Arg Phe Asp Thr Asp Ala Glu Glu Val Glu
                115                 120                 125

Asn Gln Phe Val Glu Ser Ile Glu Glu Trp Arg Cys Ala Leu Gly Leu
                130                 135                 140

Asp Lys Val Ile Leu Leu Gly His Asn Leu Gly Gly Phe Leu Ala Ala
```

```
                145                 150                 155                 160
        Ala Tyr Ser Leu Lys Tyr Pro Ser Arg Val Ser His Leu Ile Leu Val
                        165                 170                 175

Glu Pro Trp Gly Phe Pro Glu Arg Pro Asp Leu Ala Asp Gln Glu Arg
                        180                 185                 190

Pro Ile Pro Val Trp Ile Arg Ala Leu Gly Ala Ala Leu Thr Pro Phe
                        195                 200                 205

Asn Pro Leu Ala Gly Leu Arg Ile Ala Gly Pro Phe Gly Leu Ser Leu
                210                 215                 220

Val Gln Arg Leu Arg Pro Asp Phe Lys Arg Lys Tyr Ser Ser Met Phe
        225                 230                 235                 240

Glu Asp Asp Thr Val Thr Glu Tyr Ile Tyr His Cys Asn Val Gln Thr
                        245                 250                 255

Pro Ser Gly Glu Thr Ala Phe Lys Asn Met Thr Ile Pro Tyr Gly Trp
                        260                 265                 270

Ala Lys Arg Pro Met Leu His Arg Ile Gly Lys Met Asn Pro Asp Ile
                        275                 280                 285

Pro Val Ser Val Ile Tyr Gly Ala Arg Ser Cys Ile Asp Gly Asn Ser
                290                 295                 300

Gly Thr Ser Ile Gln Ser Leu Arg Pro His Ser Tyr Val Lys Thr Ile
        305                 310                 315                 320

Ala Ile Leu Gly Ala Gly His Tyr Val Tyr Ala Asp Gln Pro Glu Asp
                        325                 330                 335

Phe Asn Leu Lys Val Lys Glu Ile Cys Asp Thr Val Asp
                        340                 345
```

<210> SEQ ID NO 6
<211> LENGTH: 1328
<212> TYPE: DNA
<213> ORGANISM: Homo sapiens
<220> FEATURE:
<221> NAME/KEY: source
<222> LOCATION: 1..1328
<223> OTHER INFORMATION: /mol_type="DNA"
      /organism="Homo sapiens"

<400> SEQUENCE: 6

```
gcggctatgg cggcggagga ggaggaggtg gactctgccg acaccggaga gaggtcagga      60
tggctaactg gttggctccc cacatggtgc cctacgtcta tatcacacct aaagaagct     120 gaagagaaga tgttaaaatg tgtgccttgc acatacaaaa agaacctgt tcgtatatct     180 aatgaaata aaatatggac actgaagttc tctcataata tttcaaataa gactccactt     240
gtccttctcc atggttttgg aggaggtctt gggctctggg cactgaattt tggagatctt     300
tgcaccaaca gacctgtcta tgcttttgac ctattgggtt ttggacgaag tagtagaccc     360
aggtttgaca gtgatgcaga agaagtggag aatcagtttg tggaatccat tgaagagtgg     420
agatgtgccc taggattgga caaaatgatc ttgcttgggc acaacctagg tggattcttg     480
gctgctgctt actcgctgaa gtacccatca agggttaatc atctcatttt agtggagcct     540
tggggtttcc ctgaacgacc agaccttgct gatcaagaca gaccaattcc agtttggatc     600
agagccttgg gagcagcatt gactcccttt aaccctttag ctggcctaag gattgcagga     660 cccttggtt taagtctagt gcagcgttta aggcctgatt tcaaacgaaa gtattcttca     720
atgttcgaag acgatactgt gacagaatac atctaccact gtaatgtgca gactccaagt     780
ggtgagacag cttcaaagaa tatgactatt ccttatggat gggcaaaaag gccaatgctc     840
```

```
cagcgaattg gtaaaatgca ccctgacatt ccagtttcag tgatctttgg cgcccgatcc      900
tgcatagatg gcaattctgg caccagcatc cagtccttac gaccacattc atatgtgaag      960
acaatagcta ttcttggggc aggacattat gtatatgcag atcaaccaga agaattcaac     1020
cagaaagtaa aggagatctg cgacactgtg gactgaacac actgaagctc tgatgggaaa     1080
acctggtgac tgatatagtt gttcagcaat aattcatagt ctgtgatgaa gagtagtgaa     1140
tacaacacac aaccaggcag ccttcttgac tatactttgc acatgttttc tttaggaatt     1200
cactcacaca tttaaaccag ttagtgcctt ctagaagaat ggctttcctt tctcctacac     1260
aaaattgaaa tatacaagtc tctaaatata atacctttaa ataaaaggtt atttgtccct     1320
ctgaaaaa                                                              1328

<210> SEQ ID NO 7
<211> LENGTH: 3276
<212> TYPE: DNA
<213> ORGANISM: Pongo abelii
<220> FEATURE:
<221> NAME/KEY: source
<222> LOCATION: 1..3276
<223> OTHER INFORMATION: /mol_type="DNA"
      /organism="Pongo abelii"

<400> SEQUENCE: 7
ccagtcggcc tgtcagccgg cttttgagata agtccaggcg cttgcgcggc ggcggctatg       60
gcggcggagg aggaggaggt ggactctgcc gacaccggag agaggtcagg gtggctaact      120
ggttggcttc ccacatggtg ccctacgtct acatcacacc ttaaagaagc tgaagagaag      180
atgttaaaat gtgtgccttg cacatacaaa aaagaacctg ttcatatatc taatggaaat      240
aaaatatgga cactgaagtt ctctcataat atttcaaata agactccact tgtccttctc      300
catggttttg gaggaggtct tgggctctgg gcactgaatt ttggagatct ttgcaccaac      360
agacctgtct atgcttttga cctattgggt tttggacgaa gtagtagacc caggtttgac      420
agtgacgcag aagaagtgga gaatcagttt gtggaatcca ttgaagagtg gagatgtgcc      480
ctaggattgg acaaaatgat cttgcttggg cacaacctag gtggattctt ggctgctgct      540
tactcactga agtacccatc aagggttaat catctcattt tagtggagcc ttggggtttc      600
cctgaacgac cagaccttgc tgatcaagac agaccaattc cagtttggat cagagccttg      660
ggagcagcat tgactccctt taacccttta gctggcctaa ggattgcagg accctttggt      720
ttaagtctag tgcagcgttt aaggcctgat ttcaaacgaa agtattcttc aatgttcgaa      780
gacgatactg tgacagaata catctaccac tgtaatgtgc agactccaag tggtgagaca      840
gctttcaaga atatgactat tccttatgga tgggcaaaaa ggccaatgct ccagcgaatt      900
ggtaaaatgc ccctgacat tccagtttca gtgatctttg cgcccgatc ctgcatagat       960 ggcaattctg gcaccagcat ccagtcctta cgaccacatt catatgtgaa gacaatagct     1020
attcttgggg caggacatta tgtatatgca gatcaaccag aagaattcaa ccagaaagta     1080
aaggagatct gcgacactgt ggactgaaca cactgaagct ctgatgggaa aacctggtga     1140
ctgatacagt tgttcagcaa taattcatag tctgtgatga agagtaatga atacaacata     1200
gaaccaggca gccttcttga ctatactttt gcacatgttt ctttaggaa ttcgctcgca      1260 catttaaacc agttagtgcc ttctagaaga atggctttcc tttctcctac acaaaattga     1320
aatatacaag tctctaaatt taataccttt aaataaaagg ttatttgtcc ctctgatgta     1380
ctgaaaaact aattttttcag ctgaaaattt tttaatctaa ctttgctagt tattttttgta   1440
```

-continued

| | |
|---|---|
| ttgcaatcta tattgccaat ttaggaagtg atttctgagt ctcttacact gtaaaggtgc | 1500 |
| actttatttt ctttgtcttc cccatcatgt atttattgtg tcttgataac tgatattaat | 1560 |
| ctaaattcaa tgtgttttta tgtaaaaatt tgtcagttgt ttagaatatt tcactttgtt | 1620 |
| tttgaaacgg agtgacaagg cagatttttg gttaaaggac gggagttgat cactatcatt | 1680 |
| acttttcta gtttacctct tttttatatt taaggctgct aagccatgtt cagcattta | 1740 |
| aatgtggtct atcctgacat acacagtgta taacaaccta actccttgga acctcttatg | 1800 |
| tgtggtataa ttctacactt ccaaggaaca cgacttcagt gattcaggta ctgaaaagcc | 1860 |
| ttagctaaaa ggctgttgtt tccccctttc atactgttct tttccatgac ccaggatgca | 1920 |
| gcaaatgaaa cagatttctt ctcttaaggg gatattaaga ctgttacttc ctagtaagcc | 1980 |
| aagtaatacc atattttat taacatctaa cttttgtaga tgggtgctaa aattgcatac | 2040 |
| gttttaacca ctaaaataga aaaacaagtg gtgctattat gtctcatggc accagaaatg | 2100 |
| agctagcact tgggtttgtt gttgttgttt attaagagta ttgtgttaat taaatcatta | 2160 |
| catacttgaa gttatattac aaaaattcta gaaggttggt tgaactattt ttttaggaac | 2220 |
| taccatcaag tgtagcattt tcttgcagtt ttaaaatgag gaaagcttct ttgaaactgt | 2280 |
| gaaatgctcc atgtggtaac tggctgctga gaaaacccctt caccaaaaaa ataaataaaa | 2340 |
| attgaatagg attgtcatca agaaggcatc tgtcgctaac gttgcttgtc taggagaaag | 2400 |
| gtagctatgt aaataaaaac agtgaactag agcaaatagt ggtttaatgg ttttgttatt | 2460 |
| gcatttttaa aatggttaat tagggaattt gtagttgtta ggaaatgtaa ggttgtgtca | 2520 |
| ctgttgatta actgccagaa agactgaatg ttctattttc aacatttctc ccctacaaaa | 2580 |
| gaatagacaa attatactga agcatgatat aaacatcttc ccaatgaaca atttgtctca | 2640 |
| cttgtcagat taactaggtt agtgcaggaa gcaacatgag cgccaagatg tgttgtctga | 2700 |
| tttctctacc ttaagaacaa taatagtctt tttagttagt attttggatg gccaggtttc | 2760 |
| aaacctgtat gtggtacaaa taatttgggt aatattttg tattttgtt ttacacactg | 2820 |
| tccaatctca attatccttt gctgggagaa tgacaggttt cacttatata ggaaggtttt | 2880 |
| tgcacaggaa atttggtccc agcccttgga aggaagaagt tccttggttt acttagtgaa | 2940 |
| tggagtttct ggccacagat gtgccaagtg attcaagaaa gatatacctg aatatcaagt | 3000 |
| gataatttat tttcctacag actgaatttg ctttatttga aagatgttgt aactcttttt | 3060 |
| aaagttagat tttaccctga ggtatagtat atgtaatttt gtgaagattg agctagaagg | 3120 |
| gaagttcaca atcctcacat ttaaaaaaat gtagtgtgtg ctaaatgttt tcttaaaaat | 3180 |
| ctattacagc atttgatctt tgttatgcac agtgtacttt tattttacag aataaatttt | 3240 |
| cctgtgatag tcacaacaaa aaaaaaaaaa aaaaaa | 3276 |

<210> SEQ ID NO 8
<211> LENGTH: 3148
<212> TYPE: DNA
<213> ORGANISM: Mus musculus
<220> FEATURE:
<221> NAME/KEY: source
<222> LOCATION: 1..3148
<223> OTHER INFORMATION: /mol_type="DNA"
    /organism="Mus musculus"

<400> SEQUENCE: 8

| | |
|---|---|
| gccgctggga cgccgagcct gcggtggcgc ggccgcgccc tcggatcgtc ccagcgggcg | 60 |
| gacgacgcat gcgcgggcgg tgcggtctta agggcggccg cggcccgggg ccgcccagtc | 120 |

-continued

| | | | |
|---|---|---|---|
| ggcctgtcag ccggcttcga ggtgtgtccc tgcgcttgcg cggcggcggt gatgaaagcg | 180 | | |
| atggcggcgg aggaggaggt ggactcggca gacgccggtg gagggtcagg atggctgaca | 240 | | |
| gggtggcttc ctacctggtg tcccacatct acatcacacc ttaaagaagc tgaagagaaa | 300 | | |
| atgttaaaat gtgtcccctg cacttacaag aaagagcctg tgcgcatatc caatggaaac | 360 | | |
| agaatatgga cgctgatgtt ctctcacaac atttctagta agacgccact tgtcctcctt | 420 | | |
| catggttttg gaggaggtct tggactttgg gccctgaatt ttgaagatct aagcaccgat | 480 | | |
| aggcctgtct atgcctttga cctattgggc ttcggaagaa gtagtagacc taggtttgac | 540 | | |
| agtgatgcgg aagaagtgga gaatcagttt gtggaatcca ttgaagagtg gagatgtgcc | 600 | | |
| ctcaggttgg acaaaatgat cttgcttgga cacaacctgg gagggttctt ggctgccgct | 660 | | |
| tactcactga agtacccatc aagggttagt cacctcattt tagtagagcc atggggtttt | 720 | | |
| cctgagcgac cagatcttgc tgatcaagag agaccaattc cagtttggat cagggcccta | 780 | | |
| ggggcagcat tgactccctt taaccccttg gctggcctca ggattgcagg accttttggg | 840 | | |
| ttaagtctag tgcagcgttt gaggcctgat ttcaagcgga agtactcctc tatgtttgaa | 900 | | |
| gatgacacgg tgacagagta catctaccac tgtaatgtac aaaccсccaag tggtgagaca | 960 | | |
| gctttcaaaa acatgacgat tccttatggg tgggccaaac ggccaatgct tcagcggata | 1020 | | |
| ggtggcttgc atcctgacat tccagtttca gtgatctttg gagcccgatc ctgcatagat | 1080 | | |
| ggcaactctg gaaccagcat ccagtcactg cgaccgaagt cctacgtgaa gacaattgcc | 1140 | | |
| atcctcgggg cggggcatta tgtgtatgca gatcagccag aagaattcaa ccagaaagtc | 1200 | | |
| aaggagatct gccacacagt agactgagca cacagaacca tgcagcaccc gtgacgggtg | 1260 | | |
| ccgttcatga gcaatcccca cagcccgagg accccgcag tctcctggac tggactctgc | 1320 | | |
| agctttccac atttaaacca accagtgcct tctagaagaa tggctttcct ttctcctaca | 1380 | | |
| cagaattaaa atataggaga gtctcccaat ttaataatcg ccttaaataa aggttgtcct | 1440 | | |
| tctgatgtac tgaaaaattg tgattttttca gctgagactt ttctcaattt cacctaactg | 1500 | | |
| cttgttaggt gtttggtgtt gcagtccgta tgccagtgta cctagtccat atgccagtgt | 1560 | | |
| acctagtcca tatgccagtg tacctagcga cttctgggcc tgtggtgtta ggtgttggga | 1620 | | |
| agctgcactt tattttcctt gcatgtattt actgtctcta caactaaca tagttaacccc | 1680 | | |
| aagtattttt atgtaaaaag atttcaattt agaatacttc attttgaga tggagtttag | 1740 | | |
| aatatttcat tttgaaatgg aacgaaaggg ttaggttttg atgtaaaaga caggagtcaa | 1800 | | |
| tcactagcgt taactttcct tgttttcctg ttttatgatc aaggccgtgt ttcagcattt | 1860 | | |
| taaatgtgtt ccatggtgac atagtgctta cagcaacgca gttcctgggg cccttctgtg | 1920 | | |
| tgtaatctac agggttctat gagaacatat gcatagactc agccattcaa gtgctgagta | 1980 | | |
| gcccgaacct gaaacctgtc ccctttcctt ccagtattcc caggacccag gatctaggtc | 2040 | | |
| ccctcacttg cagggatgtt aacactgttg cctatcggga aaccaagtcc cactgtgttc | 2100 | | |
| tcatgagcaa ccagcttaca tggtgcttaa actggattgc atttaccac taacatttaa | 2160 | | |
| aactatgtgg tgctgttacg tctcatggcg ccagaaatga gatagaactt gtggttatt | 2220 | | |
| ttattgaata ttatgttaat ctaaccactt atatacttga agtaaaatta tgaaaaaaat | 2280 | | |
| ctattatgtt gtttgaactg tttggcagaa accaccattg gatttataac tttctgacag | 2340 | | |
| tgttaaagtg agagacaatt tgaaactatg aaaaagctcc atggaatagc tggatgctga | 2400 | | |
| gaaagccttc tgtctagaga acagagaaca aagagcattg ttaccaacat tgtttgtcca | 2460 | | |
| ggagaaaagc agattacaca aataaaacct cgacctcaca aatcacgact cgatgacttg | 2520 | | |

| | |
|---|---|
| agctattaca tttttagtga ctagtcagga aattttttg aaaatataaa attatatcac | 2580 |
| atgtaattaa ctgccagcaa gattagctcc atactttagg agaccgtgaa aatcatattg | 2640 |
| aagcgggaca aagcagcctc ccagcgaccc tttatctgac tcatttaacg cattaggtta | 2700 |
| gtgcaaggag ccaccgtgag accaaaagtg cttgttctca ccaccttgag aataaaaata | 2760 |
| gccttttttcc cccttttatag ttagtgttgt gggtggccag atccacactt gagagtggta | 2820 |
| gaacatttgt gcaggactct tacttggcag tcaccagcct cagtcttttg ttcaccaaag | 2880 |
| aaaaaaaatt ctgcacaaga aaccggtctg cccaaagaaa ctgacttccc cactgagctg | 2940 |
| ctttgcttta ctggaaacct gtgaagcttc ctaaacatta aaatttccat ggtgtgtgca | 3000 |
| gtgattgttg taaaggttga agtagtaaag tttataatct gcaaattctt gagaacagtg | 3060 |
| gttgctaaac atctttcttg taaacgatct cttaactatc attggtcttt gctaagttat | 3120 |
| tttacagaat aaactcgaca gtgctagc | 3148 |

<210> SEQ ID NO 9
<211> LENGTH: 1108
<212> TYPE: DNA
<213> ORGANISM: Rattus norvegicus
<220> FEATURE:
<221> NAME/KEY: source
<222> LOCATION: 1..1108
<223> OTHER INFORMATION: /mol_type="DNA"
     /organism="Rattus norvegicus"

<400> SEQUENCE: 9

| | |
|---|---|
| cggcttcgag gtgccttcct gcgcttgcgc ggcggcagtg atgaaagcga tggcggcgga | 60 |
| ggaggaggtg gactcggcag acgccggtgg agggtcagga tggctgacag ggtggcttcc | 120 |
| tacctggtgt cccacgtcta catcacacct taaagaagct gaagagaaaa tgctaaaatg | 180 |
| tgtcccctgc acttacaaga aagaacctgt gcgcatatcc aatggaaaca gcatatggac | 240 |
| actgatgttc tcgcacaaca tgtctagtaa gacaccactt gtcctcctgc atggttttgg | 300 |
| aggaggtctt ggactttggg ccctgaattt tgaagatcta agcactgata ggcctgtcta | 360 |
| tgcctttgac ctattgggct ttggaagaag tagtagaccc aggtttgaca gtgacgcgga | 420 |
| agaagtggag aatcagtttg tggaatccat tgaagagtgg agatgtgccc tcaggttgga | 480 |
| caaaatgatc ttgcttggac acaacctggg agggttcttg gctgctgcct actcactgaa | 540 |
| gtacccgtca agggtcagtc acctcatttt agtagaacca tggggttttc ctgagcgacc | 600 |
| agatcttgct gatcaagaga gaccaattcc agtttggatc agagccttag ggcagcattt | 660 |
| gactcccttt aacccctgg ctggcctcag gattgcagga ccttttgggt tgagtctagt | 720 |
| gcagcgcctg aggccggact tcaagcggaa gtactcctct atgtttgaag atgacacggt | 780 |
| gacagagtac atctaccact gtaatgtaca aaccccaagt ggtgagacag ctttcaaaaa | 840 |
| catgacgatt ccttacgggt gggccaagcg gcccatgctc cagcgcatag gtggcttgca | 900 |
| ccctgacatt ccagtttcag tcatcttcgg cgcccgtcc tgcatagatg caactctgg | 960 |
| caccagcatc cagtcactgc gacccaagtc atacgtgaag acaattgcta tcctcggggc | 1020 |
| agggcattat gtgtatgcag accagccaga ggagttcaac cagaaagtca aggagatctg | 1080 |
| ccacacagta gactgagcac acggaacc | 1108 |

<210> SEQ ID NO 10
<211> LENGTH: 1353
<212> TYPE: DNA
<213> ORGANISM: Sus scrofa

```
<220> FEATURE:
<221> NAME/KEY: source
<222> LOCATION: 1..1353
<223> OTHER INFORMATION: /mol_type="DNA"
      /organism="Sus scrofa"

<400> SEQUENCE: 10
attgcgcgcg gctatggcag cagaggagga ggagatggac tccacggatg cctgtgagag    60
gtctggatgg ctaactggtt ggcttccac atggtgccct acatcgacgt cacaccttaa    120
agaagctgaa gagaaaattt taaaatgtgt cccctgcata tacaaaaaag gacctgttcg    180
tatatctaat ggaaataaaa tatggacact gaagctctct cataatattt caaataagat    240
tccccttgtc ctccttcatg gttttggagg aggtctcgga ctttgggcac tgaattttgg    300
agatctttgc accaatagac ccgtctatgc ttttgacctg ctgggctttg gacgaagtag    360
tagacccaga tttgacactg atgcagaaga agtggagaat cagtttgtgg aatccattga    420
agagtggaga tgtgccttag gattggacaa agtgatcttg ctgggacaca acctgggtgg    480
gttcctagct gctgcttact cactgaagta cccctcaagg gttagtcatc tcattttagt    540
tgaaccttgg ggttttcctg agcgaccaga ccttgctgat caagagagac caattccagt    600
ttggatcaga gccttgggag cggcattgac tcccttcaac cctttagctg gtctcaggat    660
tgcaggaccc tttggtttaa gtctagtaca gcgtttaagg cctgatttca acggaagta    720 ttcttcaatg tttgaagatg atactgtgac agaatatatc taccactgta atgttcagac    780
tcccagtggt gagactgcat tcaaaaatat gactatccct tatggatggg caaaaaggcc    840
aatgctccat cggattggta aaatgaaccc tgacattcca gtttcggtga tctacggagc    900
ccgatcctgc atagatggca attctggcac cagcatccag tcattacgac cacattcata    960
cgtgaagaca atagccattc ttggagcagg acattatgtg tatgcagatc aaccagaaga    1020
cttcaaccta aaagtaaagg agatctgtga cactgtggac tgagtgcaat gcagatgaca    1080
taggaagccc gatggctgat ccagttcctc agcaataatc cccagtctgc aatgaagagt    1140
aaggaatcca gcatgagaac caggcactct tcctgcctgt actttgcaca tgttttcttt    1200
atgaagctac tcacacattt aaaccagttg gtgccttcta gacgattggc tttcctttct    1260
cctacacaaa atcaaaatat acaagaccct ccaaatctaa tagctttaat aaaaggttat    1320
ttgtccctct gctgtaaaaa aaaaaaaaaa aaa                                 1353

<210> SEQ ID NO 11
<211> LENGTH: 1084
<212> TYPE: PRT
<213> ORGANISM: Homo sapiens
<220> FEATURE:
<221> NAME/KEY: SOURCE
<222> LOCATION: 1..1084
<223> OTHER INFORMATION: /mol_type="protein"
      /organism="Homo sapiens"

<400> SEQUENCE: 11

Met Ser Ser Gln Ser His Pro Asp Gly Leu Ser Gly Arg Asp Gln Pro
1               5                   10                  15

Val Glu Leu Leu Asn Pro Ala Arg Val Asn His Met Pro Ser Thr Val
            20                  25                  30

Asp Val Ala Thr Ala Leu Pro Leu Gln Val Ala Pro Ser Ala Val Pro
        35                  40                  45

Met Asp Leu Arg Leu Asp His Gln Phe Ser Leu Pro Val Ala Glu Pro
    50                  55                  60
```

```
Ala Leu Arg Glu Gln Gln Leu Gln Gln Glu Leu Ala Leu Lys Gln
 65                  70                  75                  80

Lys Gln Gln Ile Gln Arg Gln Ile Leu Ile Ala Glu Phe Gln Arg Gln
                 85                  90                  95

His Glu Gln Leu Ser Arg Gln His Glu Ala Gln Leu His Glu His Ile
            100                 105                 110

Lys Gln Gln Gln Glu Met Leu Ala Met Lys His Gln Gln Glu Leu Leu
        115                 120                 125

Glu His Gln Arg Lys Leu Glu Arg His Arg Gln Glu Leu Glu
    130                 135                 140

Lys Gln His Arg Glu Gln Lys Leu Gln Gln Leu Lys Asn Lys Glu Lys
145                 150                 155                 160

Gly Lys Glu Ser Ala Val Ala Ser Thr Glu Val Lys Met Lys Leu Gln
                165                 170                 175

Glu Phe Val Leu Asn Lys Lys Ala Leu Ala His Arg Asn Leu Asn
            180                 185                 190

His Cys Ile Ser Ser Asp Pro Arg Tyr Trp Tyr Gly Lys Thr Gln His
            195                 200                 205

Ser Ser Leu Asp Gln Ser Ser Pro Pro Gln Ser Gly Val Ser Thr Ser
210                 215                 220

Tyr Asn His Pro Val Leu Gly Met Tyr Asp Ala Lys Asp Phe Pro
225                 230                 235                 240

Leu Arg Lys Thr Ala Ser Glu Pro Asn Leu Lys Leu Arg Ser Arg Leu
                245                 250                 255

Lys Gln Lys Val Ala Glu Arg Ser Ser Pro Leu Leu Arg Arg Lys
            260                 265                 270

Asp Gly Pro Val Val Thr Ala Leu Lys Lys Arg Pro Leu Asp Val Thr
            275                 280                 285

Asp Ser Ala Cys Ser Ser Ala Pro Gly Ser Gly Pro Ser Ser Pro Asn
        290                 295                 300

Asn Ser Ser Gly Ser Val Ser Ala Glu Asn Gly Ile Ala Pro Ala Val
305                 310                 315                 320

Pro Ser Ile Pro Ala Glu Thr Ser Leu Ala His Arg Leu Val Ala Arg
                325                 330                 335

Glu Gly Ser Ala Ala Pro Leu Pro Leu Tyr Thr Ser Pro Ser Leu Pro
            340                 345                 350

Asn Ile Thr Leu Gly Leu Pro Ala Thr Gly Pro Ser Ala Gly Thr Ala
        355                 360                 365

Gly Gln Gln Asp Thr Glu Arg Leu Thr Leu Pro Ala Leu Gln Gln Arg
    370                 375                 380

Leu Ser Leu Phe Pro Gly Thr His Leu Thr Pro Tyr Leu Ser Thr Ser
385                 390                 395                 400

Pro Leu Glu Arg Asp Gly Gly Ala Ala His Ser Pro Leu Leu Gln His
                405                 410                 415

Met Val Leu Leu Glu Gln Pro Pro Ala Gln Ala Pro Leu Val Thr Gly
            420                 425                 430

Leu Gly Ala Leu Pro Leu His Ala Gln Ser Leu Val Gly Ala Asp Arg
        435                 440                 445

Val Ser Pro Ser Ile His Lys Leu Arg Gln His Arg Pro Leu Gly Arg
    450                 455                 460

Thr Gln Ser Ala Pro Leu Pro Gln Asn Ala Gln Ala Leu Gln His Leu
465                 470                 475                 480

Val Ile Gln Gln Gln His Gln Gln Phe Leu Glu Lys His Lys Gln Gln
```

-continued

```
                485                 490                 495
Phe Gln Gln Gln Gln Leu Gln Met Asn Lys Ile Ile Pro Lys Pro Ser
                    500                 505                 510
Glu Pro Ala Arg Gln Pro Glu Ser His Pro Glu Glu Thr Glu Glu Glu
                515                 520                 525
Leu Arg Glu His Gln Ala Leu Leu Asp Glu Pro Tyr Leu Asp Arg Leu
            530                 535                 540
Pro Gly Gln Lys Glu Ala His Ala Gln Ala Gly Val Gln Val Lys Gln
545                 550                 555                 560
Glu Pro Ile Glu Ser Asp Glu Glu Ala Glu Pro Pro Arg Glu Val
                    565                 570                 575
Glu Pro Gly Gln Arg Gln Pro Ser Glu Gln Glu Leu Leu Phe Arg Gln
                580                 585                 590
Gln Ala Leu Leu Leu Glu Gln Gln Arg Ile His Gln Leu Arg Asn Tyr
            595                 600                 605
Gln Ala Ser Met Glu Ala Ala Gly Ile Pro Val Ser Phe Gly Gly His
        610                 615                 620
Arg Pro Leu Ser Arg Ala Gln Ser Ser Pro Ala Ser Ala Thr Phe Pro
625                 630                 635                 640
Val Ser Val Gln Glu Pro Pro Thr Lys Pro Arg Phe Thr Thr Gly Leu
                    645                 650                 655
Val Tyr Asp Thr Leu Met Leu Lys His Gln Cys Thr Cys Gly Ser Ser
                660                 665                 670
Ser Ser His Pro Glu His Ala Gly Arg Ile Gln Ser Ile Trp Ser Arg
            675                 680                 685
Leu Gln Glu Thr Gly Leu Arg Gly Lys Cys Glu Cys Ile Arg Gly Arg
        690                 695                 700
Lys Ala Thr Leu Glu Glu Leu Gln Thr Val His Ser Glu Ala His Thr
705                 710                 715                 720
Leu Leu Tyr Gly Thr Asn Pro Leu Asn Arg Gln Lys Leu Asp Ser Lys
                    725                 730                 735
Lys Leu Leu Gly Ser Leu Ala Ser Val Phe Val Arg Leu Pro Cys Gly
                740                 745                 750
Gly Val Gly Val Asp Ser Asp Thr Ile Trp Asn Glu Val His Ser Ala
            755                 760                 765
Gly Ala Ala Arg Leu Ala Val Gly Cys Val Val Glu Leu Val Phe Lys
        770                 775                 780
Val Ala Thr Gly Glu Leu Lys Asn Gly Phe Ala Val Val Arg Pro Pro
785                 790                 795                 800
Gly His His Ala Glu Glu Ser Thr Pro Met Gly Phe Cys Tyr Phe Asn
                    805                 810                 815
Ser Val Ala Val Ala Ala Lys Leu Leu Gln Gln Arg Leu Ser Val Ser
                820                 825                 830
Lys Ile Leu Ile Val Asp Trp Asp Val His His Gly Asn Gly Thr Gln
            835                 840                 845
Gln Ala Phe Tyr Ser Asp Pro Ser Val Leu Tyr Met Ser Leu His Arg
        850                 855                 860
Tyr Asp Asp Gly Asn Phe Phe Pro Gly Ser Gly Ala Pro Asp Glu Val
865                 870                 875                 880
Gly Thr Gly Pro Gly Val Gly Phe Asn Val Asn Met Ala Phe Thr Gly
                    885                 890                 895
Gly Leu Asp Pro Pro Met Gly Asp Ala Glu Tyr Leu Ala Ala Phe Arg
                900                 905                 910
```

```
Thr Val Val Met Pro Ile Ala Ser Glu Phe Ala Pro Asp Val Val Leu
        915                 920                 925

Val Ser Ser Gly Phe Asp Ala Val Glu Gly His Pro Thr Pro Leu Gly
        930                 935                 940

Gly Tyr Asn Leu Ser Ala Arg Cys Phe Gly Tyr Leu Thr Lys Gln Leu
945                 950                 955                 960

Met Gly Leu Ala Gly Gly Arg Ile Val Leu Ala Leu Glu Gly Gly His
                965                 970                 975

Asp Leu Thr Ala Ile Cys Asp Ala Ser Glu Ala Cys Val Ser Ala Leu
            980                 985                 990

Leu Gly Asn Glu Leu Asp Pro Leu Pro Glu Lys Val Leu Gln Gln Arg
        995                 1000                1005

Pro Asn Ala Asn Ala Val Arg Ser Met Glu Lys Val Met Glu Ile His
    1010                1015                1020

Ser Lys Tyr Trp Arg Cys Leu Gln Arg Thr Thr Ser Thr Ala Gly Arg
1025                1030                1035                1040

Ser Leu Ile Glu Ala Gln Thr Cys Glu Asn Glu Ala Glu Thr Val
            1045                1050                1055

Thr Ala Met Ala Ser Leu Ser Val Gly Val Lys Pro Ala Glu Lys Arg
        1060                1065                1070

Pro Asp Glu Glu Pro Met Glu Glu Pro Pro Leu
        1075                1080
```

<210> SEQ ID NO 12
<211> LENGTH: 1081
<212> TYPE: PRT
<213> ORGANISM: Mus musculus
<220> FEATURE:
<221> NAME/KEY: SOURCE
<222> LOCATION: 1..1081
<223> OTHER INFORMATION: /mol_type="protein"
    /organism="Mus musculus"

<400> SEQUENCE: 12

```
Met Ser Ser Gln Ser His Pro Asp Gly Leu Ser Gly Arg Asp Gln Pro
1               5                   10                  15

Val Glu Leu Leu Asn Pro Ala Arg Val Asn His Met Pro Ser Thr Val
            20                  25                  30

Asp Val Ala Thr Ala Leu Pro Leu Gln Val Ala Pro Thr Ala Val Pro
        35                  40                  45

Met Asp Leu Arg Leu Asp His Gln Phe Ser Leu Pro Leu Glu Pro Ala
    50                  55                  60

Leu Arg Glu Gln Gln Leu Gln Gln Glu Leu Leu Ala Leu Lys Gln Lys
65                  70                  75                  80

Gln Gln Ile Gln Arg Gln Ile Leu Ile Ala Glu Phe Gln Arg Gln His
                85                  90                  95

Glu Gln Leu Ser Arg Gln His Glu Ala Gln Leu His Glu His Ile Lys
            100                 105                 110

Gln Gln Gln Glu Met Leu Ala Met Lys His Gln Gln Glu Leu Leu Glu
        115                 120                 125

His Gln Arg Lys Leu Glu Arg His Arg Gln Glu Gln Glu Leu Glu Lys
    130                 135                 140

Gln His Arg Glu Gln Lys Leu Gln Gln Leu Lys Asn Lys Glu Lys Gly
145                 150                 155                 160

Lys Glu Ser Ala Val Ala Ser Thr Glu Val Lys Met Lys Leu Gln Glu
                165                 170                 175
```

-continued

```
Phe Val Leu Asn Lys Lys Ala Leu Ala His Arg Asn Leu Asn His
            180                 185                 190

Cys Ile Ser Ser Asp Pro Arg Tyr Trp Tyr Gly Lys Thr Gln His Ser
            195                 200                 205

Ser Leu Asp Gln Ser Ser Pro Pro Gln Ser Gly Val Ser Ala Ser Tyr
            210                 215                 220

Asn His Pro Val Leu Gly Met Tyr Asp Ala Lys Asp Asp Phe Pro Leu
225                 230                 235                 240

Arg Lys Thr Ala Ser Glu Pro Asn Leu Lys Leu Arg Ser Arg Leu Lys
                245                 250                 255

Gln Lys Val Ala Glu Arg Arg Ser Ser Pro Leu Leu Arg Arg Lys Asp
            260                 265                 270

Gly Pro Val Ala Thr Ala Leu Lys Lys Arg Pro Leu Asp Val Thr Asp
            275                 280                 285

Ser Ala Cys Ser Ser Ala Pro Gly Ser Gly Pro Ser Ser Pro Asn Ser
            290                 295                 300

Ser Ser Gly Asn Val Ser Thr Glu Asn Gly Ile Ala Pro Thr Val Pro
305                 310                 315                 320

Ser Ala Pro Ala Glu Thr Ser Leu Ala His Arg Leu Val Thr Arg Glu
                325                 330                 335

Gly Ser Val Ala Pro Leu Pro Leu Tyr Thr Ser Pro Ser Leu Pro Asn
            340                 345                 350

Ile Thr Leu Gly Leu Pro Ala Thr Gly Pro Ala Ala Gly Ala Ala Gly
            355                 360                 365

Gln Gln Asp Ala Glu Arg Leu Ala Leu Pro Ala Leu Gln Gln Arg Ile
            370                 375                 380

Leu Phe Pro Gly Thr His Leu Thr Pro Tyr Leu Ser Thr Ser Pro Leu
385                 390                 395                 400

Glu Arg Asp Gly Ala Ala Ala His Asn Pro Leu Leu Gln His Met Val
                405                 410                 415

Leu Leu Glu Gln Pro Pro Thr Gln Thr Pro Leu Val Thr Gly Leu Gly
            420                 425                 430

Ala Leu Pro Leu His Ser Gln Ser Leu Val Gly Ala Asp Arg Val Ser
            435                 440                 445

Pro Ser Ile His Lys Leu Arg Gln His Arg Pro Leu Gly Arg Thr Gln
            450                 455                 460

Ser Ala Pro Leu Pro Gln Asn Ala Gln Ala Leu Gln His Leu Val Ile
465                 470                 475                 480

Gln Gln Gln His Gln Gln Phe Leu Glu Lys His Lys Gln Gln Phe Gln
                485                 490                 495

Gln Gln Gln Leu His Leu Ser Lys Ile Ile Ser Lys Pro Ser Glu Pro
            500                 505                 510

Pro Arg Gln Pro Glu Ser His Pro Glu Glu Thr Glu Glu Glu Leu Arg
            515                 520                 525

Glu His Gln Ala Leu Leu Asp Glu Pro Tyr Leu Asp Arg Leu Pro Gly
            530                 535                 540

Gln Lys Glu Pro Ser Leu Ala Gly Val Gln Val Lys Gln Glu Pro Ile
545                 550                 555                 560

Glu Ser Glu Glu Glu Glu Ala Glu Ala Thr Arg Glu Thr Glu Pro Gly
                565                 570                 575

Gln Arg Pro Ala Thr Glu Gln Glu Leu Leu Phe Arg Gln Gln Ala Leu
            580                 585                 590
```

-continued

```
Leu Leu Glu Gln Gln Arg Ile His Gln Leu Arg Asn Tyr Gln Ala Ser
        595                 600                 605

Met Glu Ala Ala Gly Ile Pro Val Ser Phe Gly Ser His Arg Pro Leu
    610                 615                 620

Ser Arg Ala Gln Ser Ser Pro Ala Ser Ala Thr Phe Pro Met Ser Val
625                 630                 635                 640

Gln Glu Pro Pro Thr Lys Pro Arg Phe Thr Thr Gly Leu Val Tyr Asp
                645                 650                 655

Thr Leu Met Lys His Gln Cys Thr Cys Gly Asn Thr Asn Ser His
            660                 665                 670

Pro Glu His Ala Gly Arg Ile Gln Ser Ile Trp Ser Arg Leu Gln Glu
        675                 680                 685

Thr Gly Leu Arg Gly Lys Cys Glu Cys Ile Arg Gly Arg Lys Ala Thr
    690                 695                 700

Leu Glu Glu Leu Gln Thr Val His Ser Glu Ala His Thr Leu Leu Tyr
705                 710                 715                 720

Gly Thr Asn Pro Leu Asn Arg Gln Lys Leu Asp Ser Lys Lys Leu Leu
                725                 730                 735

Gly Ser Leu Thr Ser Val Phe Val Arg Leu Pro Cys Gly Gly Val Gly
            740                 745                 750

Val Asp Ser Asp Thr Ile Trp Asn Glu Val His Ser Ser Gly Ala Ala
        755                 760                 765

Arg Leu Ala Val Gly Cys Val Val Glu Leu Val Phe Lys Val Ala Thr
    770                 775                 780

Gly Glu Leu Lys Asn Gly Phe Ala Val Val Arg Pro Pro Gly His His
785                 790                 795                 800

Ala Glu Glu Ser Thr Pro Met Gly Phe Cys Tyr Phe Asn Ser Val Ala
                805                 810                 815

Val Ala Ala Lys Leu Leu Gln Gln Arg Leu Asn Val Ser Lys Ile Leu
            820                 825                 830

Ile Val Asp Trp Asp Val His His Gly Asn Gly Thr Gln Gln Ala Phe
        835                 840                 845

Tyr Asn Asp Pro Asn Val Leu Tyr Met Ser Leu His Arg Tyr Asp Asp
    850                 855                 860

Gly Asn Phe Phe Pro Gly Ser Gly Ala Pro Asp Glu Val Gly Thr Gly
865                 870                 875                 880

Pro Gly Val Gly Phe Asn Val Asn Met Ala Phe Thr Gly Gly Leu Glu
                885                 890                 895

Pro Pro Met Gly Asp Ala Glu Tyr Leu Ala Ala Phe Arg Thr Val Val
            900                 905                 910

Met Pro Ile Ala Asn Glu Phe Ala Pro Asp Val Val Leu Val Ser Ser
        915                 920                 925

Gly Phe Asp Ala Val Glu Gly His Pro Thr Pro Leu Gly Gly Tyr Asn
    930                 935                 940

Leu Ser Ala Lys Cys Phe Gly Tyr Leu Thr Lys Gln Leu Met Gly Leu
945                 950                 955                 960

Ala Gly Gly Arg Leu Val Leu Ala Leu Glu Gly Gly His Asp Leu Thr
                965                 970                 975

Ala Ile Cys Asp Ala Ser Glu Ala Cys Val Ser Ala Leu Leu Gly Asn
            980                 985                 990

Glu Leu Glu Pro Leu Pro Glu Lys Val Leu His Gln Arg Pro Asn Ala
        995                 1000                1005

Asn Ala Val His Ser Met Glu Lys Val Met Asp Ile His Ser Lys Tyr
```

```
                  1010                1015                1020

Trp Arg Cys Leu Gln Arg Leu Ser Ser Thr Val Gly His Ser Leu Ile
1025                1030                1035                1040

Glu Ala Gln Lys Cys Glu Lys Glu Glu Ala Glu Thr Val Thr Ala Met
                1045                1050                1055

Ala Ser Leu Ser Val Gly Val Lys Pro Ala Glu Lys Arg Ser Glu Glu
            1060                1065                1070

Glu Pro Met Glu Glu Glu Pro Pro Leu
        1075                1080

<210> SEQ ID NO 13
<211> LENGTH: 201
<212> TYPE: PRT
<213> ORGANISM: Homo sapiens
<220> FEATURE:
<221> NAME/KEY: SOURCE
<222> LOCATION: 1..201
<223> OTHER INFORMATION: /mol_type="protein"
      /organism="Homo sapiens"

<400> SEQUENCE: 13

Met Ser Ser Gln Ser His Pro Asp Gly Leu Ser Gly Arg Asp Gln Pro
1               5                   10                  15

Val Glu Leu Leu Asn Pro Ala Arg Val Asn His Met Pro Ser Thr Val
                20                  25                  30

Asp Val Ala Thr Ala Leu Pro Leu Gln Val Ala Pro Ser Ala Val Pro
            35                  40                  45

Met Asp Leu Arg Leu Asp His Gln Phe Ser Leu Pro Val Ala Glu Pro
    50                  55                  60

Ala Leu Arg Glu Gln Gln Leu Gln Gln Glu Leu Leu Ala Leu Lys Gln
65                  70                  75                  80

Lys Gln Gln Ile Gln Arg Gln Ile Leu Ile Ala Glu Phe Gln Arg Gln
                85                  90                  95

His Glu Gln Leu Ser Arg Gln His Glu Ala Gln Leu His Glu His Ile
            100                 105                 110

Lys Gln Gln Gln Glu Met Leu Ala Met Lys His Gln Gln Glu Leu Leu
    115                 120                 125

Glu His Gln Arg Lys Leu Glu Arg His Arg Gln Glu Gln Glu Leu Glu
130                 135                 140

Lys Gln His Arg Glu Gln Lys Leu Gln Gln Leu Lys Asn Lys Glu Lys
145                 150                 155                 160

Gly Lys Glu Ser Ala Val Ala Ser Thr Glu Val Lys Met Lys Leu Gln
                165                 170                 175

Glu Phe Val Leu Asn Lys Lys Ala Leu Ala His Arg Asn Leu Asn
            180                 185                 190

His Cys Ile Ser Ser Asp Pro Arg Tyr
    195                 200

<210> SEQ ID NO 14
<211> LENGTH: 201
<212> TYPE: PRT
<213> ORGANISM: Mus musculus
<220> FEATURE:
<221> NAME/KEY: SOURCE
<222> LOCATION: 1..201
<223> OTHER INFORMATION: /mol_type="protein"
      /organism="Mus musculus"

<400> SEQUENCE: 14
```

```
Met Ser Ser Gln Ser His Pro Asp Gly Leu Ser Gly Arg Asp Gln Pro
1               5                   10                  15

Val Glu Leu Leu Asn Pro Ala Arg Val Asn His Met Pro Ser Thr Val
            20                  25                  30

Asp Val Ala Thr Ala Leu Pro Leu Gln Val Ala Pro Thr Ala Val Pro
        35                  40                  45

Met Asp Leu Arg Leu Asp His Gln Phe Ser Leu Pro Leu Glu Pro Ala
    50                  55                  60

Leu Arg Glu Gln Gln Leu Gln Gln Glu Leu Leu Ala Leu Lys Gln Lys
65                  70                  75                  80

Gln Gln Ile Gln Arg Gln Ile Leu Ile Ala Glu Phe Gln Arg Gln His
                85                  90                  95

Glu Gln Leu Ser Arg Gln His Glu Ala Gln Leu His Glu His Ile Lys
            100                 105                 110

Gln Gln Gln Glu Met Leu Ala Met Lys His Gln Gln Glu Leu Leu Glu
        115                 120                 125

His Gln Arg Lys Leu Glu Arg His Arg Gln Glu Gln Glu Leu Glu Lys
    130                 135                 140

Gln His Arg Glu Gln Lys Leu Gln Gln Leu Lys Asn Lys Glu Lys Gly
145                 150                 155                 160

Lys Glu Ser Ala Val Ala Ser Thr Glu Val Lys Met Lys Leu Gln Glu
                165                 170                 175

Phe Val Leu Asn Lys Lys Lys Ala Leu Ala His Arg Asn Leu Asn His
            180                 185                 190

Cys Ile Ser Ser Asp Pro Arg Tyr Trp
        195                 200

<210> SEQ ID NO 15
<211> LENGTH: 3255
<212> TYPE: DNA
<213> ORGANISM: Homo sapiens
<220> FEATURE:
<221> NAME/KEY: source
<222> LOCATION: 1..3255
<223> OTHER INFORMATION: /mol_type="DNA"
      /organism="Homo sapiens"

<400> SEQUENCE: 15
atgagctccc aaagccatcc agatggactt tctggccgag accagccagt ggagctgctg      60
aatcctgccc gcgtgaacca catgcccagc acggtggatg tggccacggc gctgcctctg     120
caagtggccc ctcggcagt  gcccatggac ctgcgcctgg accaccagtt ctcactgcct     180
gtggcagagc cggccctgcg ggagcagcag ctgcagcagg agctcctggc gctcaagcag     240
aagcagcaga tccagaggca gatcctcatc gctgagttcc agaggcagca cgagcagctc     300
tcccggcagc acgaggcgca gctccacgag cacatcaagc aacaacagga gatgctggcc     360
atgaagcacc agcaggagct gctggaacac cagcggaagc tggagaggca ccgccaggag     420
caggagctgg agaagcagca ccgggagcag aagctgcagc agctcaagaa caaggagaag     480
ggcaaagaga gtgccgtggc cagcacagaa gtgaagatga agttacaaga atttgtcctc     540
aataaaaaga aggcgctggc ccaccggaat ctgaaccact gcatttccag cgaccctcgc     600
tactggtacg ggaaaacgca gcacagttcc cttgaccaga gttctccacc ccagagcgga     660
gtgtcgacct cctataacca cccggtcctg ggaatgtacg acgccaaaga tgacttccct     720
cttaggaaaa cagcttctga accgaatctg aaattacggt ccaggctaaa gcagaaagtg     780
gccgaaagac ggagcagccc cctgttacgc aggaaagacg gccagtggt  cactgctcta     840
```

```
aaaaagcgtc cgttggatgt cacagactcc gcgtgcagca gcgccccagg ctccggaccc      900
agctcaccca acaacagctc cgggagcgtc agcgcggaga cggtatcgc gcccgccgtc       960
cccagcatcc cggcggagac gagtttggcg cacagacttg tggcacgaga aggctcggcc     1020
gctccacttc ccctctacac atcgccatcc ttgcccaaca tcacgctggg cctgcctgcc     1080
accggcccct ctgcgggcac ggcgggccag caggacaccg agagactcac ccttcccgcc     1140
ctccagcaga ggctctccct tttccccggc acccacctca ctccctacct gagcacctcg     1200
cccttggagc gggacggagg ggcagcgcac agccctcttc tgcagcacat ggtcttactg     1260
gagcagccac cggcacaagc acccctcgtc acaggcctgg gagcactgcc cctccacgca     1320
cagtccttgg ttggtgcaga ccgggtgtcc ccctccatcc acaagctgcg gcagcaccgc     1380
ccactggggg ggacccagtc ggcccgctg ccccagaacg cccaggctct gcagcacctg      1440
gtcatccagc agcagcatca gcagtttctg gagaaacaca gcagcagtt ccagcagcag      1500
caactgcaga tgaacaagat catccccaag ccaagcgagc cagcccggca gccggagagc     1560
caccccggagg agacggagga ggagctccgt gagcaccagg ctctgctgga cgagccctac    1620
ctggaccggc tgccggggca aaggaggcg cacgcacagg ccggcgtgca ggtgaagcag      1680
gagcccattg agagcgatga ggaagaggca gagccccac gggaggtgga gccgggccag      1740
cgccagccca gtgagcagga gctgctcttc agacagcaag ccctcctgct ggagcagcag     1800
cggatccacc agctgaggaa ctaccaggcg tccatggagg ccgccggcat ccccgtgtcc     1860
ttcggcggcc acaggcctct gtcccggccg cagtcctcac ccgcgtctgc caccttcccc    1920
gtgtctgtgc aggagccccc caccaagccg aggttcacga caggcctcgt gtatgacacg     1980
ctgatgctga agcaccagtg cacctgcggg agtagcagca gccacccga gcacgccggg      2040
aggatccaga gcatctggtc ccgcctgcag gagacgggcc tccggggcaa atgcgagtgc     2100
atccgcggac gcaaggccac cctggaggag ctacagacgg tgcactcgga agcccacacc     2160
ctcctgtatg gcacgaaccc cctcaaccgg cagaaactgg acagtaagaa acttctaggc     2220
tcgctcgcct ccgtgttcgt ccggctccct tgcggtggtg ttgggtgga cagtgacacc      2280
atatggaacg aggtgcactc ggcggggggca gcccgcctgg ctgtgggctg cgtggtagag    2340
ctggtcttca aggtgccac aggggagctg aagaatggct ttgctgtggt ccgcccccct     2400
ggacaccatg cggaggagag cacgcccatg ggcttttgct acttcaactc cgtggccgtg    2460
gcagccaagc ttctgcagca gaggttgagc gtgagcaaga tcctcatcgt ggactgggac    2520
gtgcaccatg gaaacgggac ccagcaggct ttctacagcg accctagcgt cctgtacatg    2580
tccctccacc gctacgacga tgggaacttc ttcccaggca gcggggctcc tgatgaggtg    2640
ggcacaggg ccggcgtggg tttcaacgtc aacatggctt tcaccggcgg cctggacccc    2700
cccatgggag acgctgagta cttggcggcc ttcagaacgg tggtcatgcc gatcgccagc    2760
gagtttgccc cggatgtggt gctggtgtca tcaggcttcg atgccgtgga gggccacccc    2820
accctcttg ggggctacaa cctctccgcc agatgcttcg ggtacctgac gaagcagctg    2880
atgggcctgg ctggcggccg gattgtcctg gccctcgagg aggccacga cctgaccgcc    2940
atttgcgacg cctcggaagc atgtgtttct gccttgctgg aaacgagct tgatcctctc    3000
ccagaaaagg tttacagca aagacccaat gcaaacgctg tccgttccat ggagaaagtc    3060
atggagatcc acagcaagta ctggcgctgc ctgcagcgca caacctccac agcggggcgt    3120
tctctgatcg aggctcagac ttgcgagaac gaagaagccg agacggtcac cgccatggcc    3180
```

```
tcgctgtccg tgggcgtgaa gcccgccgaa aagagaccag atgaggagcc catggaagag    3240
gagccgcccc tgtag                                                      3255

<210> SEQ ID NO 16
<211> LENGTH: 3246
<212> TYPE: DNA
<213> ORGANISM: Mus musculus
<220> FEATURE:
<221> NAME/KEY: source
<222> LOCATION: 1..3246
<223> OTHER INFORMATION: /mol_type="DNA"
      /organism="Mus musculus"

<400> SEQUENCE: 16
atgagctccc aaagccatcc agatggactt tctggccgag accagcctgt ggagctgctg      60
aatcctgccc gtgtgaacca catgcccagc acggtggacg tggctacagc gctgcctctg     120
caagtggccc ctacagcagt acccatggac ctgcgcttgg accaccagtt ctcactgccc     180
ttggaacctg cattgcggga gcagcaactg cagcaggaac tcctagcact gaaacagaag     240
cagcagatcc agcggcagat actcattgca gagttccagc gtcaacatga gcagttgtcc     300
cgacagcatg aggcacagtt gcatgaacat atcaagcagc agcaggagat gctggccatg     360
aagcaccagc aggagctgct ggagcaccag cggaaactgg agcggcaccg gcaagagcag     420
gagctggaga gcagcaccg tgagcagaag ctgcagcagc tcaagaacaa ggagaagggc     480
aaagagagtg ctgtggcgag cacagaggtg aagatgaagc tgcaggagtt tgttctcaac     540
aagaagaagg ctctagccca ccggaacctg aaccactgca tttccagcga tccccgctac     600
tggtatggga agacacagca cagctccctt gaccagagct ctccaccccca gagtggggtg     660 tcagcctcct acaaccaccc cgtcttggga atgtacgacg ccaaagatga cttccctctt     720
aggaaaacag cttctgaacc taacctgaaa ttacgctcaa ggcttaagca gaaagtagct     780
gagagacgga gcagcccct gttgcgcagg aaagatggcc ctgtggccac tgctctaaaa     840
aagcgacccc tggatgttac agactccgca tgcagcagcg ccctggctc cggtcccagc     900 tctccaaata gcagctctgg caacgtcagc actgagaatg catcgcacc cactgtgccc     960 agcgctccag ctgagacgag cttggcacac agacttgtga ctcgagaagg ctcagtcgcc    1020
ccacttcctc tctacacgtc accatcctta cccaacatca ccttgggact tcctgccact    1080
ggccctgccg ctggtgcggc aggtcagcag gatgctgaga ggcttgctct cccagctctc    1140
cagcagcgga tcttgttccc tgggacccac ctcacccccgt acctgagcac ctcgccctg    1200 gagagggacg gtgcagcagc tcacaacccc ctcctgcagc acatggtcct gctggagcag    1260
ccacccaccc agacaccct tgtcacaggc ctgggggcgc tgcccctcca ctcacagtcc    1320
ctggttggtg cggacagggt gtccccatcc attcacaagc tgcggcagca ccgccctctg    1380
gggcgcacgc agtcagcacc cctgccgcag aacgcacagg ccctgcagca cctggtgatc    1440
cagcagcagc accagcagtt cctggagaag cacaagcaac agttccagca gcagcagctg    1500
cacctcagca agataatctc caaacctagt gagccacctc ggcagcctga gagccaccca    1560
gaggagacag aggaggagct ccgtgagcac caggccttgc tggatgagcc ctacctagat    1620
cggctacctg gcagaaagga gccctccctg gctggtgtgc aggtgaagca ggagcccatt    1680
gagagtgagg aggaagaagc ggaggccact cgagagacag agccgggcca gcgcccagcc    1740
actgagcagg agctgctctt cagacagcaa gccctcctac tggagcagca gaggatccac    1800
cagttaagaa actaccaggc atctatggag gctgctggca tccctgtgtc atttggcagc    1860
```

| | |
|---|---|
| cacagacctc tgtctcgggc acagtcctcc ccagcatctg ccaccttccc catgtcagtc | 1920 |
| caggagcccc ccaccaagcc aaggttcacc acaggtcttg tgtatgacac actgatgttg | 1980 |
| aagcatcagt gcacctgtgg gaacaccaac agccacccgg agcatgctgg gaggatccag | 2040 |
| agcatctggt cccgcctgca ggagactgga ctccgtggca agtgtgagtg catccgtgga | 2100 |
| cgcaaggcca cattggagga gctgcagaca gtgcactcgg aggcccacac actcctctac | 2160 |
| ggcacaaatc ctctcaacag acagaaactg acagtaagaa aacttctagg ctcgctgacc | 2220 |
| tcagtgttcg tcaggcttcc ttgtggtggt gttggggtgg atagcgacac catatggaat | 2280 |
| gaggtgcact cgtctgggc agcccgcctg gctgtaggct gtgtagtgga gctggtcttc | 2340 |
| aaggtggcca cgggagagct aaagaatggc tttgctgtgg ttcgtccccc aggacaccat | 2400 |
| gccgaggaga gcacacccat gggtttctgc tactttaact ccgtggcagt tgcagccaaa | 2460 |
| cttctccagc agaggctgaa tgtgagcaag atcctcattg tagactggga tgtacatcat | 2520 |
| gggaatggga cccagcaggc cttctacaat gaccccaatg ttctctacat gtccctgcac | 2580 |
| cgctatgacg atgggaactt cttcccagga agtggagcac cagatgaggt gggcacaggg | 2640 |
| ccaggcgtgg gtttcaatgt caacatggct ttcacgggtg gcctcgaacc ccccatggga | 2700 |
| gacgctgagt acttggcagc cttcagaacg gtggttatgc ctatcgcaaa tgagtttgcc | 2760 |
| ccagatgtgg tactggtgtc atcgggcttc gatgctgtgg agggccaccc cacacctctt | 2820 |
| ggagggtaca atctctctgc caaatgtttt gggtacttga caaaacagct gatgggctta | 2880 |
| gctggtggcc ggcttgtgct ggcccttgag ggaggccatg acctgacagc catctgtgat | 2940 |
| gcttctgaag cctgcgtgtc tgctctgctg ggaaacgagc ttgagcctct gccagaaaag | 3000 |
| gttctacatc agagacccaa tgccaatgct gtccactcca tggagaaagt gatggacatc | 3060 |
| cacagcaagt actggcgctg cctgcagcgt ctgtcctcca cggtggggca ctctctgatt | 3120 |
| gaggcgcaaa agtgtgagaa ggaagaagct gagacagtca ccgccatggc ctcgctgtct | 3180 |
| gtaggcgtca aacctgctga aagagatct gaggaggagc ccatggagga ggaaccacca | 3240 |
| ctgtag | 3246 |

<210> SEQ ID NO 17
<211> LENGTH: 603
<212> TYPE: DNA
<213> ORGANISM: Homo sapiens
<220> FEATURE:
<221> NAME/KEY: source
<222> LOCATION: 1..603
<223> OTHER INFORMATION: /mol_type="DNA"
   /organism="Homo sapiens"

<400> SEQUENCE: 17

| | |
|---|---|
| atgagctccc aaagccatcc agatggactt tctggccgag accagccagt ggagctgctg | 60 |
| aatcctgccc gcgtgaacca catgcccagc acggtggatg tggccacggc gctgcctctg | 120 |
| caagtggccc cctcggcagt gcccatggac ctgcgcctgg accaccagtt ctcactgcct | 180 |
| gtggcagagc cggccctgcg ggagcagcag ctgcagcagg agctcctggc gctcaagcag | 240 |
| aagcagcaga tccagaggca gatcctcatc gctgagttcc agaggcagca cgagcagctc | 300 |
| tcccggcagc acgaggcgca gctccacgag cacatcaagc aacaacagga gatgctggcc | 360 |
| atgaagcacc agcaggagct gctggaacac cagcggaagc tggagaggca ccgccaggag | 420 |
| caggagctgg agaagcagca ccgggagcag aagctgcagc agctcaagaa caaggagaag | 480 |
| ggcaaagaga gtgccgtggc cagcacagaa gtgaagatga agttacaaga atttgtcctc | 540 |

| aataaaaaga aggcgctggc ccaccggaat ctgaaccact gcatttccag cgaccctcgc | 600 |
| tac | 603 |

<210> SEQ ID NO 18
<211> LENGTH: 4959
<212> TYPE: DNA
<213> ORGANISM: Artificial Sequence
<220> FEATURE:
<221> NAME/KEY: source
<222> LOCATION: 1..4959
<223> OTHER INFORMATION: /mol_type="DNA"
      /note="Vector encoding human HDAC4-NT"
      /organism="Artificial Sequence"

<400> SEQUENCE: 18

| gggggggggg gggggggggg ccactccctc tctgcgcgct cgctcgctca ctgaggccgg | 60 |
| gcgaccaaag gtcgcccgac gcccgggctt tgcccgggcg gcctcagtga gcgagcgagc | 120 |
| gcgcagagag ggagtggcca actccatcac tagggttcc tagatctgaa ttcggtaccg | 180 |
| cggtggcggc cgcttcgagc tcgcccgaca ttgattattg actagttatt aatagtaatc | 240 |
| aattacgggg tcattagttc atagcccata tatggagttc cgcgttacat aacttacggt | 300 |
| aaatggcccg cctggctgac cgcccaacga cccccgccca ttgacgtcaa taatgacgta | 360 |
| tgttcccata gtaacgccaa tagggacttt ccattgacgt caatgggtgg agtatttacg | 420 |
| gtaaactgcc cacttggcag tacatcaagt gtatcatatg ccaagtacgc ccctattga | 480 |
| cgtcaatgac ggtaaatggc ccgcctggca ttatgcccag tacatgacct tatgggactt | 540 |
| tcctacttgg cagtacatct acgtattagt catcgctatt accatggtga tgcggttttg | 600 |
| gcagtacatc aatgggcgtg gatagcggtt tgactcacgg ggatttccaa gtctccaccc | 660 |
| cattgacgtc aatgggagtt tgttttggca ccaaaatcaa cgggactttc caaaatgtcg | 720 |
| taacaactcc gccccatgcg gccgctctag acccagagc acagagcatc gttcccaggc | 780 |
| caggccccag ccactgtctc tttaaccttg aaggcatttt tgggtctcac gtgtccaccc | 840 |
| aggcgggtgt cggactttga acggctctta cttcagaaga acggcatggg gtgggggggc | 900 |
| ttaggtggcc tctgcctcac ctacaactgc caaaagtggt catggggtta tttttaaccc | 960 |
| cagggaagag gtatttattg ttccacagca ggggccggcc agcaggctcc ttgaattctg | 1020 |
| cagtcgacgg taccgcggcc gcccccaatt cgagctcgcc cggggatccg ccaccatgag | 1080 |
| ctcccaaagc catccagatg gactttctgg ccgagaccag ccagtggagc tgctgaatcc | 1140 |
| tgcccgcgtg aaccacatgc cagcacggt ggatgtggcc acggcgctgc ctctgcaagt | 1200 |
| ggccccctcg gcagtgccca tggacctgcg cctggaccac cagttctcac tgcctgtggc | 1260 |
| agagccggcc ctgcgggagc agcagctgca gcaggagctc ctggcgctca agcagaagca | 1320 |
| gcagatccag aggcagatcc tcatcgctga gttccagagg cagcacgagc agctctcccg | 1380 |
| gcagcacgag gcgcagctcc acgagcacat caagcaacaa caggagatgc tggccatgaa | 1440 |
| gcaccagcag gagctgctgg aacaccagcg gaagctggag aggcacaccgcc aggagcagga | 1500 |
| gctggagaag cagcaccggg agcagaagct gcagcagctc aagaacaagg agaagggcaa | 1560 |
| agagagtgcc gtggcagca cagaagtgaa gatgaagtta caagaatttg tcctcaataa | 1620 |
| aaagaaggcg ctggcccacc ggaatctgaa ccactgcatt tccagcgacc ctcgctacta | 1680 |
| gtctagagtc ggggcggccg gccgcttcga gcagacatga taagatacat tgatgagttt | 1740 |
| ggacaaacca caactagaat gcagtgaaaa aaatgcttta tttgtgaaat ttgtgatgct | 1800 |
| attgctttat ttgtaaccat tataagctgc aataaacaag ttaacaacaa caattgcatt | 1860 |

```
cattttatgt tcaggttca gggggaggtg tgggaggttt tttaaagcaa gtaaacctc      1920 tacaaatgtg gtaaatcga taactgggga gagatctagg aaccctagt gatggagttg      1980 gccactccct ctctgcgcgc tcgctcgctc actgaggccg cccgggcaaa gcccgggcgt    2040
cgggcgacct ttggtcgccc ggcctcagtg agcgagcgag cgcgcagaga gggagtggcc    2100
cccccccccc ccccccctg cagcccagct gcattaatga atcggccaac gcgcggggag     2160
aggcggtttg cgtattgggc gctcttccgc ttcctcgctc actgactcgc tgcgctcggt    2220
cgttcggctg cggcgagcgg tatcagctca ctcaaaggcg gtaatacggt tatccacaga    2280
atcaggggat aacgcaggaa agaacatgtg agcaaaaggc cagcaaaagg ccaggaaccg    2340
taaaaaggcc gcgttgctgg cgttttccca taggctccgc cccctgacg agcatcacaa     2400 aaatcgacgc tcaagtcaga ggtggcgaaa cccgacagga ctataaagat accaggcgtt    2460
tccccctgga agctccctcg tgcgctctcc tgttccgacc ctgccgctta ccggatacct    2520
gtccgccttt ctcccttcgg gaagcgtggc gctttctcaa tgctcacgct gtaggtatct    2580
cagttcggtg taggtcgttc gctccaagct gggctgtgtg cacgaacccc ccgttcagcc    2640
cgaccgctgc gccttatccg gtaactatcg tcttgagtcc aacccggtaa gacacgactt    2700
atcgccactg gcagcagcca ctggtaacag gattagcaga gcgaggtatg taggcggtgc    2760
tacagagttc ttgaagtggt ggcctaacta cggctacact agaaggacag tatttggtat    2820
ctgcgctctg ctgaagccag ttaccttcgg aaaaagagtt ggtagctctt gatccggcaa    2880
acaaaccacc gctggtagcg gtggtttttt tgtttgcaag cagcagatta cgcgcagaaa    2940
aaaaggatct caagaagatc ctttgatctt ttctacgggg tctgacgctc agtggaacga    3000
aaactcacgt taagggattt tggtcatgag attatcaaaa aggatcttca cctagatcct    3060
tttaaattaa aaatgaagtt ttaaatcaat ctaaagtata tatgagtaaa cttggtctga    3120
cagttaccaa tgcttaatca gtgaggcacc tatctcagcg atctgtctat ttcgttcatc    3180
catagttgcc tgactccccg tcgtgtagat aactacgata cgggagggct taccatctgg    3240
ccccagtgct gcaatgatac cgcgagaccc acgctcaccg gctccagatt tatcagcaat    3300
aaaccagcca gccggaaggg ccgagcgcag aagtggtcct gcaactttat ccgcctccat    3360
ccagtctatt aattgttgcc gggaagctag agtaagtagt tcgccagtta atagtttgcg    3420
caacgttgtt gccattgcta caggcatcgt ggtgtcacgc tcgtcgtttg gtatggcttc    3480
attcagctcc ggttcccaac gatcaaggcg agttacatga tcccccatgt tgtgcaaaaa    3540
agcggttagc tccttcggtc ctccgatcgt tgtcagaagt aagttggccg cagtgttatc    3600
actcatggtt atggcagcac tgcataattc tcttactgtc atgccatccg taagatgctt    3660
ttctgtgact ggtgagtact caaccaagtc attctgagaa tagtgtatgc ggcgaccgag    3720
ttgctcttgc ccggcgtcaa tacgggataa taccgcgcca catagcagaa ctttaaaagt    3780
gctcatcatt ggaaaacgtt cttcggggcg aaaactctca aggatcttac cgctgttgag    3840
atccagttcg atgtaaccca ctcgtgcacc caactgatct tcagcatctt ttactttcac    3900
cagcgtttct gggtgagcaa aaacaggaag gcaaaatgcc gcaaaaaagg gaataagggc    3960
gacacggaaa tgttgaatac tcatactctt ccttttttcaa tattattgaa gcatttatca    4020
gggttattgt ctcatgagcg gatacatatt tgaatgtatt tagaaaaata aacaaatagg    4080
ggttccgcgc acatttcccc gaaaagtgcc acctgacgtc taagaaacca ttattatcat    4140
gacattaacc tataaaaata ggcgtatcac gaggcccttt cgtctcgcgc gtttcggtga    4200
```

| | |
|---|---|
| tgacggtgaa aacctctgac acatgcagct cccggagacg gtcacagctt gtctgtaagc | 4260 |
| ggatgccggg agcagacaag cccgtcaggg cgcgtcagcg ggtgttggcg ggtgtcgggg | 4320 |
| ctggcttaac tatgcggcat cagagcagat tgtactgaga gtgcaccata tgcggtgtga | 4380 |
| aataccgcac agatgcgtaa ggagaaaata ccgcatcagg aaattgtaaa cgttaatatt | 4440 |
| ttgttaaaat tcgcgttaaa tttttgttaa atcagctcat tttttaacca ataggccgaa | 4500 |
| atcggcaaaa tcccttataa atcaaaagaa tagaccgaga tagggttgag tgttgttcca | 4560 |
| gtttggaaca agagtccact attaaagaac gtggactcca acgtcaaagg gcgaaaaacc | 4620 |
| gtctatcagg gcgatggccc actacgtgaa ccatcaccct aatcaagttt tttggggtcg | 4680 |
| aggtgccgta aagcactaaa tcggaaccct aaagggagcc cccgatttag agcttgacgg | 4740 |
| ggaaagccgg cgaacgtggc gagaaaggaa gggaagaaag cgaaaggagc gggcgctagg | 4800 |
| gcgctggcaa gtgtagcggt cacgctgcgc gtaaccacca cacccgccgc gcttaatgcg | 4860 |
| ccgctacagg gcgcgtcgcg ccattcgcca ttcaggctac gcaactgttg ggaagggcga | 4920 |
| tcggtgcggg cctcttcgct attacgccag ctggctgca | 4959 |

<210> SEQ ID NO 19
<211> LENGTH: 5932
<212> TYPE: DNA
<213> ORGANISM: Artificial Sequence
<220> FEATURE:
<221> NAME/KEY: source
<222> LOCATION: 1..5932
<223> OTHER INFORMATION: /mol_type="DNA"
    /note="Vector for cardiomyocyte-specific expression of
    transgenes"
    /organism="Artificial Sequence"

<400> SEQUENCE: 19

| | |
|---|---|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtggaatt cacgcgtctc | 120 |
| agtccattag gagccagtag cctggaagat gtctttaccc ccagcatcag ttcaagtgga | 180 |
| gcagcacata actcttgccc tctgccttcc aagattctgg tgctgagact tatggagtgt | 240 |
| cttggaggtt gccttctgcc ccccaaccct gctcccagct ggccctccca ggcctgggtt | 300 |
| gctggcctct gctttatcag gattctcaag agggacagct ggtttatgtt gcatgactgt | 360 |
| tccctgcata tctgctctgg ttttaaatag cttatctgag cagctggagg accacatggg | 420 |
| cttatatggc gtggggtaca tgttcctgta gccttgtccc tggcacctgc caaaatagca | 480 |
| gccaacaccc cccaccccca ccgccatccc cctgccccac ccgtcccctg tcgcacattc | 540 |
| ctccctccgc agggctggct caccaggccc cagcccacat gctgcttaa agccctctcc | 600 |
| atcctctgcc tcacccagtc ccaagcttta ttgcggtagt ttatcacagt taaattgcta | 660 |
| acgcagtcag tgcttctgac acaacagtct cgaacttaag ctgcagaagt tggtcgtgag | 720 |
| gcactgggca ggtaagtatc aaggttacaa gacaggttta aggagaccaa tagaaactgg | 780 |
| gcttgtcgag acagagaaga ctcttgcgtt tctgataggc acctattggt cttactgaca | 840 |
| tccactttgc ctttctctcc acaggtgtcc actcccagtt caattacagc tcttaaggct | 900 |
| agagtactta atacgactca ctataggcta gcctcgacgg taccgcgggc ccgggatccg | 960 |
| ccaccatggc ttccaaggtg tacgaccccg agcaacgcaa acgcatgatc actgggcctc | 1020 |
| agtggtgggc tcgctgcaag caaatgaacg tgctggactc cttcatcaac tactatgatt | 1080 |
| ccgagaagca cgccgagaac gccgtgattt ttctgcatgg taacgctgcc tccagctacc | 1140 |

```
tgtggaggca cgtcgtgcct cacatcgagc ccgtggctag atgcatcatc cctgatctga    1200
tcggaatggg taagtccggc aagagcggga atggctcata tcgcctcctg gatcactaca    1260
agtacctcac cgcttggttc gagctgctga accttccaaa gaaaatcatc tttgtgggcc    1320
acgactgggg ggcttgtctg gcctttcact actcctacga gcaccaagac aagatcaagg    1380
ccatcgtcca tgctgagagt gtcgtggacg tgatcgagtc ctgggacgag tggcctgaca    1440
tcgaggagga tatcgccctg atcaagagcg aagagggcga gaaatggtg cttgagaata    1500 acttcttcgt cgagaccatg ctcccaagca agatcatgcg gaaactggag cctgaggagt    1560
tcgctgccta cctggagcca ttcaaggaga gggcgaggt tagacggcct accctctcct    1620
ggcctcgcga gatccctctc gttaagggag gcaagcccga cgtcgtccag attgtccgca    1680
actacaacgc ctaccttcgg gccagcgacg atctgcctaa gatgttcatc gagtccgacc    1740 ctggggttctt ttccaacgct attgtcgagg gagctaagaa gttccctaac accgagttcg    1800
tgaaggtgaa gggcctccac ttcagccagg aggacgctcc agatgaaatg ggtaagtaca    1860
tcaagagctt cgtggagcgc gtgctgaaga acgagcagta atgtacaagt aaagcggccg    1920
cgactctaga tcataatcag ccataccaca tttgtagagg tttttacttgc tttaaaaaac    1980 ctcccacacc tcccctgaa cctgaaacat aaaatgaatg caattgttgt tgttaacttg    2040
tttattgcag cttataatgg ttacaaataa agcaatagca tcacaaattt cacaaataaa    2100
gcattttttt cactgcattc tagttgtggt ttgtccaaac tcatcaatgt atcttaaggc    2160
gggaattgat ctaggaaccc ctagtgatgg agttggccac tccctctctg cgcgctcgct    2220
cgctcactga ggccgcccgg gcaaagcccg ggcgtcgggc gacctttggt cgcccggcct    2280
cagtgagcga gcgagcgcgc agagagggag tggccaaccc cccccccccc ccccggcga    2340 ttctcttgtt tgctccagac tctcaggcaa tgacctgata gcctttgtag agacctctca    2400
aaaatagcta ccctctccgg catgaattta tcagctagaa cggttgaata tcatattgat    2460
ggtgatttga ctgtctccgg cctttctcac ccgtttgaat cttaacctac acattactca    2520
ggcattgcat ttaaaatata tgagggttct aaaaattttt atccttgcgt tgaaataaag    2580
gcttctcccg caaaagtatt acagggtcat aatgttttg gtacaaccga tttagcttta    2640
tgctctgagg ctttattgct taattttgct aattctttgc cttgcctgta tgatttattg    2700
gatgttggaa tcgcctgatg cggtattttc tccttacgca tctgtgcggt atttcacacc    2760
gcatatggtg cactctcagt acaatctgct ctgatgccgc atagttaagc cagccccgac    2820
acccgccaac acccgctgac gcgccctgac gggcttgtct gctcccggca tccgcttaca    2880
gacaagctgt gaccgtctcc gggagctgca tgtgtcagag gttttcaccg tcatcaccga    2940
aacgcgcgag acgaaagggc ctcgtgatac gcctattttt ataggttaat gtcatgataa    3000
taatggtttc ttagacgtca ggtggcactt ttcggggaaa tgtgcgcgga acccctattt    3060 gtttatttt ctaaatacat tcaaatatgt atccgctcat gagacaataa ccctgataaa    3120
tgcttcaata atattgaaaa aggaagagta tgagtattca acatttccgt gtcgccctta    3180
ttcccttttt tgcggcattt tgccttcctg tttttgctca cccagaaacg ctggtgaaag    3240
taaaagatgc tgaagatcag ttgggtgcac gagtgggtta tcgaactg gatctcaaca    3300 gcggtaagat ccttgagagt tttcgccccg aagaacgttt tccaatgatg agcacttta    3360 aagttctgct atgtggcgcg gtattatccc gtattgacgc cgggcaagag caactcggtc    3420
gccgcataca ctattctcag aatgacttgg ttgagtactc accagtcaca gaaaagcatc    3480
ttacggatgg catgacagta agagaattat gcagtgctgc cataaccatg agtgataaca    3540
```

```
ctgcggccaa cttacttctg acaacgatcg gaggaccgaa ggagctaacc gcttttttgc    3600
acaacatggg ggatcatgta actcgccttg atcgttggga accggagctg aatgaagcca    3660
taccaaacga cgagcgtgac accacgatgc ctgtagcaat ggcaacaacg ttgcgcaaac    3720
tattaactgg cgaactactt actctagctt cccggcaaca attaatagac tggatggagg    3780
cggataaagt tgcaggacca cttctgcgct cggcccttcc ggctggctgg tttattgctg    3840
ataaatctgg agccggtgag cgtgggtctc gcggtatcat tgcagcactg gggccagatg    3900
gtaagccctc ccgtatcgta gttatctaca cgacgggag tcaggcaact atggatgaac    3960
gaaatagaca gatcgctgag ataggtgcct cactgattaa gcattggtaa ctgtcagacc    4020
aagtttactc atatatactt tagattgatt taaaacttca ttttaatttt aaaaggatct    4080
aggtgaagat cctttttgat aatctcatga ccaaaatccc ttaacgtgag ttttcgttcc    4140
actgagcgtc agacccgta gaaaagatca aaggatcttc ttgagatcct ttttttctgc    4200
gcgtaatctg ctgcttgcaa acaaaaaaac caccgctacc agcggtggtt tgtttgccgg    4260
atcaagagct accaactctt tttccgaagg taactggctt cagcagagcg cagataccaa    4320
atactgttct tctagtgtag ccgtagttag gccaccactt caagaactct gtagcaccgc    4380
ctacatacct cgctctgcta atcctgttac cagtggctgc tgccagtggc gataagtcgt    4440
gtcttaccgg gttggactca agacgatagt taccggataa ggcgcagcgg tcgggctgaa    4500
cggggggttc gtgcacacag cccagcttgg agcgaacgac ctacaccgaa ctgagatacc    4560
tacagcgtga gctatgagaa agcgccacgc ttcccgaagg gagaaaggcg gacaggtatc    4620
cggtaagcgg cagggtcgga acaggagagc gcacgaggga gcttccaggg ggaaacgcct    4680
ggtatcttta tagtcctgtc gggtttcgcc acctctgact tgagcgtcga ttttttgtgat    4740 gctcgtcagg gggcggagc ctatggaaaa acgccagcaa cgcggccttt ttacggttcc    4800
tggccttttg ctggcctttt gctcacatgt tctttcctgc gttatcccct gattctgtgg    4860
ataaccgtat taccgccttt gagtgagctg ataccgctcg ccgcagccga acgaccgagc    4920
gcagcgagtc agtgagcgag gaagcggaag agcgcccaat acgcaaaccg cctctccccg    4980
cgcgttggcc gattcattaa tgcagctggc gtaatagcga agaggcccgc accgatcgcc    5040
cttcccaaca gttgcgcagc ctgaatggcg aatggcgatt ccgttgcaat ggctggcggt    5100
aatattgttc tggatattac cagcaaggcc gatagtttga gttcttctac tcaggcaagt    5160
gatgttatta ctaatcaaag aagtattgcg acaacggtta atttgcgtga tggacagact    5220
cttttactcg gtggcctcac tgattataaa aacacttctc aggattctgg cgtaccgttc    5280
ctgtctaaaa tccctttaat cggcctcctg tttagctccc gctctgattc taacgaggaa    5340
agcacgttat acgtgctcgt caaagcaacc atagtacgcg ccctgtagcg gcgcattaag    5400
cgcggcgggt gtggtggtta cgcgcagcgt gaccgctaca cttgccagcg ccctagcgcc    5460
cgctcctttc gctttcttcc cttcctttct cgccacgttc gccggctttc cccgtcaagc    5520
tctaaatcgg gggctccctt tagggttccg atttagtgct ttacggcacc tcgaccccaa    5580
aaaacttgat tagggtgatg gttcacgtag tgggccatcg ccctgataga cggtttttcg    5640
ccctttgacg ttggagtcca cgttctttaa tagtggactc ttgttccaaa ctggaacaac    5700
actcaaccct atctcggtct attctttga tttataaggg attttgccga tttcggccta    5760
ttggttaaaa aatgagctga tttaacaaaa atttaacgcg aattttaaca aaatattaac    5820
gcttacaatt taaatatttg cttatacaat cttcctgttt ttggggcttt tctgattatc    5880
```

```
aaccggggta catatgattg acatgctagt tttacgatta ccgttcatcg cc        5932
```

<210> SEQ ID NO 20
<211> LENGTH: 107
<212> TYPE: DNA
<213> ORGANISM: Artificial Sequence
<220> FEATURE:
<221> NAME/KEY: source
<222> LOCATION: 1..107
<223> OTHER INFORMATION: /mol_type="DNA"
    /note="recognition site for micro RNA 122"
    /organism="Artificial Sequence"

<400> SEQUENCE: 20

```
gtaatctaga tcgcgaacaa acaccattgt cacactccag tatacacaaa caccattgtc    60
acactccaga tatcacaaac accattgtca cactccaagg cctggct                 107
```

<210> SEQ ID NO 21
<211> LENGTH: 544
<212> TYPE: DNA
<213> ORGANISM: Artificial Sequence
<220> FEATURE:
<221> NAME/KEY: source
<222> LOCATION: 1..544
<223> OTHER INFORMATION: /mol_type="DNA"
    /note="Sequence of the human troponin T promoter"
    /organism="Artificial Sequence"

<400> SEQUENCE: 21

```
ctcagtccat taggagccag tagcctggaa gatgtcttta cccccagcat cagttcaagt    60
ggagcagcac ataactcttg ccctctgcct tccaagattc tggtgctgag acttatggag   120
tgtcttggag gttgccttct gcccccaac cctgctccca gctggccctc ccaggcctgg    180
gttgctggcc tctgctttat caggattctc aagagggaca gctggtttat gttgcatgac   240
tgttccctgc atatctgctc tggttttaaa tagcttatct gagcagctgg aggaccacat   300
gggcttatat ggcgtggggt acatgttcct gtagccttgt ccctggcacc tgccaaaata   360
gcagccaaca ccccccaccc ccaccgccat cccctgccc acccgtccc ctgtcgcaca     420 ttcctccctc cgcagggctg gctcaccagg cccagccca catgcctgct taaagccctc    480
tccatcctct gcctcaccca gtcccaagct ttattgcggt agtttatcac agttaaattg    540
ctaa                                                                544
```

<210> SEQ ID NO 22
<211> LENGTH: 828
<212> TYPE: DNA
<213> ORGANISM: Artificial Sequence
<220> FEATURE:
<221> NAME/KEY: source
<222> LOCATION: 1..828
<223> OTHER INFORMATION: /mol_type="DNA"
    /note="CMVMLC260 Promoter"
    /organism="Artificial Sequence"

<400> SEQUENCE: 22

```
gcggccgctt cgagctcgcc cgacattgat tattgactag ttattaatag taatcaatta    60
cggggtcatt agttcatagc ccatatatgg agttccgcgt tacataactt acggtaaatg   120
gcccgcctgg ctgaccgccc aacgaccccc gcccattgac gtcaataatg acgtatgttc   180
ccatagtaac gccaataggg actttccatt gacgtcaatg ggtggagtat ttacggtaaa   240
ctgcccactt ggcagtacat caagtgtatc atatgccaag tacgcccct attgacgtca    300 atgacggtaa atggcccgcc tggcattatg cccagtacat gaccttatgg gactttccta   360
```

```
cttggcagta catctacgta ttagtcatcg ctattaccat ggtgatgcgg ttttggcagt      420
acatcaatgg gcgtggatag cggtttgact cacggggatt tccaagtctc caccccattg      480
acgtcaatgg gagtttgttt tggcaccaaa atcaacggga ctttccaaaa tgtcgtaaca      540
actccgcccc atgcggccgc tctaggaccc agagcacaga gcatcgttcc caggccaggc      600
cccagccact gtctctttaa ccttgaaggc atttttgggt ctcacgtgtc cacccaggcg      660
ggtgtcggac tttgaacggc tcttacttca gaagaacggc atggggtggg ggggcttagg      720
tggcctctgc ctcacctaca actgccaaaa gtggtcatgg ggttattttt aaccccaggg      780
aagaggtatt tattgttcca cagcaggggc cggccagcag gctccttg                   828
```

ABHD5 AND PARTIAL HDAC4 FRAGMENTS AND VARIANTS AS A THERAPEUTIC APPROACH FOR THE TREATMENT OF CARDIOVASCULAR DISEASES

CROSS REFERENCE TO RELATED APPLICATIONS

This application is a 371 national stage of International Application No. PCT/EP2014/053042, filed on Feb. 17, 2014, and claims the benefit of U.S. Provisional Application No. 61/765,440, filed Feb. 15, 2013, the disclosures of which are herein incorporated by reference in their entirety.

REFERENCE TO SEQUENCE LISTING

The instant application contains a Sequence Listing which has been submitted electronically in ASCII format and is hereby incorporated by reference in its entirety. Said ASCII copy, created on Aug. 6, 2015, is named 116023_1_Sequence_Listing.txt and is 78,641 bytes in size.

FIELD OF THE INVENTION

The present invention relates to Abhydrolase containing domain 5 (ABHD5) and N-terminal fragments of HDAC4 (HDAC4-NT) and variants of the aforementioned peptides for the treatment and prevention of heart failure. The present invention further provides vectors for the cardiomyocyte-specific expression of said peptides and a test system comprising ABHD5 for the identification of novel compounds which are useful for the treatment of heart failure.

BACKGROUND OF THE INVENTION

Sustained catecholaminergic stress is known to promote heart failure (Cohn et al., 1984 "Plasma Norepinephrine as a Guide to Prognosis in Patients with Chronic Congestive Heart Failure" New England Journal of Medicine, 311: 819-823). In contrast to this, short-term catecholaminergic stimulation (e.g. by physical exercise) promotes cardiac health (Keteyian et al, 2010 "Clinical Role of Exercise Training in the Management of Patients with Chronic Heart Failure" Journal of Cardiopulmonary Rehabilitation and Prevention, 30:67-76). Thus, there appear to be different signaling pathways downstream of the β-adrenergic receptor mediating cardioprotective and pathophysiological effects of β-adrenergic receptor stimulation. One consequence of sustained catecholaminergic stress is myocardial remodeling which causes or exacerbates heart failure. Thus, therapeutic means for influencing said signaling pathways are desirable.

Full-length histone deacetylase 4 (HDAC4) is proteolytically processed by a previously unknown enzyme yielding an N-terminal fragment (HDAC4-NT) comprising 201 amino acids. In vitro, HDAC4-NT selectively represses myocyte enhancer factor 2 (MEF2) (Backs et al., 2011, "Selective repression of MEF2 Activity by PKA-dependent Proteolysis of HDAC4", Journal of Cell Biology, 195: 403-415).

Abhydrolase containing domain 5 (ABHD5, also known as "comparative gene identification-58" (CGI-58)) is a protein which has been previously known to be involved in lipid metabolism (Grannemann et al., 2009 "Perilipin controls Lipolysis by regulating the Interactions of AB-hydrolase Containing 5 (Abhd5) and Adipose Triglyceride Lipase (Atgl)", The Journal of Biological Chemistry 284: 34538-34544). Mutations of ABHD5 cause the Chanarin-Dorfman syndrome, a rare genetic disease characterized by excessive accumulation of triacylglycerol in multiple tissues (Lass et al., 2006 "Adipose triglyceride lipase-mediated lipolysis of cellular fat stores is activated by CGI-58 and defective in Chanarin-Dorfman Syndrome" Cell Metabolism 3: 309-319). It has not been implicated in the regulation of cardiac remodeling.

Thus, the problem underlying the present invention can be viewed as the provision of novel means and methods for the treatment and prevention of heart failure.

BRIEF SUMMARY OF THE INVENTION

In a first aspect, the present invention relates to abhydrolase containing domain 5 (ABHD5) or a variant thereof for use as a medicament.

In another aspect, the present invention relates to ABHD5 or a variant thereof for use in the treatment or prevention of heart failure.

In yet another aspect, the present invention relates to a nucleic acid encoding ABHD5 or a variant thereof for use as a medicament.

In yet another aspect, the present invention relates to a nucleic acid encoding ABHD5 or a variant thereof for use in the treatment or prevention of heart failure.

In yet another aspect, the present invention relates to a vector comprising a nucleic acid encoding ABHD5 or a variant thereof.

In yet another aspect, the present invention relates to a vector comprising a nucleic acid encoding ABHD5 or a variant thereof for use as a medicament.

In yet another aspect, the present invention relates to a vector comprising a nucleic acid encoding ABHD5 or a variant thereof for use in the treatment or prevention of heart failure.

In yet another embodiment, the present invention relates to an elongated and/or multimerized variant of the N-terminal fragment of histone deacetylase 4 (HDAC4-NT).

In yet another embodiment, the present invention relates to HDAC4-NT or a variant thereof for use as a medicament.

In yet another embodiment, the present invention relates to HDAC4-NT or a variant thereof for use in the treatment or prevention of heart failure.

In yet another aspect, the present invention relates to a nucleic acid encoding an elongated and/or multimerized variant of HDAC-NT.

In yet another aspect, the present invention relates to a nucleic acid encoding HDAC4-NT or a variant thereof for use as a medicament.

In yet another aspect, the present invention relates to a nucleic acid encoding HDAC4-NT or a variant thereof for use in the treatment or prevention of heart failure.

In yet another aspect, the present invention relates to a vector comprising nucleic acid encoding HDAC4-NT or a variant thereof.

In yet another aspect, the present invention relates to a nucleic acid encoding HDAC4-NT or a variant thereof for use as a medicament.

In yet another aspect, the present invention relates to a vector comprising a nucleic acid encoding HDAC4-NT or a variant thereof for use in the treatment or prevention of heart failure.

In yet another aspect, the present invention relates to a method for identifying a compound which modulates the activity and/or localization of ABHD5 or a variant thereof comprising the steps of a) contacting a test system comprising ABHD5 or a variant thereof with a candidate compound;
b) determining whether the candidate compound modulates the activity and/or localization of ABHD5 or the variant thereof;
c) identifying the compound as a compound which modulating the activity and/or localization of ABHD5 based on the comparison of the activity of ABHD5 or the variant thereof in the test system comprising the candidate compound and the activity of ABHD or the variant thereof determined in a control in step b).

In yet another aspect, the present invention relates to the use of ABHD5 for identifying a compound which suppresses myocardial remodeling.

BRIEF DESCRIPTION OF THE DRAWINGS

FIG. 8: (A) Overexpression of ABHD5 leads to proteolysis of HDAC4. Flag tagged HDAC4 was overexpressed in neonatal rat cardiomycytes with ABHD5, Western blot was performed with an antibody, recognizing Flag. Successful overexpression of ABHD5-GFP was confirmed with a western blot, detecting GFP. (B) HDAC4 and ABHD5 were cloned into a plasmid bearing constitutively active promoter (pNOP) and Galactose inducible promoter (pGAL) respectively. By overexpression either together or with backbone vector in Saccharomyces cerevisiae we found cleavage of HDAC4, confirmed by westernblot analysis. This experiment confirms that ABHD5 cleaves HDAC4 directly without the recruitment of factors only present in mammalian cells. (C) By co-treatment of mice with insulin and a beta receptor agonist (ISO) we found an increase of ABHD5 expression and consequently an increase of endogenous HDAC4 proteolysis. We show here exemplary western blots, performed with antibodies recognizing endogenous N-terminal HDAC4 and endogenous ABHD5. Westernblot against GAPDH confirmed equally protein loading.

DETAILED DESCRIPTION OF THE INVENTION

Figure 1A:
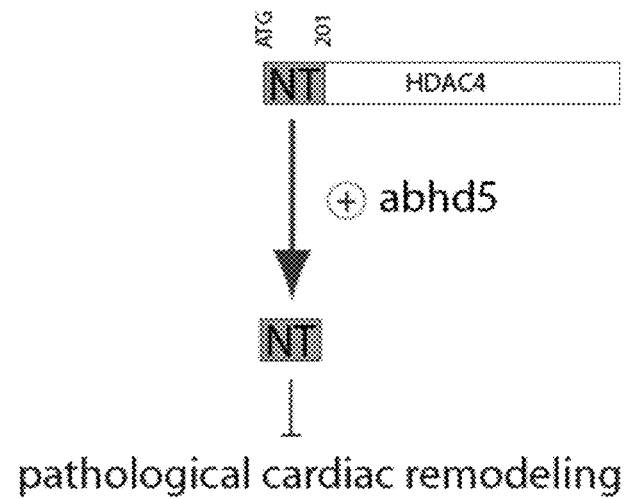
FIG. 1: AAV-9 is an example as an use in vivo. (A) gain of function of the protease abhd5 to increase the quantity of cardioprotective HDAC4-NT. (B) Genetreansfer of HDAC4-NT, optimized HDAC4-NT or HDAC4-NT related constructs via adeno associated virus (AAV). NT: N-terminus; abhd5: 1-acylglycerol-3-phosphate O-acyltransferase.
Figure 1B:
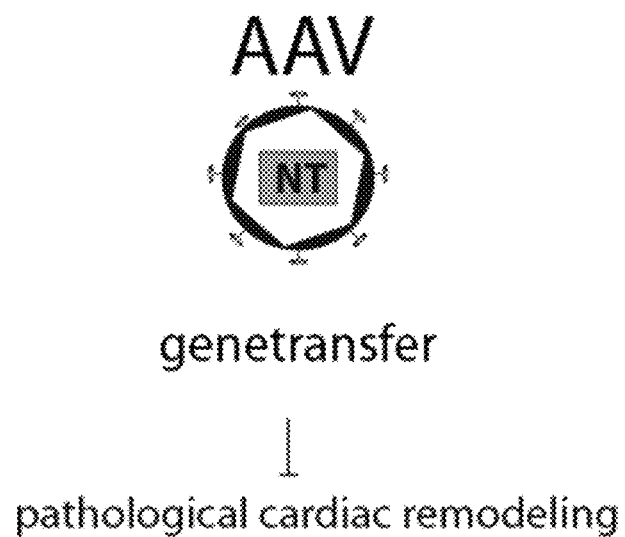

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IU-PAC Recommendations)", H. G. W. Leuenberger, B. Nagel, and H. Kölbl, Eds., Helvetica Chimica Acta, CH-4010 Basel, Switzerland, (1995).

To practice the present invention, unless otherwise indicated, conventional methods of chemistry, biochemistry, cell biology, and recombinant DNA techniques are employed which are explained in the literature in the field (cf., e.g., *Molecular Cloning: A Laboratory Manual, 2$^{nd}$ Edition*, J. Sambrook et al. eds., Cold Spring Harbor Laboratory Press, Cold Spring Harbor 1989). Furthermore, conventional methods of clinical cardiology are employed which are also explained in the literature in the field (cf., e.g., *Practical Methods in Cardiovascular Research*, S. Dhein et al. eds., Springer Verlag Berlin Heidelberg, 2005).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. As used in this specification and the appended claims, the singular forms "a", "an", and "the" include plural referents, unless the content clearly dictates otherwise.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

ABHD5 and Variants Thereof

It has been surprisingly found in the study underlying the present invention that inhibition of expression of ABHD5 prevents the proteolytic cleavage of full-length HDAC4, thus generating HDAC4-NT. Based on sequence analysis, it is likely that ABHD5 is a serine protease which cleaves HDAC4. Based on this finding, the ABHD5 can be used for generating HDAC4-NT in vivo, thus protecting the myocardium from heart failure.

Therefore, the present invention relates to abhydrolase containing domain 5 (ABHD5) or a variant thereof for use as a medicament.

In another embodiment, the present invention relates to ABHD5 or a variant thereof for use in the treatment or prevention of heart failure.

The term "ABHD5" relates to a polypeptide having an amino acid sequence as defined by one of the sequences SEQ ID NO: 1 to 5 or a variant thereof. Preferably, ABDH5 has an amino acid as defined by SEQ ID NO: 1 (human ABDH5) or a variant thereof.

"Variants" are preferably N-terminally and/or C-terminally truncated variants, amino acid substitution or deletion variants, or prolonged variants of the sequences of SEQ ID NO: 1 to 5. Variants comprise furthermore an amino acid sequence comprising modified amino acid(s), unnatural amino acid(s) or peptidomimetic(s) or further compounds which can mimic a peptide backbone/structure. Preferably, variants are selected from C-terminally truncated variants of SEQ ID NO.: 1 to 5; amino acid substitution or deletion variants; variants comprising modified amino acid(s), unnatural amino acid(s) or peptidomimetic(s) or further compounds which can mimic a peptide backbone/structure.

Deletion variants are, preferably, characterized by C-terminal deletion of up to 1, 2, 3, 4, 5, 10, 15, 20, 25 or 30 amino acids. Independently of the presence or absence of C-terminal deletions further preferred deletion variants are characterized by N-terminal deletion of up to 1, 2, 3, 4, 5, 10, 15, 20, 25 or 30 amino acids.

The term "ABDH5 variants" preferably includes proteins which have at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity over the entire length of the protein according to SEQ ID NO: 1 to 5 or proteins based on SEQ ID NO: 1 to 5 carrying above outlined N- and/or C-terminal deletions using the best sequence alignment and/or over the region of the best sequence alignment, wherein the best sequence alignment is obtainable with art known tools, e.g. Align, using standard settings, preferably EMBOSS::needle, Matrix: Blosum62, Gap Open 10.0, Gap Extend 0.5, with the amino acid sequence set forth in SEQ ID NOs: 1, 2, 3, 4, or 5. It is preferred that when a given ABDH5 variant is aligned with a ABDH5 according to SEQ ID NO:1, 2, 3, 4 or 5 that alignment will be over the entire length of the two proteins and, thus, that the alignment score will be determined on this basis.

In especially preferred deletion variants, the first 29 or, more preferably, the first 31 amino at the N-terminus are deleted. Human ABHD5 comprises tryptophan residues at positions 19, 23 and 27. Rat and mouse ABHD5 comprise tryptophan residues at positions 21, 25 and 29. Said tryptophan residues are responsible for the binding of ABHD5 to lipid droplets. Deletion of these tryptophan residues creates a variant of ABHD5 which has less affinity to lipid droplets. Thus, such deletion variants move more easily to the nucleus and the cytosol where they mediate cleavage of full-length HDAC4 yielding HDAC4-NT.

Deletions in further preferred deletion variants are designed to remove only the first or only the first and second tryptophan residues. Thus, these deletion variants have a lower affinity to lipid droplets as compared to full-length ABHD5 but higher affinity as compared to deletion variants missing the first 27 or 30 amino acids.

Preferred substitution variants are generated by substituting up to 1, 2, 3, 4, 5, 10, 15, 20, 25 or 30 amino acids against natural amino acids, unnatural amino acids or peptidomimetics. Preferably, the amino acids of the wild type protein or a deletion variant thereof are substituted for natural amino acids . . . more preferably, said substitutions are conservative substitutions.

A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases, where two or more amino acid sequences differ from each other by conservative substitutions, the number of substitutions may be adjusted upwards to correct for the conservative nature of the substitution. Thus, in the case of conservative amino acid substitutions up to 40, up to 50 or even up to 70 amino acids may be substituted. Examples of groups of amino acids that have side chains with similar chemical properties include:
1) aliphatic side chains: glycine, alanine, valine, leucine and isoleucine;
2) aliphatic-hydroxyl side chains: serine and threonine;
3) amide-containing side chains: asparagine and glutamine;
4) aromatic side chains: phenylalanine, tyrosine, and tryptophan;
5) basic side chains: lysine, arginine, and histidine;
6) acidic side chains: aspartate and glutamate, and
7) sulfur-containing side chains: cysteine and methionine.

Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet G. H. et al., 1992 "Exhaustive matching of the entire protein sequence database." *Science* 1992, 256:1443-1445. A "moderately conservative" replacement is any change having a non-negative value in the PAM250 log-likelihood matrix.

In especially preferred substitution variants preferably 1, more preferably 2 and most preferably 3 of the tryptophan residues mentioned above (positions 19, 23 and 27 in human ABHD5; positions 22, 26 and 30 in mouse or rat ABHD5) are substituted by a different amino acid. Preferably, said substitution is not a conservative substitution and more preferably, the amino acid which takes the place of tryptophan is alanine.

In one preferred embodiment, positions 19 and 23 of human ABHAD5 or positions 22 and 26 of rat ABHD5 are substituted, preferably with alanine.

In another preferred embodiment, positions 23 and 27 of human ABHAD5 or positions 26 and 30 of rat ABHD5 are substituted, preferably with alanine.

A "variant" as defined above is, preferably, a functional variant. A functional variant is a variant of the wild type ADHD5 as described above which retains its capability to mediate cleavage of full-length HDAC4 in vitro and, preferably, in vivo. Preferably, the ADHD5 variant has at least 50% of the capability of ADHD5 according to SEQ ID NO: 1 to 5, preferably of SEQ I NO: 1 to 5 mediate cleavage of full-length HDAC4 in vitro and, preferably, in vivo, more preferably at least 60%, 70%, 80%, 90%, 95% or 100% of this activity.

An assay for testing whether a variant of ABDH5 is still functional can be based on a cell line which does not express ABDH5 due to a knock out. As described in the examples, inhibition of ABHD5 expression inhibits cleavage of HDAC4. If the cells are then transfected with an expression vector encoding the variant of ABHD5 to be tested, a functional variant restores the cell's capability of generating HDAC4-NT from full-length HDAC4, while a non-functional variant does not. Alternatively, the variant of ABDH5 may be administered to the cells as a peptide.

An even more preferred assay can be conducted in vitro: Since ABDH5 is a putative protease, functional variants of ABDH5 are able to cleave full-length HDAC4 if the required ions and cofactors are present.

Heart Failure

The term "heart failure" as used in the present application refers to any conditions characterized by the inability of the heart to pump a sufficient amount of blood to meet the body's oxygen demand.

Heart failure may affect the right ventricle, the left ventricle or both ventricles. The present invention relates to the treatment or prevention of all of the aforementioned types of heart failure and all degrees of heart failure as set forth below.

The typical symptom experienced by a patient suffering from left-ventricular heart failure is shortness of breath (dyspnea). In mild forms of heart failure, the patient is not limited in ordinary physical activity but experiences dyspnea during periods of increased physical exercise. In more severe cases of heart failure, dyspnea is experienced during ordinary or even light physical activity. In the most severe cases, the patient even experiences dyspnea at rest. The typical symptom of right ventricular heart failure is the congestion of systemic capillaries leading to the accumulation of fluids in various parts of the body. Fluid accumulates in the feet and legs (in people standing up) or in the sacral area (in people lying down). In severe cases fluid accumulates in the abdominal cavity and/or the liver.

Heart failure may be divided into inherited and acquired forms of the disease. Inherited forms of the disease include hypertrophic cardiomyopathy, dilated cardiomyopathy, arrhythmogenic right ventricular cardiomyopathy, isolated ventricular non-compaction and mitochondrial myopathy. Acquired heart failure is typically caused by coronary artery disease, arterial hypertension, loss of viable myocardium due to myocardial infarction, cigarette smoking, obesity, diabetes, metabolic syndrome, kidney disease, environmental stress, depressive or mood disorders, lipid storage disease, cancer, chronic inflammation, postpartal cardiomyopathy, stress induced cardiomyopathy, transient cardiac dysfunction or valvular heart disease. It is particularly preferred that acquired cardiomyopathies are treated, in particular postpartal cardiomyopathy, stress induced cardiomyopathy, transient cardiac dysfunction.

The means and methods of the present invention are suited for the treatment of all the aforementioned types of heart failure.

Heart failure is caused or accompanied by myocardial remodeling. In myocardial remodeling, terminally differentiated cardiomyocytes increase in size in order to increase the contractility of the myocardium. However, this leads to increasing stiffness of the heart and concomitantly to difficulties in filling the ventricles during diastole. Moreover, the ventricles enlarge contributing to a more spherical form of the heart. This spherical shape of the heart decreases the stroke volume. Since myocardial remodeling tends to decrease myocardial output rather than increasing it, the process of myocardial remodeling causes and exacerbates heart failure.

As a consequence of myocardial remodeling, the risk of cardiac dysrhythmia increases. The term "cardiac dysrhythmia" refers to all types abnormal electric activity of the myocardium. Preferably, cardiac dysrhythmia is tachycardia (pathologically increased heart beat) or bradycardia (pathologically decreased heart beat). Cardiac dysrhythmia may originate from the atria or the ventricles. Particularly relevant types of dysrhythmia are areal fibrillation and ventricular tachycardia.

Therefore, the means and methods of the present invention which suppress or reverse the process of myocardial remodeling during heart failure are well suited for the treatment or prevention of myocardial remodeling, thus increasing cardiac output and decreasing the risk of complications of cardiac remodeling, particularly cardiac dysrhythmia as defined above.

The success of the treatment according to the present invention may be verified by echocardiography or magnetic resonance imaging. Moreover, decreasing levels of natriuretic peptides, particularly nT-proBNP after onset of treatment indicate that the treatment is successful.

Patient

The patient receiving the pharmaceutical compounds and pharmaceutical compositions disclosed in the present application is preferably a primate, rodent, pig, sheep, cow or goat. The rodent is, preferably, a rat and more preferably a mouse. The primate is, preferably, a human, chimpanzee or macaque. Most preferably, the patient is a human.

Preferably, the patient suffers from heart failure.

Treatment

As used herein, "treat", "treating" or "treatment" of a heart failure means refers to at least one of the following: (a) reducing the severity of heart failure, (b) limiting or preventing the symptoms typical for heart failure, (c) reversing myocardial remodeling, (d) preventing further progress of myocardial remodeling, and (e) decreasing the likelihood of the negative consequences of myocardial remodeling described above. Preferably, a patient to be treated already suffers from heart failure and/or myocardial remodeling.

As used herein, "prevent", "preventing" or "prevention" refer to the inhibition of the onset of heart failure and/or myocardial remodeling in a patient not yet suffering from the aforementioned disorders. Thus, a patient receiving preventive treatment is healthy with respect to the disorder to be prevented by said treatment. In a preferred embodiment of the present invention, the patient suffers from heart failure but does not yet show signs and symptoms of myocardial remodeling.

It is understood by the person skilled in the art that "treatment" or prevention" may not be successful in every patient receiving the pharmaceutical compounds or composition of the present invention. However, the terms "treatment" and "prevention" require that a significant proportion of patient benefits from said treatment.

In patients suffering from primary heart failure as defined above, treatment according to the present invention preferably cures heart failure because it removes or alleviates the underlying cause.

In patients suffering from secondary heart failure as defined above, the treatment according to the present invention preferably decreases the speed of progression of heart failure or even stops progression of heart failure completely.

Nucleic Acid

In yet another aspect, the present invention relates to a nucleic acid encoding ABHD5 or a variant thereof for use as a medicament.

In yet another aspect, the present invention relates to a nucleic acid encoding ABHD5 or a variant thereof for use in the treatment or prevention of heart failure.

The term "nucleic acid" refers to a polymeric macromolecule made from nucleotide monomers. Nucleotide monomers are composed of a nucleobase, a five-carbon sugar (such as but not limited to ribose or 2'-deoxyribose), and one to three phosphate groups. Typically, a polynucleotide is formed through phosphodiester bonds between the individual nucleotide monomers. In the context of the present invention preferred nucleic acid molecules include but are not limited to ribonucleic acid (RNA) and deoxyribonucleic acid (DNA). Moreover, the term "polynucleotide" also includes artificial analogs of DNA or RNA, such as peptide nucleic acid (PNA).

The nucleic acid of the present invention encodes ABHD5 or a variant thereof. Since the genetic code is degenerated, i.e. each amino acid is encoded by more than one nucleic acid, each peptide or its variant may be encoded by a multiplicity of different nucleic acid sequences.

Preferably, the nucleic acid encoding ABHD5 is selected from the group consisting of SEQ ID NOs: 6, 7, 8, 9 and 10.

More preferably, the nucleic acid encoding ABHD5 has a sequence as defined by SEQ ID NO: 6.

Vector

For an effective treatment of heart failure, the increase of the amount of functional ABHD5 is advantageous. The administration of ABHD5 may pose practical difficulties. Therefore, the use of expression systems which mediate expression of ABHD5 by the cardiomyocytes of the patient are a solution for the problem underlying the present invention.

Thus, in yet another embodiment, the present invention relates to a vector comprising a nucleic acid encoding ABHD5 or a variant thereof.

In yet another embodiment, the present invention relates to a vector comprising a nucleic acid encoding ABHD5 or a variant thereof for use as a medicament.

In yet another embodiment, the present invention relates to a vector comprising a nucleic acid encoding ABHD5 or a variant thereof for use in the treatment or prevention of heart failure.

As used herein, the term "vector" refers to at least one nucleic acid or to a mixture of at least one nucleic acid and at least one protein which is capable of introducing the nucleic acid comprised therein into a cell. At least one nucleic acid comprised by the vector consists of or comprises at least one nucleic acid encoding ABHD5 or a variant thereof. In addition to the nucleic acid consisting of or comprising the nucleic acid encoding ABHD5 or the variant thereof, additional nucleic acids and/or polypeptides may be introduced into the cell. The addition of additional nucleic acids and/or polypeptides is especially preferred if said additional nucleic acids and/or polypeptides are required to introduce the nucleic acid encoding ABHD5 or the variant thereof into the cell.

In the context of the present invention it is preferred that ABHD5 or the variant thereof is expressed within the cell upon introduction of the vector or vectors. Examples of suitable vectors include but are not limited to plasmids, cosmids, phages, viruses or artificial chromosomes.

In preferred embodiments, the vector is selected from the group consisting of plasmids, cosmids, phages, viruses, and artificial chromosomes. More preferably, a vector suitable for practicing the present invention is a phage vector, preferably lambda phage and filamentous phage vectors, or a viral vector.

Preferred viral vectors are based on naturally occurring vectors, which are modified to be replication incompetent also referred to as non-replicating. Non-replicating viruses require the provision of proteins in trans for replication. Typically those proteins are stably or transiently expressed in a viral producer cell line, thereby allowing replication of the virus. The viral vectors are, thus, preferably infectious and non-replicating. The skilled person is aware of how to render various viruses replication incompetent.

In a preferred embodiment of the present invention the vector is selected from the group consisting of adenovirus vectors, adeno-associated virus (AAV) vectors (e.g., AAV type 6, type 1, type 5, type 9 and type 2), alphavirus vectors (e.g., Venezuelan equine encephalitis virus (VEE), sindbis virus (SIN), semliki forest virus (SFV), and VEE-SIN chimeras), herpes virus vectors (e.g. vectors derived from cytomegaloviruses, like rhesus cytomegalovirus (RhCMV) (14)), arena virus vectors (e.g. lymphocytic choriomeningitis virus (LCMV) vectors (15)), measles virus vectors, pox virus vectors (e.g., vaccinia virus, modified vaccinia virus Ankara (MVA), NYVAC (derived from the Copenhagen strain of vaccinia), and avipox vectors: canarypox (ALVAC) and fowlpox (FPV) vectors), vesicular stomatitis virus vectors, retrovirus, lentivirus, viral like particles, and bacterial spores.

The most preferred vector is an adenovirus, more preferably adeno associated virus (AAV) type 1, type 6 or type 9. For use in humans, AAV types 1 or 6 are preferred, for use in mice AAV type 9.

An especially preferred vector given in SEQ ID NO: 18. Also preferred is a vector as defined by SEQ ID NO: 19. Said sequences comprise HDAC4-NT or luciferase instead of a ABHD5. However, the exchange of these inserts for ABHD5 is easily accomplished.

To direct expression of ABHD5 or the variant thereof, the nucleic acid encoding it is operationally linked to an internal promoter and/or enhancer that is recognized by the transcriptional machinery of the cell. Suitable promoters may be derived from the genome of mammalian cells (e. g., MHCII promoter, EF1alpha promoter) or from mammalian viruses (e.g., the cytomegalovirus promoter, the spleen focus-forming virus SFFV promoter). Especially preferred are promoters which enable the expression of the above-mentioned gene in cardiomyocytes.

One preferred promoter is defined by SEQ ID NO: 22. In an especially preferred embodiment, the promoter is a human troponin promoter, more preferably the human troponin T promoter, as this promoter is especially well suited for cardiomyocyte-specific expression of transgenes. Preferably, the human troponin T promoter has a nucleic acid sequence as defined by SEQ ID NO: 21.

In another preferred embodiment, the vector encodes a recognition site for micro-RNA 122 between the coding sequence of the HDAC4, ABHD5 or their variants and the terminator sequence so that said recognition site becomes part of the transcript which also encodes HDAC4, ABHD5 or a variant thereof produced from this vector. Since micro-RNA 122 is found in many types of cells but not in cardiomyocytes, said recognition site causes breakdown of the mRNA in those types of cells where micro-RNA 122 is present, thus preventing translation of the transcript. Preferably the recognition site for micro-RNA 122 has a nucleic acid sequence as defined by SEQ ID NO: 20.

Since the two elements described above are advantageous for the cardiomyocyte-specific expression of many other peptides besides HDAC4-NT and ABHD5, the present invention relates in a further embodiment to the use of a recognition site for micro-RNA 122 for the cardiomyocyte-specific expression of transgenes. Preferably, said recognition site has a nucleic acid sequence as defined by SEQ ID NO: 20.

In yet another embodiment, the present invention relates to the use of a combination of the human troponin promoter and the recognition site for micro-RNA 122 for the cardiomyocyte-specific expression of transgenes. Preferably, said recognition site has a nucleic acid sequence as defined by SEQ ID NO: 20.

In yet another embodiment, the present invention relates to a vector encoding a recognition site for micro-RNA 122 between the promoter and the terminator sequence so that said recognition site becomes part of the transcript which also encode HDAC4-NT or a variant thereof produced from this vector. Preferably, said recognition site has a nucleic acid sequence as defined by SEQ ID NO: 20. Preferably, the vector additionally comprises a human troponin promoter.

More preferably, the human troponin promoter controls transcription of the nucleic sequence which comprises the aforementioned recognition site for micro-RNA 122.

In a particularly preferred embodiment of the present invention, the vector comprises a human troponin T promoter as defined above and a nucleic acid sequence encoding a recognition site for micro-RNA 122 as defined above.

As used herein, "operatively linked" means incorporated into a genetic construct so that expression control sequences effectively control expression of a coding sequence of interest.

Specific initiation signals may also be required for efficient translation of coding sequences. These signals include the ATG initiation codon and adjacent sequences. Exogenous translational control signals, including the ATG initiation codon, may additionally need to be provided. One of ordinary skill in the art would readily be capable of determining this and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic.

HDAC4-NT and Variants Thereof

HDAC4-NT not just represses the transcription factor MEF2 in vitro, thus inhibiting cardiomyocyte hypertrophy (Backs et al., 2011, cited supra). The study underlying the present invention surprisingly showed that overexpression of HDAC4 by an adenoviral expression system in vivo (i) prevents myocardial remodeling, and (ii) does not cause intolerable side effects. Given the fact, that similar approaches with other peptides proved non feasible in vivo due to side effects (Czubryt et al. 2003, Proc Natl Acad Sci U.S.A. 100:1711-6), this finding was unexpected and highlights the advantages of HDAC4-NT as a therapeutic means.

Therefore, in yet another embodiment, the present invention relates to an elongated and or multimerized variant of the N-terminal fragment of histone deacetylase 4 (HDAC4-NT).

In yet another embodiment, the present invention relates to HDAC4-NT or a variant thereof for use as a medicament.

In yet another embodiment, the present invention relates to HDAC4-NT or a variant thereof for use in the treatment or prevention of heart failure.

All definitions given above for the terms "heart failure", "patient", "treatment" and "prevention" with respect to ABHD5 also apply to embodiments of the invention relating to HDAC4-NT and the variants thereof.

The term "HDAC4-NT" relates to a polypeptide having an amino acid sequence as defined by one of the sequences SEQ ID NO: 13 (human HDAC4-NT) or 14 (mouse HDAC4-NT) or a variant thereof. Preferably, HDAC4-NT has an amino acid sequence as defined by SEQ ID NO: 13 or a variant thereof.

"Variants" of HDAC4-NT are preferably N-terminally and/or C-terminally truncated variants, amino acid substitution or deletion variants, multimerized or elongated variants of the sequences defined by SEQ ID NO: 13 or 14. Variants comprise furthermore an amino acid sequence comprising modified amino acid(s), unnatural amino acid(s) or peptidomimetic(s) or further compounds which can mimic a peptide backbone/structure. Preferably, variants are selected from C-terminally truncated variants of SEQ ID NO: 13 or 14; amino acid substitution or deletion variants; variants comprising modified amino acid(s), unnatural amino acid(s) or peptidomimetic(s) or further compounds which can mimic a peptide backbone/structure.

Deletion variants are, preferably, characterized by C-terminal deletion of up to 1, 2, 3, 4, 5, 10, 15, 20, 25 or 30 amino acids. Independently of the presence or absence of C-terminal deletions further preferred deletion variants are characterized by N-terminal deletion of up to 1, 2, 3, 4, 5, 10, 15, 20, 25 or 30 amino acids. A preferred deletion variant comprises amino acid positions 2 to 201 of SEQ ID NO: 13 or 14, more preferably of SEQ ID NO: 13. This variant is also referred to as "HDAC4 2-201".

The term "HDAC4-NT variants" preferably includes proteins which have at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity over the entire length of the protein according to SEQ ID NO: 13 or 14 or proteins based on SEQ ID NO: 13 or 14 carrying above outlined N- and/or C-terminal deletions using the best sequence alignment and/or over the region of the best sequence alignment, wherein the best sequence alignment is obtainable with art known tools, e.g. Align, using standard settings, preferably EMBOSS::needle, Matrix: Blosum62, Gap Open 10.0, Gap Extend 0.5, with the amino acid sequence set forth in SEQ ID NOs: 13 or 14. It is preferred that when a given HDAC4-NT variant is aligned with a HDAC4-NT according to SEQ ID NO: 13 or 14 that alignment will be over the entire length of the two proteins and, thus, that the alignment score will be determined on this basis.

Preferably, a deletion variant retains amino acid positions 169 to 185 of SEQ ID NO: 13 as these positions are important for binding of HDAC-NT to MEF2.

Preferred substitution variants are generated by substituting up to 1, 2, 3, 4, 5, 10, 15, 20, 25 or 30 amino acids against natural amino acids, unnatural amino acids or peptidomimetics. Preferably, the amino acids of the wild type protein or a deletion variant thereof are substituted for natural amino acids, more preferably, said substitutions are conservative substitutions.

A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases, where two or more amino acid sequences differ from each other by conservative substitutions, the number of substitutions may be adjusted upwards to correct for the conservative nature of the substitution. Thus, in the case of conservative amino acid substitutions up to 40, up to 50 or even up to 70 amino acids may be substituted. Examples of groups of amino acids that have side chains with similar chemical properties include
1) aliphatic side chains: glycine, alanine, valine, leucine and isoleucine;
2) aliphatic-hydroxyl side chains: serine and threonine;
3) amide-containing side chains: asparagine and glutamine;
4) aromatic side chains: phenylalanine, tyrosine, and tryptophan;
5) basic side chains: lysine, arginine, and histidine;
6) acidic side chains: aspartate and glutamate, and
7) sulfur-containing side chains: cysteine and methionine.

Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet G. H. et al., 1992 "Exhaustive matching of the entire protein sequence database." Science 1992, 256:1443-1445. A "moderately conservative" replacement is any change having a non-negative value in the PAM250 log-likelihood matrix.

Further preferred variants of HDAC4-NT are elongated variants which comprise additional amino acids at the C-terminus. More preferred are variants which comprise amino acid positions 2 to 202, 1 to 220, 1 to 216, 1 to 212 or 1 to 208 of full-length HDAC4 as defined by SEQ ID NO: 11 (human) or 12 (mouse). Even more preferably, a variant of HDAC4-NT comprises amino acid positions 2 to 202, 1 to 208 or 1 to 220 of SEQ ID NO: 11 or 12. Most preferably, an elongated variant of HDAC4-NT comprises amino acid positions 2 to 202, 1 to 220 or 1 to 208 of SEQ ID NO: 11. It is to be understood that said elongated variants may be modified by amino acid substitutions as set forth above. The variant comprising amino acid positions 2 to 202 is also referred to as HDAC4 2-202.

In a further preferred embodiment, the variant of HDAC4-NT is a variant generated by multimerization of HDAC4-NT. A multimerized variant of HDAC4-NT is a polypeptide which comprises the amino acid sequence of HDAC4-NT or any of the variants described above not just once but in at least 2, at least 3, at least 4 or at least 5 repeats. Thus, a single polypeptide comprises more than one binding site for MEF2. It is to be understood that a multimerized variant of HDAC4-NT or any of the above-described deletion, elongation or substitution variants thereof may be generated by repeating the same amino acid sequence (homogeneous multimer) or by combining more than one of the aforementioned variants (heterogeneous multimer), thus generating a polypeptide whose repeated sequence motifs are similar but not identical In an especially preferred embodiment of the present invention, amino acid positions 1 to 201, 2 to 201, 2 to 202, 1 to 208 or 1 to 220 are multimerized. In one preferred embodiment, the multimerization is homogeneous, i.e. only a sequence comprising amino acid positions 2 to 201, 2 to 202, 1 to 201, 1 to 208 or 1 to 220 is repeated. In another preferred embodiment, the multimerization is heterogeneous, i.e. the multimer comprises a combination of at least two different sequences.

Any "variant" defined above is, preferably, a functional variant. A functional variant is a variant of the wild type HDAC4-NT as described above which retains its capability to repress myocyte enhancer factor 2 (MEF2). Preferably, the HDAC4-NT variant has at least 50% of the MEF2 repressing ability of HDAC4-NT comprising amino acid positions 1 to 220 of SEQ ID NO: 11 or 12. More preferably at least 60%, 70%, 80%, 90%, 95% or 100%.

An assay for testing whether a variant of HDAC4-NT is still functional disclosed by Backs et al., 2011 cited supra. Briefly, a reporter gene such as luciferase is coupled to a MEF2-regulated promoter. If this construct is expressed in a cell, the signal generated by the reporter gene is decreased in the presence of repressors of MEF2. Thus, variants of HDAC4-NT can be expressed in the cell and their ability to repress MEF2 can be determined by measuring the signal of the reporter gene relative to the signal in a control experiment with the presence of HDAC4-NT or a variant thereof.

It is to be understood that the most preferred variant of HDAC4 is not always the variant which has the highest activity as determined by the repression of MEF2 in the assay described above. As excessive repression of MEF2 may have deleterious effects, HDAC4 variants with decreased activity may be preferred as these have a wider therapeutic index, thus decreasing the risk of undesired side effects.

For this reason, HDAC4 2-201 and 2-202 are equally preferred. HDAC4 2-202 is especially preferred in those cases, where side effects have to be avoided, while HDAC4 2-201, Nucleic Acid In yet another aspect, the present invention relates to a nucleic acid encoding HDAC4-NT or a variant thereof for use as a medicament.

In yet another aspect, the present invention relates to a nucleic acid encoding HDAC4-NT or a variant thereof for use in the treatment or prevention of heart failure.

The term "nucleic acid" refers to a polymeric macromolecule made from nucleotide monomers. Nucleotide monomers are composed of a nucleobase, a five-carbon sugar (such as but not limited to ribose or 2'-deoxyribose), and one to three phosphate groups. Typically, a polynucleotide is formed through phosphodiester bonds between the individual nucleotide monomers. In the context of the present invention preferred nucleic acid molecules include but are not limited to ribonucleic acid (RNA) and deoxyribonucleic acid (DNA). Moreover, the term "polynucleotide" also includes artificial analogs of DNA or RNA, such as peptide nucleic acid (PNA).

The nucleic acid of the present invention encodes HDAC4-NT or a variant thereof. Since the genetic code is degenerated, i.e. each amino acid is encoded by more than one nucleic acid, each peptide or its variant may be encoded by a multiplicity of different nucleic acid sequences. Preferably, a nucleic acid encoding HDAC4-NT is defined by SEQ ID NO: 17.

Vector

For an effective treatment of heart failure, the increase of the amount of HDAC4-NT or a variant thereof is advantageous. The administration of HDAC4-NT as peptide may pose practical difficulties. Therefore, the use of expression systems which mediate expression of HDAC4-NT or a variant thereof by the cardiomyocytes of the patient are a solution for the problem underlying the present invention.

Thus, in yet another embodiment, the present invention relates to a vector comprising a nucleic acid encoding HDAC4-NT or a variant thereof.

In yet another embodiment, the present invention relates to a vector comprising a nucleic acid encoding HDAC4-NT or a variant thereof for use as a medicament.

In yet another embodiment, the present invention relates to a vector comprising a nucleic acid encoding HDAC4-NT or a variant thereof for use in the treatment or prevention of heart failure.

As used herein, the term "vector" refers to at least one nucleic acid or to a mixture of at least one nucleic acid and at least one protein which is capable of introducing the nucleic acid comprised therein into a cell. At least one nucleic acid comprised by the vector consists of or comprises at least one nucleic acid encoding HDAC4-NT or a variant thereof. In addition to the nucleic acid consisting of or comprising the nucleic acid encoding HDAC4-NT or the variant thereof, additional nucleic acids and/or polypeptides may be introduced into the cell. The addition of additional nucleic acids and/or polypeptides is especially preferred if said additional nucleic acids and/or polypeptides are required to introduce the nucleic acid encoding HDAC4-NT or the variant thereof into the cell.

In the context of the present invention it is preferred that HDAC4-NT or the variant thereof is expressed within the cell upon introduction of the vector or vectors. Examples of suitable vectors include but are not limited to plasmids, cosmids, phages, viruses or artificial chromosomes.

In preferred embodiments, the vector is selected from the group consisting of plasmids, cosmids, phages, viruses, and artificial chromosomes. More preferably, a vector suitable for practicing the present invention is a phage vector, preferably lambda phage and filamentous phage vectors, or a viral vector.

Preferred viral vectors are based on naturally occurring vectors, which are modified to be replication incompetent also referred to as non-replicating. Non-replicating viruses require the provision of proteins in trans for replication. Typically those proteins are stably or transiently expressed in a viral producer cell line, thereby allowing replication of the virus. The viral vectors are, thus, preferably infectious and non-replicating. The skilled person is aware of how to render various viruses replication incompetent.

In a preferred embodiment of the present invention the vector is selected from the group consisting of adenovirus vectors, adeno-associated virus (AAV) vectors (e.g., AAV type 1, type 2, type 5, type 6 and type 9), alphavirus vectors (e.g., Venezuelan equine encephalitis virus (VEE), sindbis virus (SIN), semliki forest virus (SFV), and VEE-SIN chimeras), herpes virus vectors (e.g. vectors derived from cytomegaloviruses, like rhesus cytomegalovirus (RhCMV) (14)), arena virus vectors (e.g. lymphocytic choriomeningitis virus (LCMV) vectors (15)), measles virus vectors, pox virus vectors (e.g., vaccinia virus, modified vaccinia virus Ankara (MVA), NYVAC (derived from the Copenhagen strain of vaccinia), and avipox vectors: canarypox (ALVAC) and fowlpox (FPV) vectors), vesicular stomatitis virus vectors, retrovirus, lentivirus, viral like particles, and bacterial spores.

An especially preferred vector with HDAC4-NT as insert is given in SEQ ID NO: 18. Also preferred is a vector as defined by SEQ ID NO: 19. Said sequence comprises luciferase instead of a peptide of the present invention. However, the exchange of the luciferase for HDAC4-NT is easily accomplished.

The most preferred vector is an adenovirus, more preferably adeno associated virus (AAV) type 1, type 6 or type 9. For use in humans, AAV types 1 or 6 are preferred, for use in mice AAV type 9.

To direct expression of HDAC4-NT or the variant thereof, the nucleic acid encoding it is operationally linked to an internal promoter and/or enhancer that is recognized by the transcriptional machinery of the cell. Suitable promoters may be derived from the genome of mammalian cells (e. g., MHCII promoter, EFlalpha promoter) or from mammalian viruses (e.g., the cytomegalovirus promoter, the spleen focus-forcing virus SFFV promoter). Especially preferred are promoters which enable the expression of the above-mentioned gene in cardiomyocytes.

One preferred promoter is defined by SEQ ID NO: 22. In an especially preferred embodiment, the promoter is a human troponin promoter as this promoter is especially well suited for cardiomyocyte-specific expression of transgenes. Preferably, the human troponin promoter has a nucleic acid sequence as defined by SEQ ID NO: 21.

In another preferred embodiment, the vector encodes a recognition site for micro-RNA 122 between the promoter and the terminator sequence so that said recognition site becomes part of the transcript produced from this vector. Since micro-RNA 122 is found in many types of cells but not in cardiomyocytes, said recognition site causes breakdown of the mRNA in those types of cells where micro-RNA 122 is present, thus preventing translation of the transcript. Preferably the recognition site for micro-RNA 122 has a nucleic acid sequence as defined by SEQ ID NO: 20.

In a particularly preferred embodiment of the present invention, the vector comprises a human troponin T promoter as defined above and a nucleic acid sequence encoding a recognition site for micro-RNA 122 as defined above.

As used herein, "operatively linked" means incorporated into a genetic construct so that expression control sequences effectively control expression of a coding sequence of interest.

Specific initiation signals may also be required for efficient translation of coding sequences. These signals include the ATG initiation codon and adjacent sequences. Exogenous translational control signals, including the ATG initiation codon, may additionally need to be provided. One of ordinary skill in the art would readily be capable of determining this and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic.

Pharmaceutical Compositions

In a preferred embodiment of the present invention, the peptides, nucleic acids or vectors of the present invention are part of a pharmaceutical composition. These embodiments relate to all parts of the invention, i.e. to ABHD5 and the variants thereof as well as HDAC4-NT and the variants thereof.

The term "composition" refers to the combination of a vector, nucleic acid or peptide of the present invention and at least one further compound selected from the group consisting of pharmaceutically acceptable carriers and pharmaceutical excipients.

"Pharmaceutically acceptable" means approved by a regulatory agency of the Federal or a state government or listed in the U.S. Pharmacopeia or other generally recognized pharmacopeia for use in animals, and more particularly in humans.

The term "carrier", as used herein, refers to a pharmacologically inactive substance such as but not limited to a diluent, excipient, or vehicle with which the therapeutically active ingredient is administered. Such pharmaceutical carriers can be liquid or solid. Liquid carrier include but are not limited to sterile liquids, such as saline solutions in water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. A saline solution is a preferred carrier when the pharmaceutical composition is administered intravenously or intranasally by a nebulizer.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Examples of suitable pharmaceutical carriers are described in "Remington's Pharmaceutical Sciences" by E. W. Martin.

Test System

In yet another embodiment, the present invention relates to a method for identifying a compound which modulates the activity and/or localization of ABHD5 or a variant thereof comprising the steps of
- a) contacting a test system comprising ABHD5 or a variant thereof with a candidate compound;
- b) determining whether the candidate compound modulates the activity and/or localization of ABHD5 or the variant thereof;
- c) identifying the compound as a compound which modulating the activity of ABHD5 or the variant thereof based on the comparison of the activity and/or localization of ABHD5 or the variant thereof in the test system comprising the candidate compound and the activity of ABHD5 or the variant thereof determined in a control in step b).

It is preferred to use the variant of ABHD5 whose activity is to be determined in the test system. However, if it is expected that two variants of ABHD5 will show the same response to the candidate compound, it is also possible to use only one of these variants and to extrapolate to the effect of said compound on the other candidate compound. Similarly, if wild-type ABHD5 and a variant thereof can be expected to show the same response, it may be possible—and thus also preferred—to use a test system comprising wild type ABHD5 to test the modulation of the variant and vice versa.

A test system is a composition of reagents comprising ABHD5 or a variant thereof, wherein said ABHD5 generates a signal which allows the differentiation between a test compound which modulates the activity of ABHD5 and a test compound which does not.

If localization of ABHD5 is used as an indicator of its activity, the test system is, preferably, a cell expressing ABHD5 or a variant thereof, more preferably a cardiomyocyte.

If the enzymatic activity of ABHD5 is to be analyzed, the test system is, preferably, a cell as described above. However, due to their simplicity, cell free systems are more preferred.

Preferably, the modulation of the activity of ABHD5 is determined by comparing a test system to which the test compound is added and an otherwise identical test system without the test compound.

Preferably, the activity determined with the test system is the ability of ABHD5 to mediate cleavage of HDAC4 or a variant of HDAC4 which does not bind to MEF2 into a fragment which binds to MEF2. Preferably, said fragment is HDAC4-NT as described further above in the present application.

Preferably, the modulation of the activity of ABHD5 is an increase of its activity. Said increase may be caused by increased affinity of ABHD5 for HDAC4 or by an increased turnover number. The cleavage of HDAC4 may be determined as explained in the examples section.

Moreover, the activity of ABHD5 or a variant thereof may be influenced by its binding affinity to lipid droplets as set forth above. Thus, the localization of ABHD5 may be used as an indicator of its activity. The less ABHD is bound to lipid droplets, the higher its activity.

We further claim potential tests were the link to HDAC4 or the proteolytic activity of abhd5 are directly or indirectly tested. This could be achieved by the subcellular localization (bound to LD, vs homogenous expression in the cytosol/nucleus) of ABHD4 may be analyzed by expressing GFP- or RFP or other fluophor-tagged ABHD5 in cell-based assays (high-content screening).

Protein-protein interaction assays (e.g. alpha screen, FRET assays, mammalian two hybrid screen) to test the binding between ABHD5 and perilipin or between ABHD5 and HDAC4.

The test compound may be any peptide or small molecule. A peptide as referred to in this embodiment comprises at least 2, more preferably at least 3 even more preferably at least 4 and most preferably at least 5 amino acids linked by peptide bonds. Preferably, said amino acids are amino acids found in nature, more preferably proteinogenic amino acids. However, it is also preferred to use peptides comprising at least one amino acid having a residue not found in nature.

A small molecule is, preferably, an organic molecule having a molecular weight of not more than 2000 Da, more preferably not more than 1600 Da, even more preferably not more than 1200 Da and, most preferably, not more than 800 Da.

Since the proteolytic cleavage of HDAC4 mediated by ABHD5 generates an N-terminal fragment (HDAC4-NT) which is useful for the treatment or prevention of heart failure, the identification of modulators which increase the activity of ABHD5, preferably in cell based systems and more preferably in vivo, is of great clinical importance. Hence, the test system of the invention is a valuable tool for the discovery of novel pharmaceutical compounds useful for the treatment or prevention of heart failure.

In yet another embodiment, the present invention relates to the use of ABHD5 for identifying a compound which suppresses myocardial remodeling.

TABLE 1

Overview over the sequences disclosed by the present application

| SEQ ID NO. | Sequence |
|---|---|
| 1 | Human ABHD5 polypeptide |
| 2 | Orangutan ABHD 5 polypeptide |
| 3 | Mouse ABHD5 polypeptide |
| 4 | Rat ABHD5 polypeptide |
| 5 | Pig ABHD 5 polypeptide |
| 6 | Human ABHD5 nucleic acid |
| 7 | Orangutan ABHD 5 nucleic acid |
| 8 | Mouse ABHD5 nucleic acid |
| 9 | Rat ABHD5 nucleic acid |
| 10 | Pig ABHD 5 nucleic acid |
| 11 | Human HDAC4 polypeptide |
| 12 | Mouse HDAC4 polypeptide |
| 13 | Human HDAC4-NT polypeptide |
| 14 | Mouse HDAC4-NT polypeptide |
| 15 | Human HDAC4 nucleic acid |
| 16 | Mouse HDAC4 nucleic acid |
| 17 | Human HDAC4-NT nucleic acid |
| 18 | Expression vector encoding human HDAC4-NT |
| 19 | Expression vector for cardiomyocyte-specific expression of transgenes, encodes luciferase as transgen |
| 20 | Recognition site of micro-RNA 122 |
| 21 | Human troponin T promoter sequence |
| 22 | CMVMLC260-Promoter sequence |

The following examples are merely intended to illustrate the invention. They shall not limit the scope of the claims in any way.

EXAMPLES

Materials and Methods

Transthoracic echocardiography. Echocardiography was performed using a Sonos 5500 with a S12 transducer (12 MHz). The echocardiographer was blinded with respect to the treatment group. Mice were shaved and left ventricular parasternal short-axis views were obtained in M-mode imaging at the papillary muscle level. Three consecutive beats were used for measurements of left ventricular end-diastolic internal diameter (LVEDD) and left ventricular end-systolic internal diameter (LVESD). Fractional shortening (FS) was calculated as FS %=[(LVEDD−LVESD)/LVEDD]×100%.

Generation of an Adeno Associated Virus (HDAC4-AAV).

HDAC4 aa2-201 was cloned into a double-stranded AAV-vector downstream of a CMV-enhanced short (260 bp) myosin light chain promoter (CMVenh/MLC260). AAV9 vectors were produced with the three plasmid transfection method.

RNA Analysis.

Total RNA was isolated from ventricular tissue using TRIzol (Invitrogen, Germany). Total RNA was digested with DNase, and cDNA synthesis from 500 ng of RNA was carried out using a SuperScript first-strand synthesis system for RT-PCR (Invitrogen). Quantitative real-time PCR (qPCR) was performed with Universal ProbeLibrary (Roche) by using TaqMan Universal PCR Mastermix (Applied Biosystems) and detection on a 7500 Fast Cycler (Applied Biosystems) as described previously [1].

Transverse Aortic Constriction.

TAC to a 27 gauge stenosis was performed in 9-10 week-old male black six mice (charles river), mice as described previously [2]. AAV vectors were intravenously injected into the tail vein of male adult mice as 150-200 μL bolus using a sterile syringe and 29-gauge needle. Animals were euthanized by cervical dislocation. Organs were dissected and rapidly frozen in liquid nitrogen.

Western Blotting.

Proteins from heart tissue and cultured cardiomyocytes were isolated, and Western blot analysis was performed according to protocols described previously [1]. Primary antibodies used were anti-flag (santa cruz), anit-myc (santa cruz), anti-gfp (abcam). Primary antibody incubation was followed by corresponding horseradish peroxidase (HRP)-conjugated secondary anti-mouse and anti-rabbit antibodies and ECL detection. Relative protein levels were detected by densitometry using the Image J program.

Histology.

Hematoxylin and eosin (H&E) and Masson's trichrome stainings were performed as previously described [3]. Cardiomyocyte size was assessed on H&E-stained sections by using Image J software (http://rsb.info.nih.gov/ij/). More than 200 randomly chosen cardiomyocytes from each group were analyzed to measure cross-sectional cardiomyocyte area. To quantify cardiac fibrosis, 20 trichrome-stained sections (magnification 20×) from the left ventricle were randomly selected, and morphometric analysis by using Image J was performed. Photographs were acquired with an Olympus SZH zoom stereo dissection scope with an Optronics DEI-750 CCD digital camera. All data were analyzed by a single observer blinded to the mouse genotypes.

Results

Overexpression of N-Terminal HDAC4 Via an Adeno Associated Virus (AAV) in Mice is Cardioprotective.

Figure 2A:
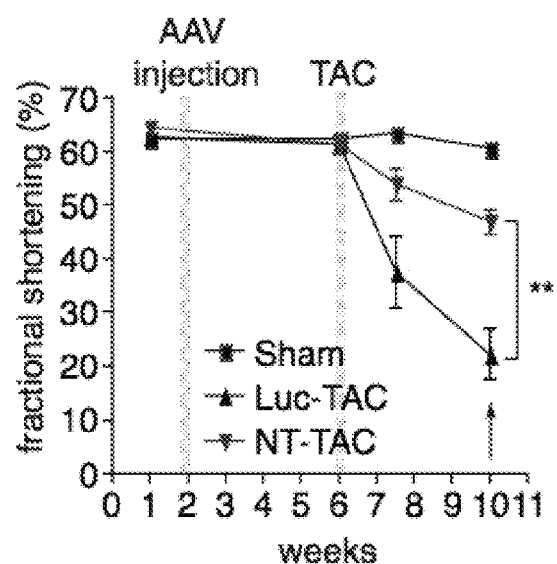
FIG. 2: HDAC4 aa 2-201 were cloned into an AAV-9 virus (NT). NT was applied to animals 6 weeks before TAC surgery (indicated as a lines in the timecourse of echos, A). Controls received Luciferase cloned into AAV-9 (LUC). In consecutive echos, fs decreased after TAC surgery whereas NT treated animals were protected from reduced function, n=5, p<0.01. Arrow indicates timepoint of echo in figure (B). Heartweight/Bodyweight ratio was normalized (n=5; p<0.01) (C)
Figure 2B:
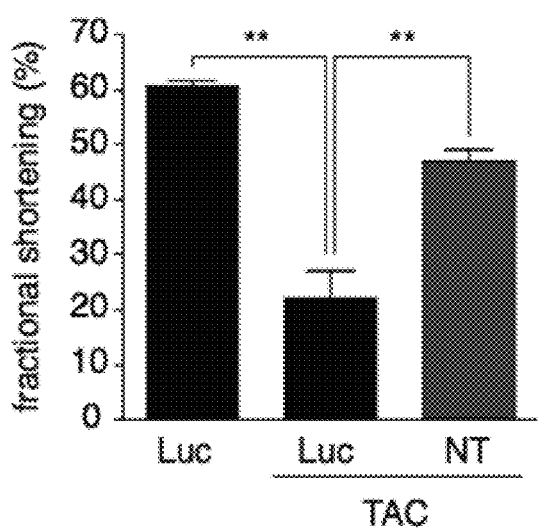
Figure 2C:
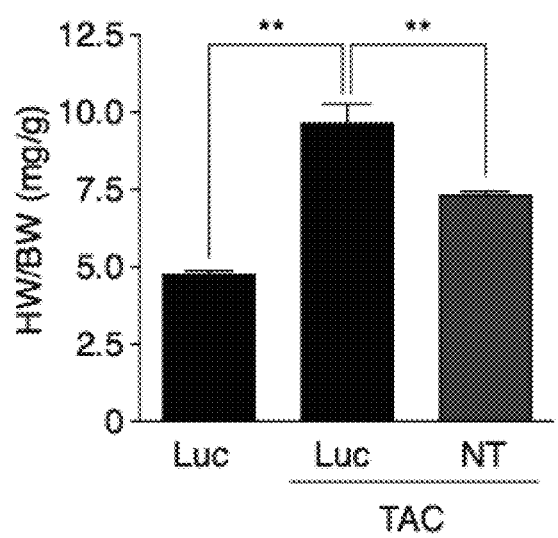
Figure 3A:
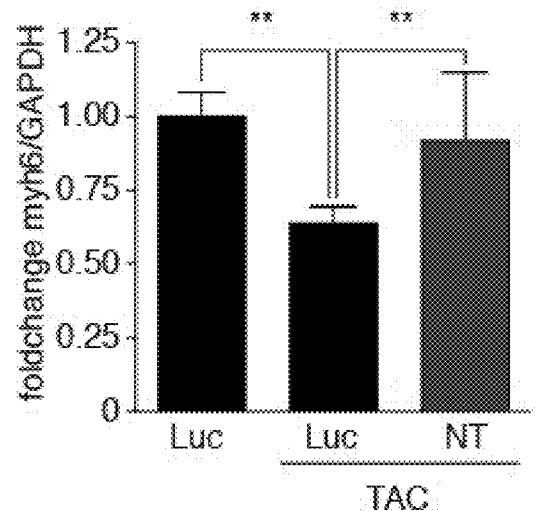
FIG. 3: In part, dyregulated genes were normalized, such as myh6 (A) and nppb (D). Myh7 (B) and nppa (C) were not normalized by NT-treatment (n=5). Values indicate relative expression level normalized to WT sham group; ±SEM *p<0.05.
Figure 3B:
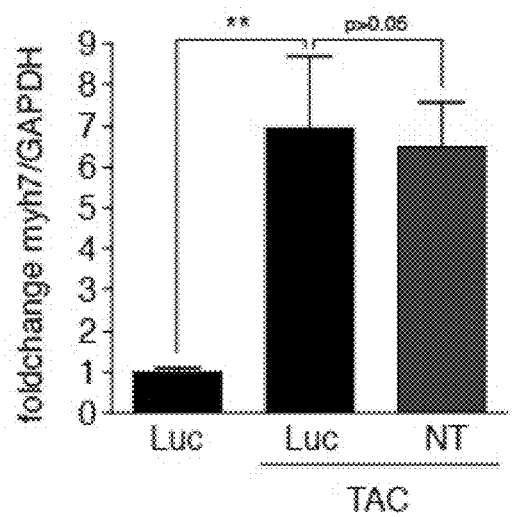
Figure 3C:
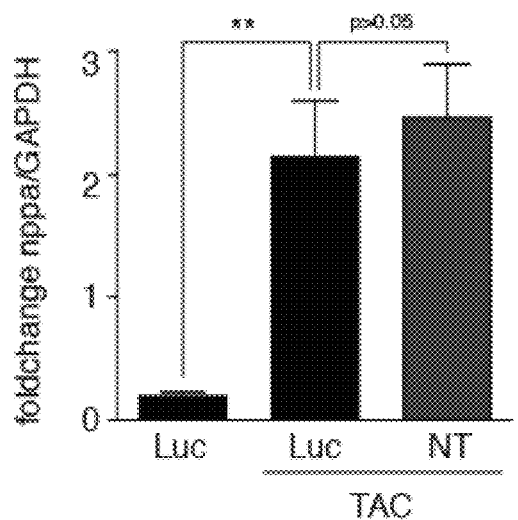
Figure 3D:
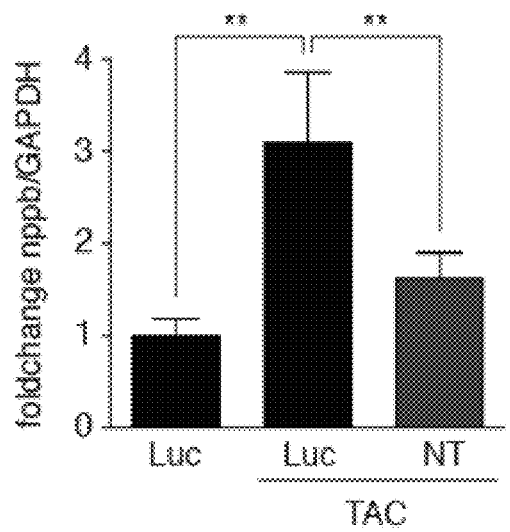

HDAC4-NT is able to inhibit the transcription factor myocyte enhancer factor 2 (MEF2). [4] MEF2 is thought to be involved in pathological cardiac remodeling. [5] We therefore hypothesized that HDAC4-NT could have beneficial and cardioprotective effects in vivo. By cloning HDAC4-NT into a cardiotrophic AAV substrain (AAV9) under the control of a cardiomyocyte specific promoter (CMVenh-MLC260), we were able to transduce cardiomyocytes in vivo via a single tail vein injection. Mice were injected 4 weeks before they were exposed to transthoracic aortic constriction (TAC)-surgery as a model for cardiac stress and the development of heart failure. By doing so, animals that were treated with AAV-HDAC4-NT showed reduced cardiac hypertrophy, improved cardiac function and normalized gene regulation from genes that are known to play an important role in pathological cardiac remodeling (FIG. 2). Cardiac fibrosis that was developed by control-mice was diminished when animals were treated with HDAC4-NT.

We further aimed to investigate the endogenous role of HDAC4-NT. In wildtype animals, HDAC4-NT production is increased after physiological exercise. We generated conditional HDAC4-knockout animals, lacking HDAC4 in cardiomyocytes only and exposed these animals to running exercise. HDAC4-KO animals showed a reduced exercise tolerance with a reduced left ventricular function after running exercise. Reduced exercise performance was rescued when HDAC4-KO were treated with AAV-HDAC4-NT, indicating that HDAC4-NT is crucial for sustained cardiac function after cardiac stress (FIG. 15). By further carefully characterization of the animals we did not found any harmful effects or any side effects that were linked to AAV-HDAC4-NT treatment.

Abhd5 is a Critical HDAC4 Protease.

Figure 4:
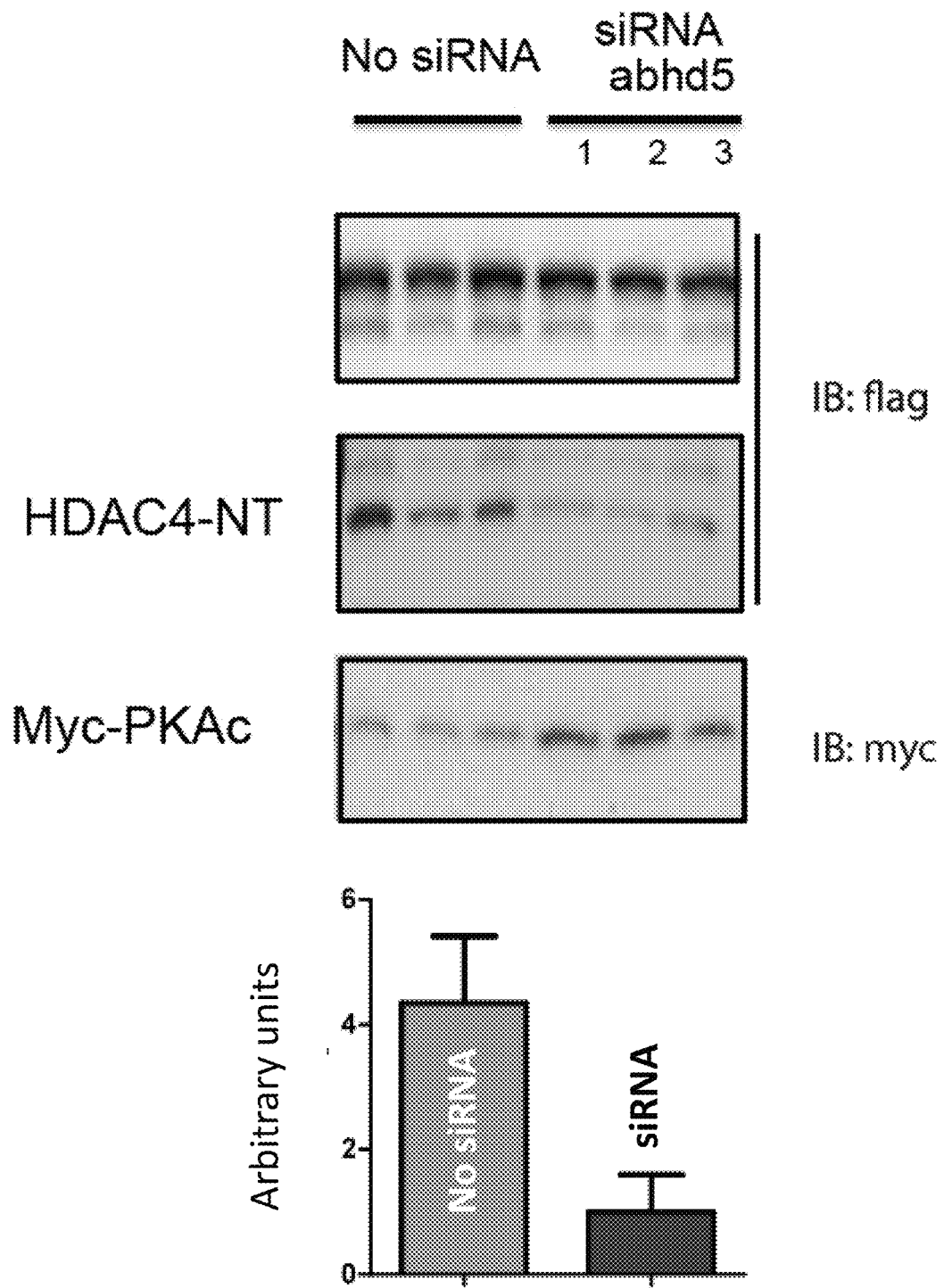
FIG. 4: Validation experiment of the siRNA-screen confirmed results from the siRNA screen. Co-expression of flag tagged HDAC4 with myc tagged PKA leads to a cleavage of HDAC4 (first three lanes). The cleavage is not longer present when abhd5 is knocked down by using different siRNA in the last three lanes (siRNAs labeled with 1-3). Quantification of the western blots confirmed the results (p<0.05).
Figure 5:
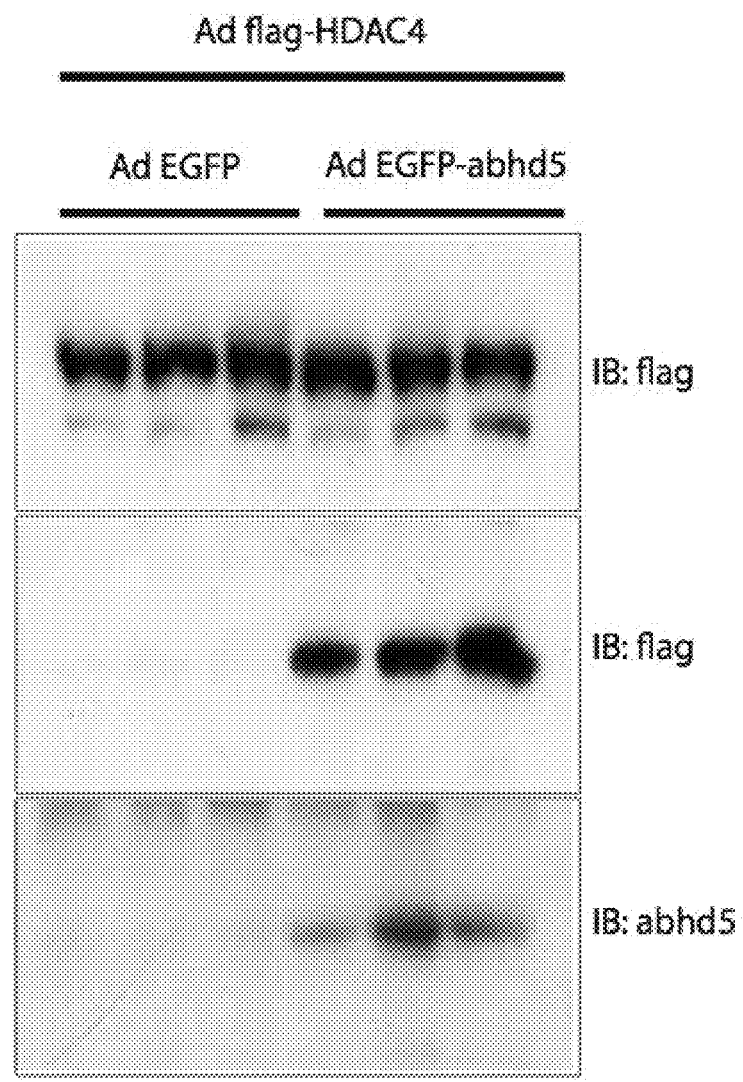
FIG. 5: To proof the results from our loss of function approach, we overexpressed abhd5 in cardiomyocytes (last three lanes). Overexpressed flag tagged HDAC4 was cleaved whenever gfp tagged abhd5 was coexpressed. IB: immunoblot; Ad: adenovirus construct.

To get insides about the upstream regulation of HDAC4 cleavage, we performed a siRNA-screen with a set of potential serine-proteases. By doing so, we identified a protein called 1-acylglycerol-3-phosphate O-acyltransferase (abhd5) playing a crucial role in PKA induced HDAC4 cleavage. HDAC4 cleavage was not longer present when abhd5 was knocked down by different siRNAs even when PKA was co-expressed with HDAC4 (FIG. 4). Abhd5 is characterized by typical structural features that can be found predominantly in serine proteases. However, it was not shown before, that abhd5 can indeed act as a protease. By adenoviral overexpression in neonatal rat ventricular myocytes (NRVMs) of abhd5 we were able to achieve HDAC4 cleavage without additional PKA activation or expression (FIG. 5).

Abhd5 Overexpression Leads to MEF2 Inhibition and is Cleavage Dependent.

Figure 6:
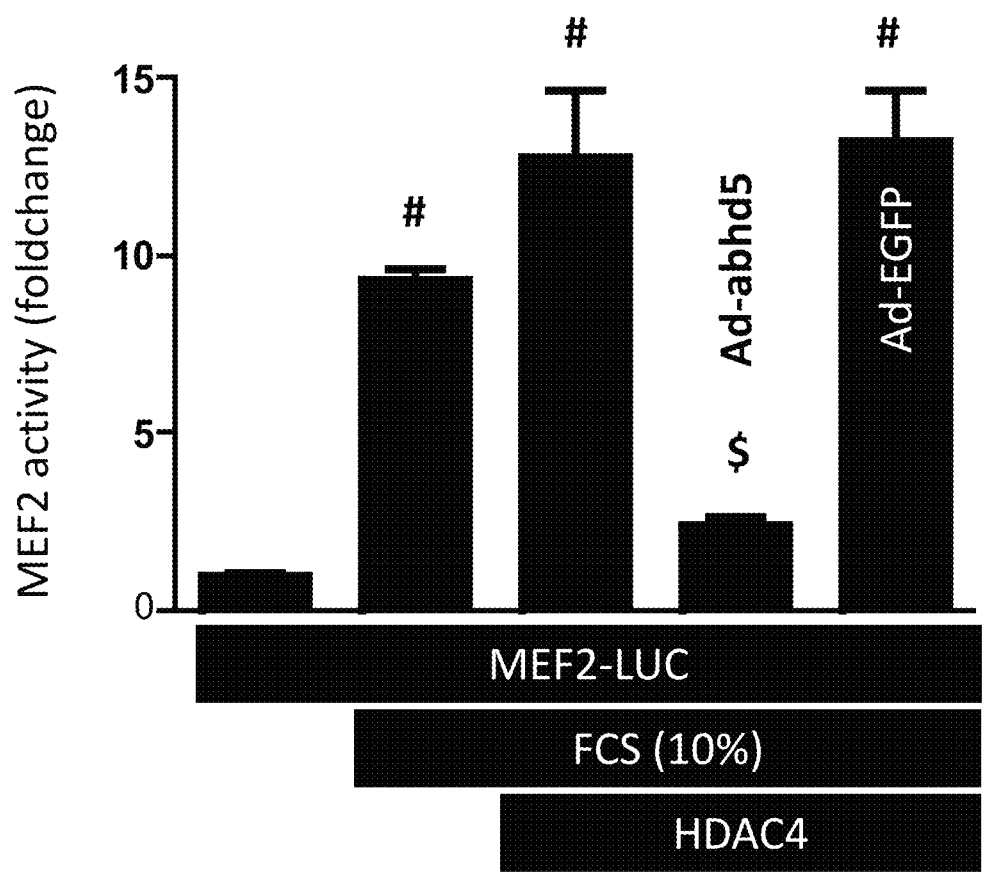
FIG. 6: Overexpression of abhd5 rescues FCS induced MEF2 luciferase activity. Neonatal rat ventricular cardiomyocytes were treated with 10% FCS for 24 h. HDAC4 alone was not able to inhibit this activation, whereas coexpression of abhd5 was able to blunt the MEF2 activation back on a basic value. This effect was not seen when cells were treated with a EGFP tagged control virus. MEF2-Luc: myosin enhancer factor 2 luciferase construct; FCS: fetal bovine serum; Ad: Adenovirus; #p<0.05 treatment vs. no treatment; $p<0.05 Ad-abhd5 treated vs. cells treated with FCS 10%.

By using a MEF2-luciferase assay, we found that abhd5 is able to completely normalize MEF2 activity induced by fetal calf serum (FCS), which is commonly used to induce cardiomyocyte hypertrophy. EGFP control virus did not show any beneficial effects in this system (FIG. 6)

Abhd5 Inhibits Cardiomyocyte Hypertrophy In Vitro.

Figure 7:
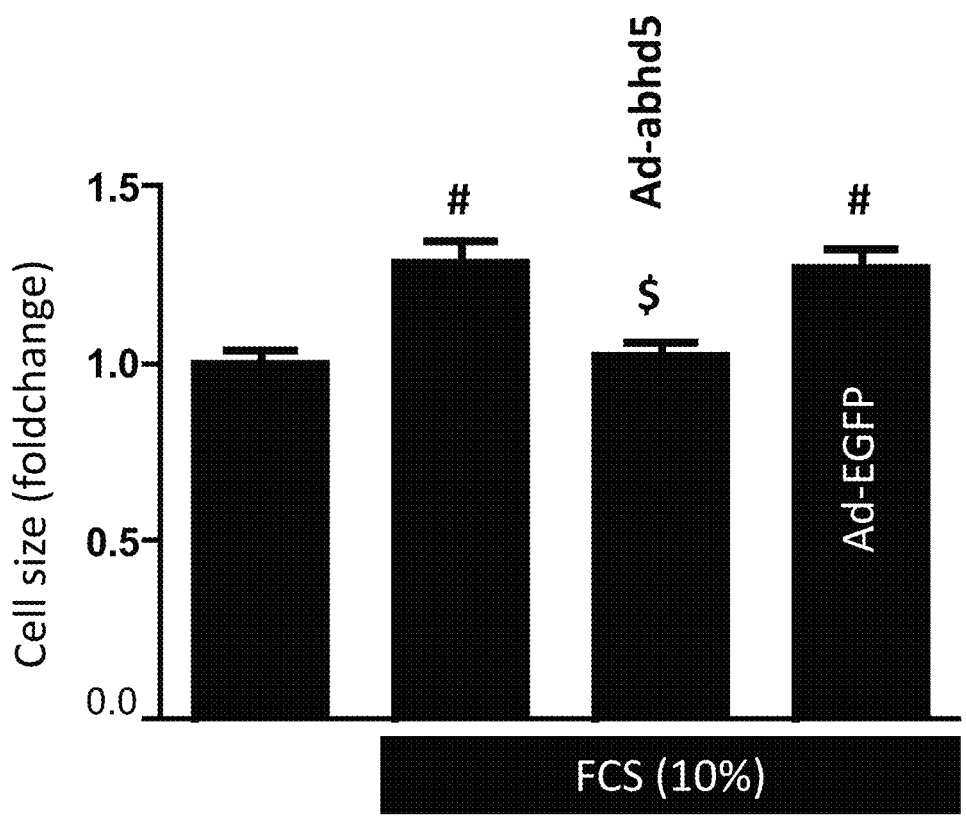
FIG. 7: Cardiomyocyte hypertrophy was significant reduced when abhd5 was expressed. A FCS induced hypertrophy did not show any beneficial effects on cardiomyocytes. NRVM: neonatal rat ventricular myocytes; FCS: felta bovine serum; #p<0.05 cell size of groups as indicated compared to control group without FCS; $p<0.05 cell size of abhd5 treated group compared to FCS treated group.
Figure 9A:
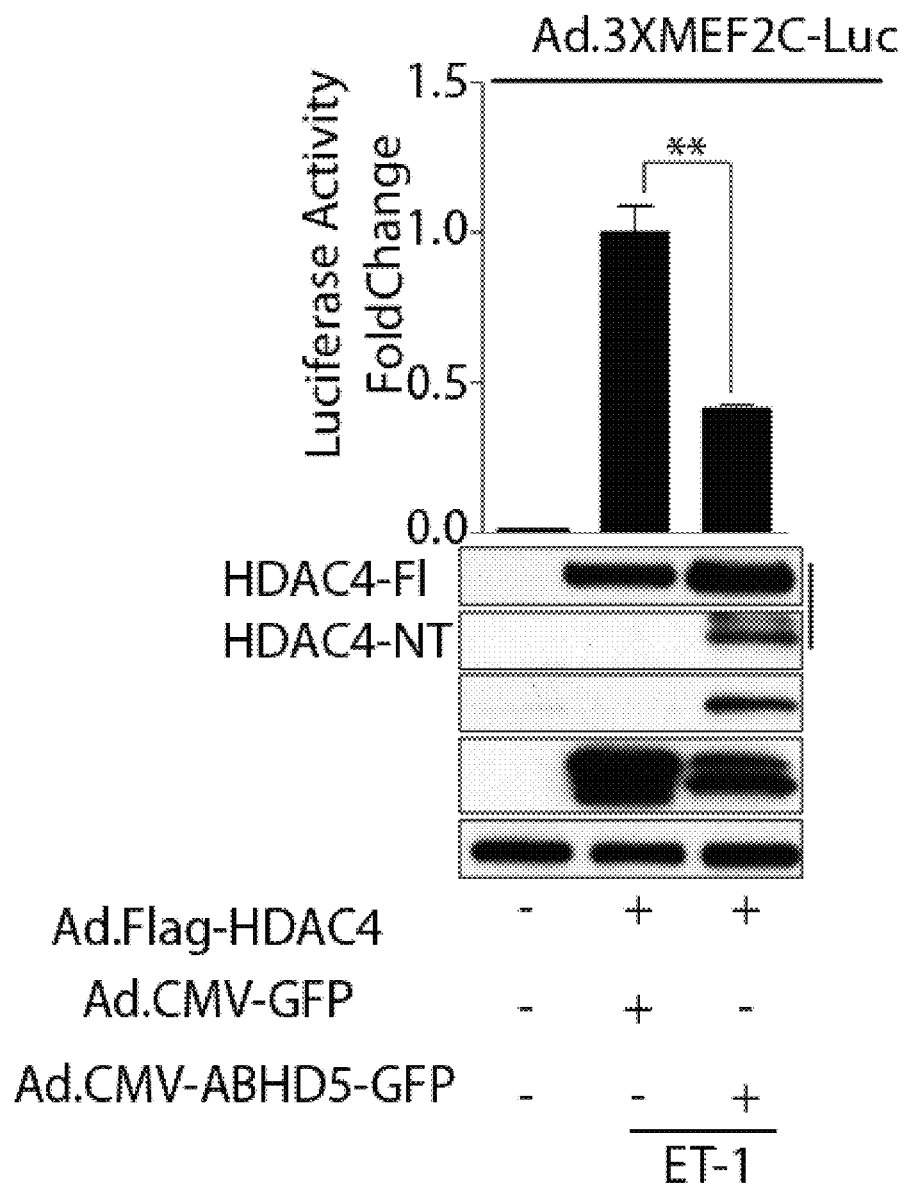
FIG. 9: (A) The transcription factor myocyte enhancer factor 2 (MEF2) is sufficiently repressed by overexpression of ABHD5. MEF2-luciferase reporter was overexpressed in neonatal rat cardiomyocytes and stimulated with either endothelin-1 (ET-1) or (B) fetal calf serum (FCS) for 24 h. Co-expression of HDAC4 and ABHD5 leads to a cleavage of HDAC4 and consequently to a repression of MEF2 luciferase activity. Equally expression of HDAC4, ABHD5 and equally protein loading was confirmed by westernblot analysis as indicated. Values are shown as mean±SEM; n>3/group; **p<0.05.
Figure 9B:
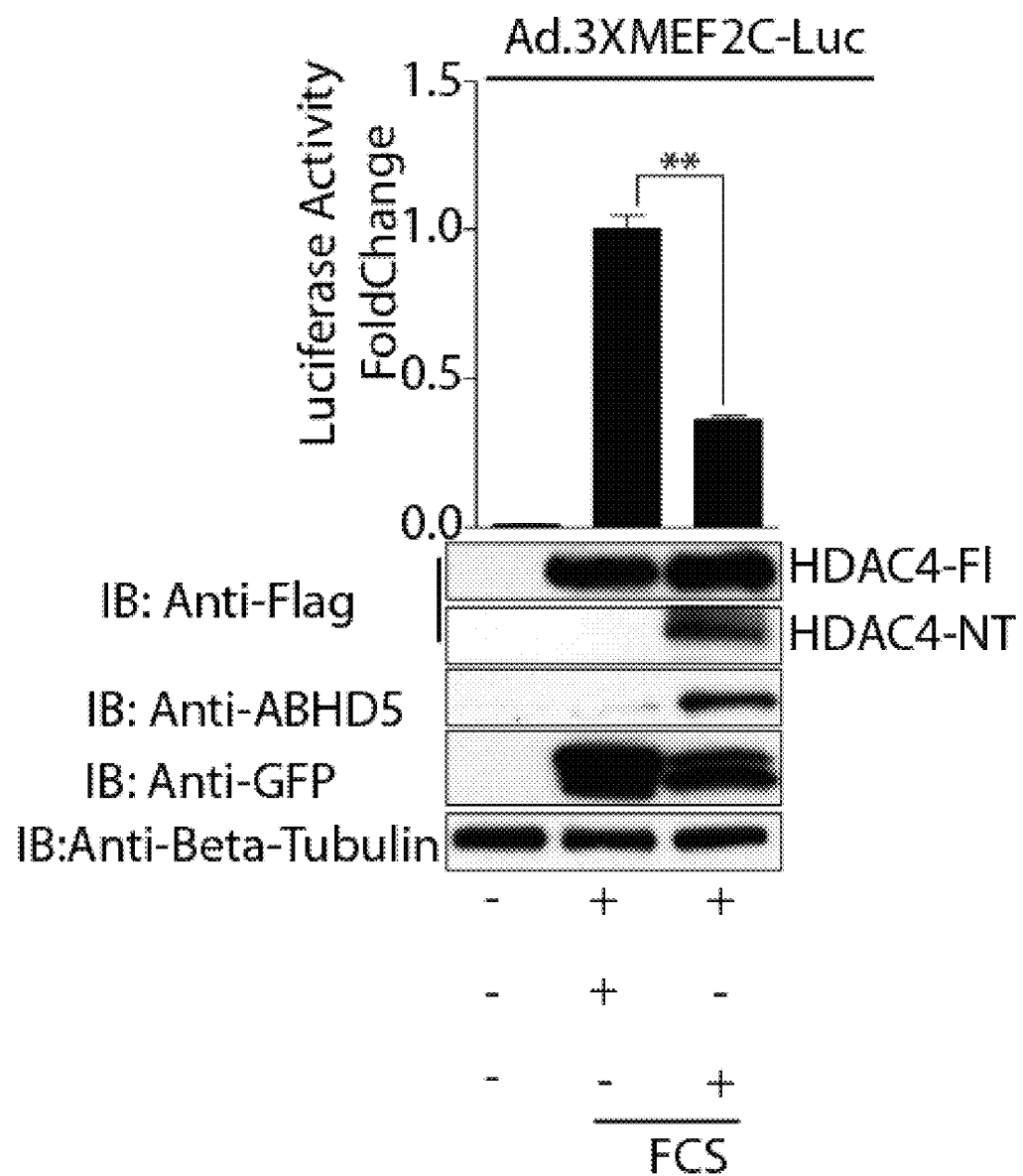
Figure 10:
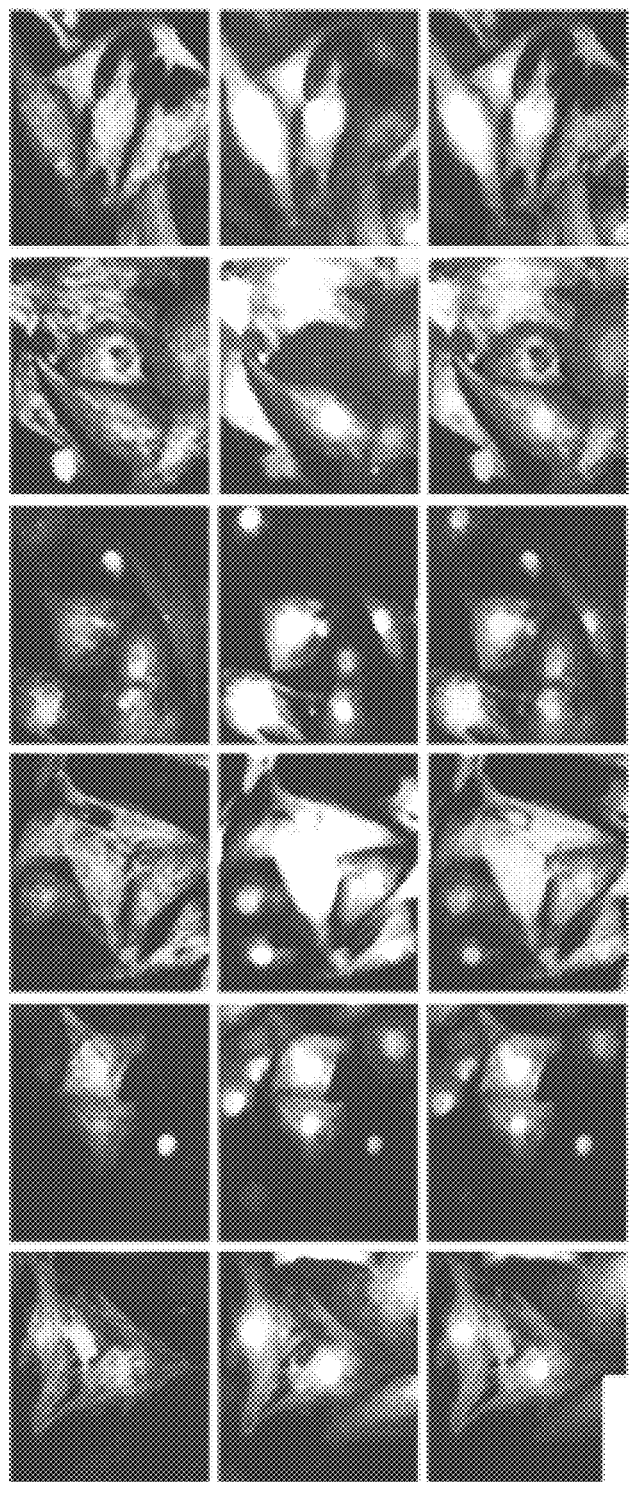
FIG. 10: ABHD5 counteracts cardiomyocyte hypertrophy in vitro. We stimulated neonatal rat cardiomyocyte with the prohypertorphic agents endothelin-1 (ET-1) and fetal calf serum (FCS) for 24 h as indicated. By adenoviral overexpression of ABHD5, hypertrophic response was blunted. (B) Cardiomyocyte size was quantified by counting 3 fields of view (>100 cardiomyocytes per field). Values are sown as mean±SEM; **p<0.05.
Figure 11:
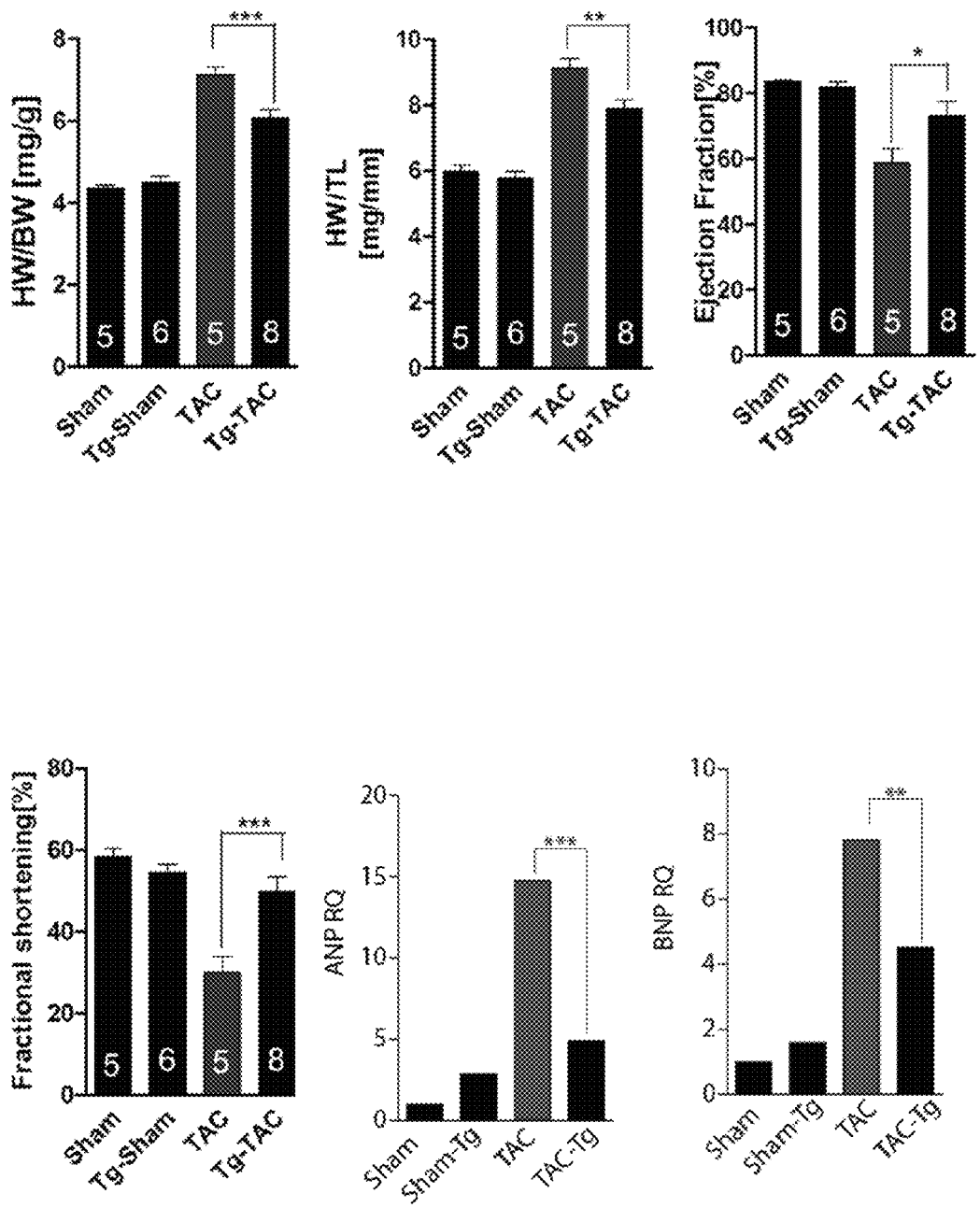
FIG. 11: Transgenic overexpression of ABHD5 in vivo protects from cardiac hypertrophy and heart failure. We generated transgenic animals, overexpressing ABHD5 under the control of the αMHC promoter. 3 weeks after induction of pathological cardiac remodeling by transaortic constriction (TAC), we found less hypertrophy indicated by a reduction of heartweight/bodyweight ratio (HW/BW) and heartweight/tibia length ratio (HW/TL). Left ventricular function was improved in transgenic animals, shown as ejection fraction and fractional shortening. Classical pathological genes, such as atrial natriuretic peptide (ANP) and brain natriuretic peptide (BNP) were less induced in ABHD5 transgenic animals. Values are shown as mean±SEM; *p<0.05; p<0.01; *p<0.001.
Figure 12:
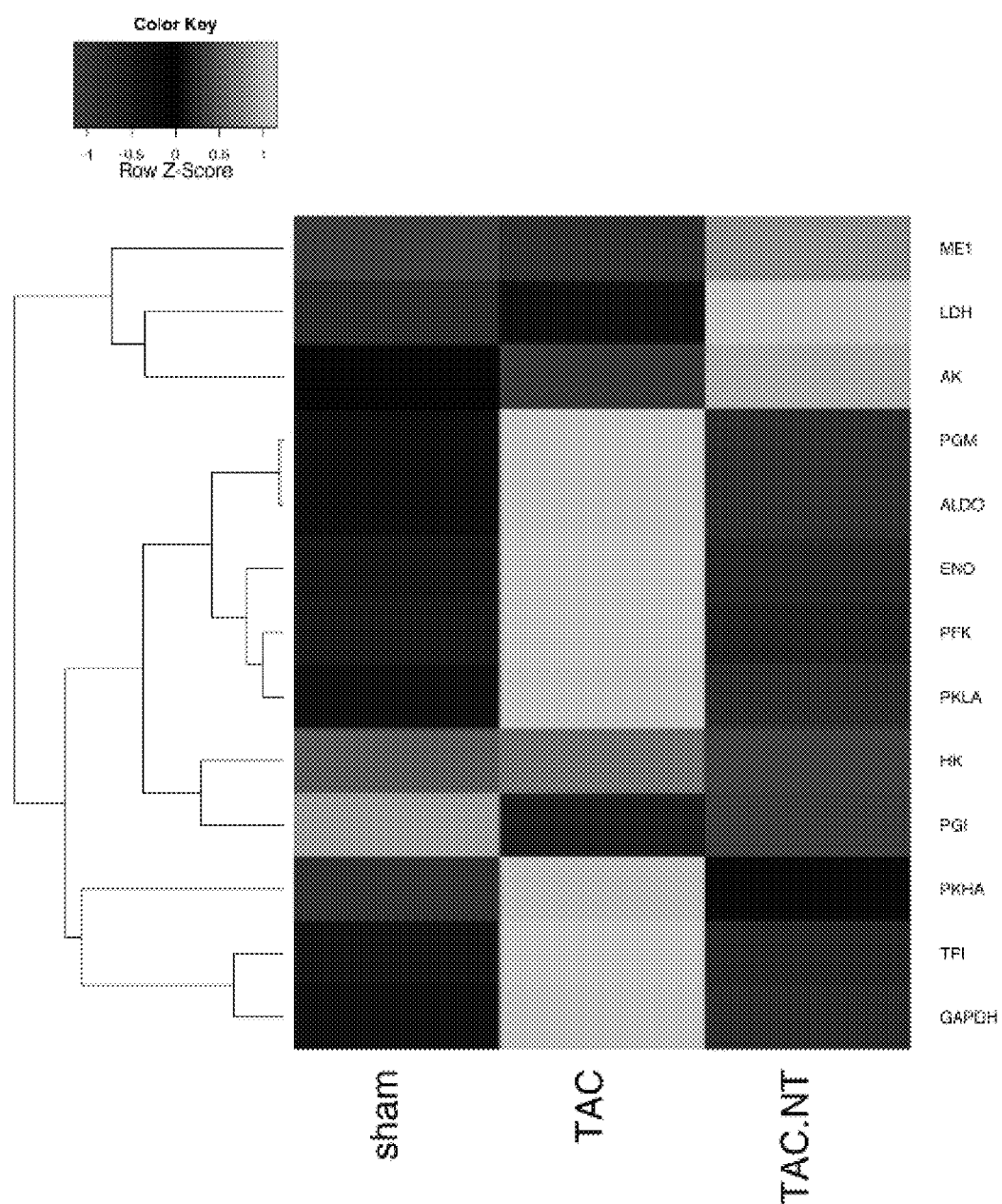
FIG. 12: HDAC4-NT reverses pathological induction of metabolic genes. We measured 4 weeks after induction of pathological cardiac remodeling by transaortic constriction (TAC) the enzymatic activity of key enzymes of the glycolysis. Pathological induction of glycolytic enzymes was reversed when HDAC4 was overexpressed by using the previous described novel AAV-construct. We show here a hierarchical clustering of enzymatic activity of key enzymes as indicated. Color key shows difference from the mean.
Figure 13:
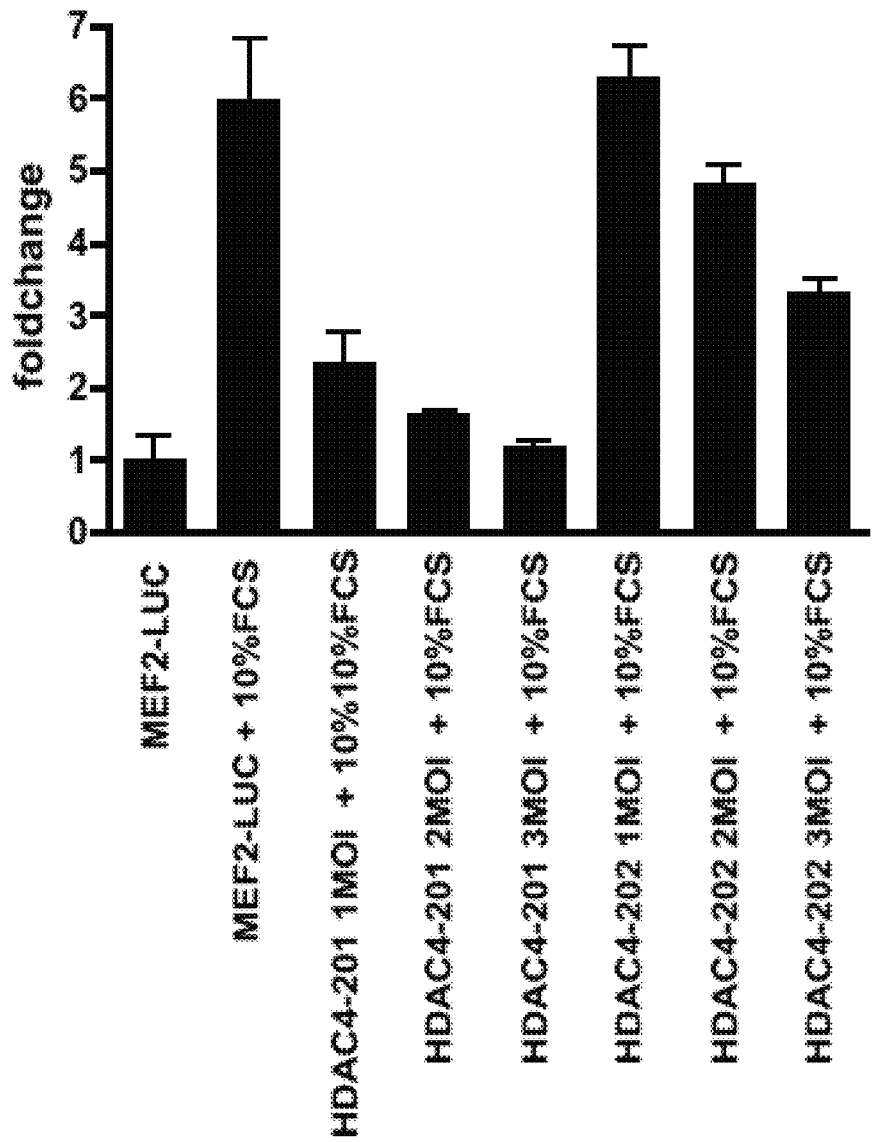
FIG. 13: HDAC4 2-202 inhibits MEF2 luciferase activity as well. To test whether different mutations of HDAC4 lead to inhibition of MEF2, we overexpressed HDAC4 2-202 by using an adenovirus system in neonatal rat cardiomyocytes and treated them with the prohypertrophic agent fetal calf serum (FCS). By overexpression of either HDAC4 2-201 or 2-202 endogenous MEF2 activity was sufficient inhibited. We found HDAC4 2-202 was less efficient compared to HDAC4 2-201 in inhibiting MEF2 luciferase activity. In case of pharmacological interventions, this could be an eligible aim since transient or moderate inhibition of MEF2 might be more useful in the clinical setting. Therefore, we claim HDAC4 and HDAC4 mutants as potential therapeutic tools for inhibition of MEF2 and consecutive pathological hypertrophy or pathological cardiac remodeling.
Figure 14:
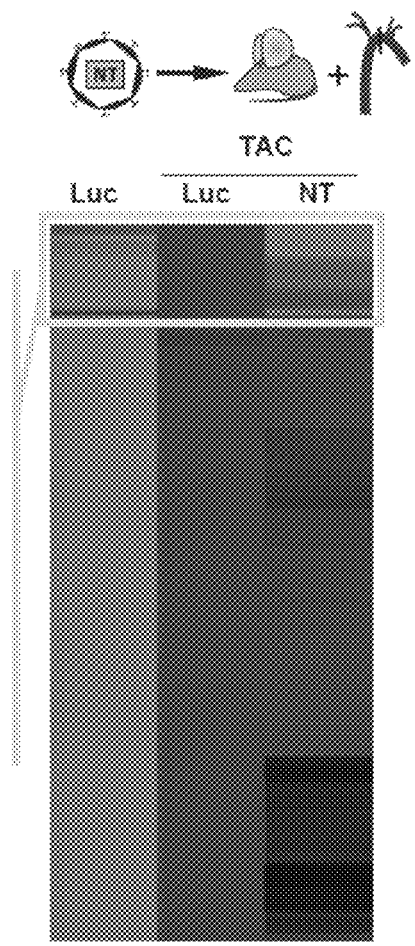
FIG. 14: HDAC4 aa 2-201 were cloned into an AAV-9 virus (NT). NT was applied to animals 6 weeks before TAC surgery. Controls received Luciferase cloned into AAV-9 (LUC). Expression analysis of hearts revealed a specific pattern of genes that was completely normalized in animals that received AAV-NT. These genes are listed beside the heatmap. All of these genes were upregulated in TAC (p<0.0001) and normalized as compared to the AAV-LUC treated sham group (±20%).
Figure 15A:
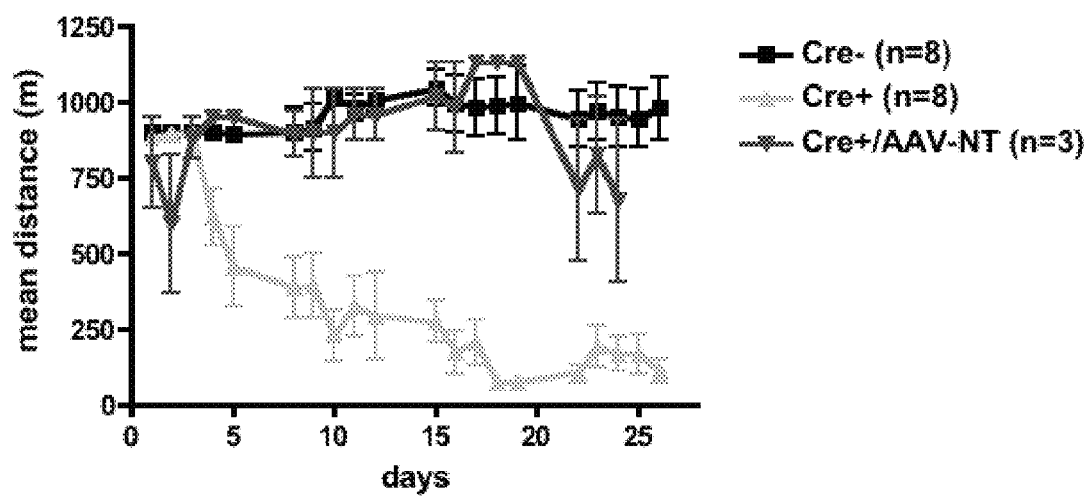
FIG. 15: Forced treadmill running was performed twice a day during a 4 week running training program. Shown is the total distance that WT and HDAC4-KO mice run during the entire training program within 4 weeks (A) and the daily distance until exhaustion (B). AAV-NT expression in HDAC4 KO animals was able to rescue the phenotype of reduced exercise performance. Values are shown as mean+SEM (HDAC4-KO and WT n=8; AAV-NT n=3). Echocardiography was performed directly after exercise and revealed a reduced fractional shortening in HDAC4-KO animals, values are shown as mean+SEM (n=8/group; *p<0.05). Westernblot against N-terminal HDAC4 shows and increased HDAC4-NT production after 2 weeks of exercise (D). GAPDH is shown as a loading control.
Figure 15B:
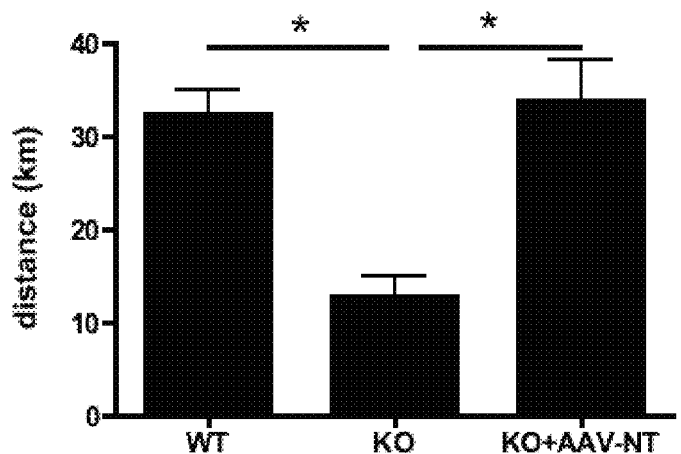
Figure 15C:
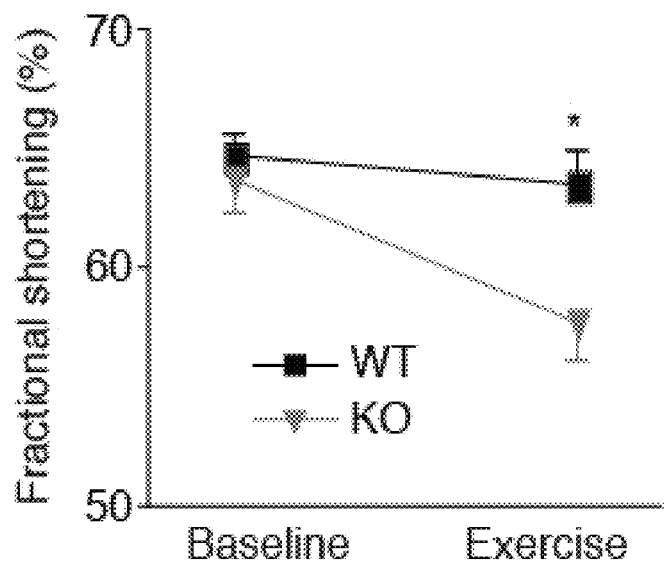
Figure 15D:
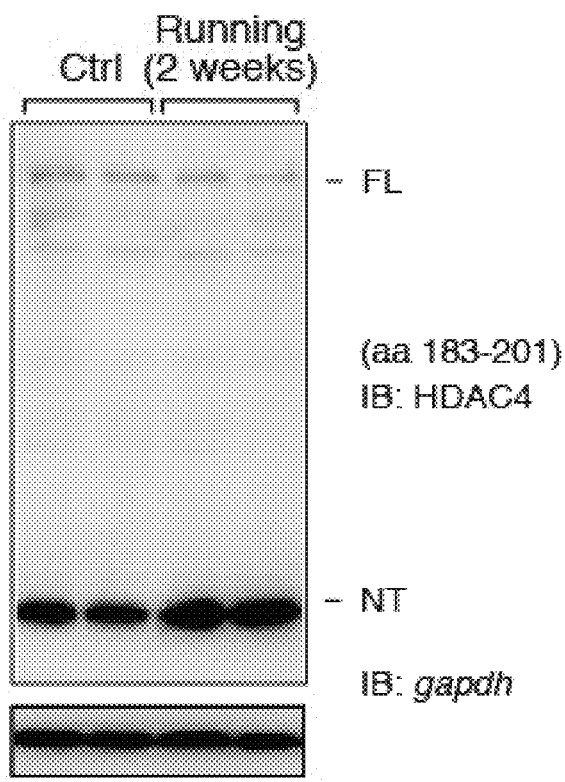

We next hypothesized, that abhd5 induced HDAC4-NT is able to inhibit cardiomyocyte hypertrophy in vitro. Indeed, abhd5 was able to inhibit FCS induced cardiomyocyte hypertrophy. This effect was independent from a control virus with EGFP. (FIG. 7)

Discussion

We found that HDAC4-NT is cardioprotective in mice and thus could serve as a potential pharmacological tool for the treatment of heart failure in human. This was surprising because earlier approaches to protect the heart by overexpression of a class II HDAC failed [6]. These earlier approaches used transgenic expression of full length HDACs and specific mutations of phosphosites to render HDACs signal-resistant and to force them to localize to the nucleus. However, class II HDAC mutant overexpression showed dramatic harmful effects by inducing mitochondrial dysfunction and apoptosis. In this work we provide two novel ways to circumvent harmful effects. First, we use the AAV system which allowed us to closely titrate the dosage of HDAC expression. The AAV system was already used in clinical trials (SERCA gene therapy). Second, by using an partial HDAC4 peptide we specifically seem to prevent the disease process of the heart and not essential functions such as mitochondrial function or cell survival. As a proof of concept, by expressing HDAC4 1-201 via AAVs, we show here for the first time, that this concept is a new promising therapeutic approach. Given the previous experience with the overexpression of putatively protective proteins in the same animal model, this was not expected.

Upstream Regulation Could Serve as an Additional Tool

With the identification of a critical PKA dependent protease (abhd5) we have identified the upstream signaling molecule that induced cardioprotective HDAC4 proteolysis. Abhd5 was not described as a protease and the involvement in potential cardioprotective pathways is new. Under normal conditions, abhd5 is bound to lipid droplets (LDs) and is involved in the regulation of lipolysis.

1. Backs, J., et al., *CaM kinase II selectively signals to histone deacetylase 4 during cardiomyocyte hypertrophy*. J Clin Invest, 2006. 116(7): p. 1853-64.
2. Backs, J., et al., *The delta isoform of CaM kinase II is required for pathological cardiac hypertrophy and remodeling after pressure overload*. Proc Natl Acad Sci USA, 2009. 106(7): p. 2342-7.
3. Song, K., et al., *The transcriptional coactivator CAMTA2 stimulates cardiac growth by opposing class II histone deacetylases*. Cell, 2006. 125(3): p. 453-66.
4. Sun, Q., et al., *Role of myocyte enhancing factor 2B in epithelial myofibroblast transition of human gingival keratinocytes*. Exp Biol Med (Maywood), 2012. 237 (2): p. 178-85.
5. Kim, Y., et al., *The MEF2D transcription factor mediates stress-dependent cardiac remodeling in mice*. J Clin Invest, 2008. 118(1): p. 124-32.
6. Czubryt, M. P., et al., *Regulation of peroxisome proliferator-activated receptor gamma coactivator 1 alpha (PGC-1 alpha) and mitochondrial function by MEF2 and HDAC5*. Proc Natl Acad Sci USA, 2003. 100(4): p. 1711-6.

---

The invention claimed is:

1. A method of treating or preventing heart failure comprising administering an effective amount of abhydrolase containing domain 5 (ABHD5) having an amino acid sequence as defined by one of SEQ ID NOs:1 to 5 or a variant thereof to a patient exhibiting symptoms of heart failure, wherein the variant has at least 95% sequence identity with one or more of SEQ ID NOs:1 to 5 and is capable of cleaving histone deacetylase 4 (HDAC4) following amino acid 201 to produce HDAC-NT.

2. The method of claim 1, wherein said ABHD5 variant is a substitution variant of human ABHD5, wherein at least one tryptophan selected from the group consisting of the tryptophan at position 19, the tryptophan at position 23 and the tryptophan at position 27 is replaced by an alanine.

3. The method of claim 1, wherein said ABHD5 variant is a substitution variant of mouse or rat ABHD5, wherein at least one tryptophan selected from the group consisting of the tryptophan at position 22, the tryptophan at position 26 and the tryptophan at position 30 is replaced by an alanine.

* * * * *